(12) United States Patent
Ow et al.

(10) Patent No.: US 11,230,919 B2
(45) Date of Patent: Jan. 25, 2022

(54) TRACERS FOR PETROLEUM RESERVOIRS

(71) Applicant: Saudi Arabian Oil Company, Dhahran (SA)

(72) Inventors: Hooisweng Ow, Woburn, MA (US); Rena Shi, Cambridge, MA (US); Jason R. Cox, Ashland, MA (US); Sehoon Chang, Cambridge, MA (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/252,228

(22) Filed: Jan. 18, 2019

(65) Prior Publication Data

US 2019/0218907 A1 Jul. 18, 2019

Related U.S. Application Data

(60) Provisional application No. 62/619,000, filed on Jan. 18, 2018, provisional application No. 62/758,046, filed on Nov. 9, 2018.

(51) Int. Cl.
*C07D 471/02* (2006.01)
*C07D 471/04* (2006.01)
(Continued)

(52) U.S. Cl.
CPC ............ *E21B 47/11* (2020.05); *C07D 213/55* (2013.01); *C07D 213/79* (2013.01);
(Continued)

(58) Field of Classification Search
None
See application file for complete search history.

(56) References Cited

U.S. PATENT DOCUMENTS

| 4,772,563 A | 9/1988 | Evangelista et al. |
| 5,124,268 A | 6/1992 | Dakubu |

(Continued)

FOREIGN PATENT DOCUMENTS

EP 0171978 A1 * 2/1986 ........... G01N 33/533

OTHER PUBLICATIONS

Pallenberg et al. "Synthesis and Characterization of Some Copper(l) Phenanthroline Complexes" Inorg. Chem. 1995, 34, 2833-2840 (Year: 1995).*

(Continued)

*Primary Examiner* — Charles R Nold
(74) *Attorney, Agent, or Firm* — Fish & Richardson P.C.

(57) ABSTRACT

The disclosure features methods of analyzing a fluid extracted from a reservoir, the methods including introducing a first composition featuring a first complexing agent into a reservoir at a first location, extracting a fluid from the reservoir at a second location different from the first location, combining the fluid with a second composition featuring a concentration of a lanthanide ion to form a third composition featuring a concentration of a complex formed by the first complexing agent and the lanthanide ion, exposing a quantity of the complex to electromagnetic radiation for a first time period ending at a time $t_0$, detecting fluorescence emission from the quantity of the complex for a second time period starting at a time $t_1 > t_0$, where $t_1 - t_0$ is greater than 2 microseconds, and determining information about a fluid flow path between the first location and the second location.

5 Claims, 20 Drawing Sheets

(51) Int. Cl.

| | | |
|---|---|---|
| *C09K 11/07* | (2006.01) | |
| *E21B 47/11* | (2012.01) | |
| *E21B 49/08* | (2006.01) | |
| *G01N 21/64* | (2006.01) | |
| *C07D 213/79* | (2006.01) | |
| *C09K 8/03* | (2006.01) | |
| *C07D 401/04* | (2006.01) | |
| *C07D 213/89* | (2006.01) | |
| *C07D 213/55* | (2006.01) | |
| *E21B 43/16* | (2006.01) | |

(52) U.S. Cl.
CPC ......... *C07D 213/89* (2013.01); *C07D 401/04* (2013.01); *C07D 471/04* (2013.01); *C09K 8/03* (2013.01); *C09K 11/07* (2013.01); *E21B 43/16* (2013.01); *E21B 49/08* (2013.01); *G01N 21/643* (2013.01); *G01N 21/6408* (2013.01); *C09K 2211/1018* (2013.01); *C09K 2211/182* (2013.01); *E21B 49/0875* (2020.05); *G01N 2021/6441* (2013.01); *G01N 2201/129* (2013.01)

(56) References Cited

U.S. PATENT DOCUMENTS

| 5,168,927 | A | 12/1992 | Stegenneier |
|---|---|---|---|
| 6,691,780 | B2 | 2/2004 | Nguyen et al. |
| 7,032,662 | B2 | 4/2006 | Malone |
| 2011/0012331 | A1 | 1/2011 | Kim |
| 2012/0115128 | A1 | 5/2012 | Miller |
| 2013/0084643 | A1 | 4/2013 | Connnnarieu |
| 2014/0323363 | A1 | 10/2014 | Perriat |
| 2016/0003040 | A1 | 1/2016 | Jessheim et al. |
| 2017/0199124 | A1 | 7/2017 | Bolduc et al. |

OTHER PUBLICATIONS

Agenet et al., "Fluorescent Nanobeads: a First Step Toward Intelligent Water Tracers," Society of Petroleum Engineers, presented at the SPE International Oilfield Nanotechnology Conference held in Noordwijk, the Netherlands, Jun. 12-14, 2012, 13 pages.

Brichart et al., "The Use of Fluorescent Tracers for Inhibitor Concentration Monitoring Useful for Scale Inhibitor," International Petroleum Technology Conference, IPTC-17933-MS, presented at the International Petroleum Technology Conference held in Kuala Lumpur, Dec. 10-12, 2014, 8 pages.

Marais et al., "Time-Resolved Fluorescence for Real-Time Monitoring of Both Scale and Corrosion Inhibitors: a Game-Changing Technique," SPE 179867, Society of Petroleum Engineers, presented at the SPE International Oilfield Scale Conference and Exhibition held in Aberdeen, Scotland, May 11-12, 2016 11 pages.

Martini et al., "How to Monitor Scale Inhibitor Squeeze using Simple TRF Tracers," Society of Petroleum Engineers, presented at the SPE International Symposium on Oilfield Chemistry held in the Woodlands, Texas, Apr. 13-15, 2015, 8 pages.

Bao et al., "Luminescence properties of the co-luminescence groups of Sm—La-pyridyl carboxylic acids," Journal of Rare Earths, 30(4), 320-324, Apr. 2012, 5 pages.

Borrini et al., "Water Soluble PDCA Derivatives for Selective Ln(III)/An(III) and Am(III)/Cm(III) Separation," Solvent Extraction and Ion Exchange, 33(3), 224-235, Oct. 2014, 30 pages.

Chen et al., "Analysis of the solution conformations of T4 lysozyme by paramagnetic NMR spectroscopy," Physical Chemistry Chemical Physics (2016), 18(8), 5850-5859, 10 pages.

Coates et al, "Enhancement of luminescence of europium(m) ions in water by use of synergistic chelation. Part 1.1: 1 and 2: 1 complexes," J. Chem. Soc, Perkin Trans., Jan. 1, 1996 (Jan. 1, 1996), pp. 1275-1282.

Edwards et al., "Extending the distance range accessed with continuous wave EPR with Gd3+ spin probes at high magnetic fields," Physical Chemistry Chemical Physics, 15(27), 11313-11326, 2013, 14 pages.

Gordon-Grossman et al., "W-Band pulse EPR distance measurements in peptides using Gd3+− dipicolinic acid derivatives as spin labels," Physical Chemistry Chemical Physics, 13(22), 10771-10780, 2011, 10 pages.

Grutzke et al., "Heptacoordinate Heteroleptic Salan (ONNO) and Thiosalan (OSSO) Titanium(IV) Complexes: Investigation of Stability and Cytotoxicity," Inorganic Chemistry 54(14), 6697-6706, Jul. 2015, 10 pages.

He et al., "Luminescent Europium Chelates Synthesis and Fluorescence Properties," Sensors and Materials (2007), 19(2), 123-132, 10 pages.

Kaushik et al., "Gd(III) and Mn(II) complexes for dynamic nuclear polarization: small molecular chelate polarizing agents and applications with site-directed spin labeling of proteins," Physical Chemistiy Chemical Physics, 18(39), 27205-27218, 2016, 36 pages.

Labbe et al., "Development of metal-chelating inhibitors for the Class II fructose 1,6-bisphosphate (FBP) aldolase," Journal of Inorganic Biochemistry, 112, 49-58, Jul. 2012, 10 pages.

Larsen et al, "Efficient Synthesis of 4,7-Diamino Substituted 1,10-Phenanthroline-2,9-dicarboxamides," Organic Letters, vol. 13, No. 13, Jul. 1, 2011 (Jul. 1, 2011), pp. 3546-3548.

Li et al., "Magic Angle Spinning NMR Structure Determination of Proteins from Pseudocontact Shifts," Journal of the American Chemical Society, 135(22), 8294-8303, May 2013, 10 pages.

Li et al., "Thiol-ene reaction: a versatile tool in site-specific labelling of proteins with chemically inert tags for paramagnetic NMR," Chemical Communications, Cambridge, United Kingdom, 48(21), 2704-2706, 2012, 18 pages.

Manna et al, "Complexation behavior of trivalent actinides and lanthanides with 1,10-phenanthroline-2,9-dicarboxylic acid based ligands: insight from density functional theory," Physical Chemistry Chemical Physics, vol. 14, No. 31, Jan. 1, 2012 (Jan. 1, 2012), p. 11060.

Melton et al, "Complexes of Greatly Enhanced Thermodynamic Stability and Metal Ion Size-Based Selectivity, Formed by the Highly Preorganized Non-Macrocyclic Ligand 1, 10-Phenanthroline-2, 9-dicarboxylic Acid: A Thermodynamic and Crystallographic Study," Inorganic Chemistry, vol. 45, No. 23, Nov. 1, 2006 (Nov. 1, 2006), pp. 9306-9314.

Ogden et al, "Complexation of Am(III) and Nd(in) by 1, 10-Phenanthroline-2, 9-Di carboxylic Acid," Journal of Solution Chemistry, vol. 42, No. 1, Dec. 27, 2012 (Dec. 27, 2012), pp. 211-225.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later," Inorganic Chemistry, 41(6), 1436-1445, Feb. 2002, 10 pages.

PCT International Search Report and Written Opinion in International Appln. No. PCT/US2019/014166, dated Aug. 6, 2019, 24 pages.

Potapov et al., "Nanometer-Scale Distance Measurements in Proteins Using Gd3+ Spin Labeling," Journal of the American Chemical Society, 132(26), 9040-9048, Jun. 2010, 9 pages.

Schmidt et al., "Copper dipicolinates as peptidomimetic ligands for the Src SH2 domain," Bioorganic & Medicinal Chemistry Letters, 14(16), 4203-4206, Aug. 2004, 4 pages.

Schmidt et al., "Synthesis of Mono- and Dinuclear Vanadium Complexes and Their Reactivity toward Dehydroperoxidation of Alkyl Hydroperoxides," Inorganic Chemistry 56(3), 1319-1332, 2017, 14 pages.

Su et al., "A Dipicolinic Acid Tag for Rigid Lanthanide Tagging of Proteins and Paramagnetic NMR Spectroscopy," Journal of the American Chemical Society, 130(32), 10486-10487, Jul. 2008, 2 pages.

Tang et al., "Synthesis and fluorescence properties of Tb(III) complexes with pyridine-2,6-dicarboxylic acid derivatives," Journal of Central South University of Technology (English Edition), 15(5), 599-605, Oct. 2008. 7 pages.

(56) References Cited

OTHER PUBLICATIONS

Invitation to Pay Additional Fees and, Where Applicable, Protest Fee issued in International Application No. PCT/US2019/014166 on Jun. 3, 2019, 16 pages.
Armelao et al., "Design of luminescent lanthanide complexes: From molecules to highly efficient photo-emitting materials," Coordination Chemistry Reviews, vol. 254, 5-6, Mar. 2010, 19 pages.
Bünzli and Piguet, "Taking advantage of luminescent lanthanide ions," Chemical Society Reviews, vol. 34, Issue 12, Sep. 2005, 30 pages.
Chen et al., "Impact of Irreversible Retention on Tracer Deployments; Constraining Novel Material Deployments," SPE 188890-MS, in SPE Abu Dhabi International Petroleum Exhibition and Conference, Society of Petroleum Engineers, Nov. 2017, 8 pages.
Chen et al., "Improved Reservoir History Matching and Prudction Optimization with Tracer Data," SPE 191523-MS, in SPE Annual Technical Conference and Exhibition, Society of Petroleum Engineers, Sep. 2018, 15 pages.
Du and Guan, "Interwell tracer tests: lessons learnted from past field studies," SPE 93140-MS, in SPE Asia Pacific Oil and Gas Conference and Exhibition, Society of Petroleum Engineers, Apr. 5-7, 2005, 9 pages.
Dugstad, "Chapter 6: Well-to-well tracer tests," in Petroleum Engineering Handbook, 5, pp. 651-683, 2007, 31 pages.
Freeze and Cherry, "Chapter 9: Groundwater Contamination," in Groundwater, Englewood Cliffs, NJ: Prentice-Hall, Inc., p. 604, 1979, 80 pages.
Galdiga and Greibrokk, "Ultra-trace determination of flurinated aromatic carboxylic acids in aqueous reservoir fluids using solid-phase extraction in combination with gas chromatography-mass spectrometry," Journal of Chromatography, vol. 793, Issue 2, Jan. 16, 1998, 10 pages.
George et al., "Modified Dipicolinic Acid Ligands for Sensitation and Europium (III) Luminescence," Inorganic Chemistry, vol. 45, No. 4, Feb. 1, 2006, 6 pages.
Hagoot, "The response of interwell tracer tests in watered-out reservoirs," SPE 11131-MS, in SPE Annual Technical Conference and Exhibition, Society of Petroleum Engineers, Jan. 1982, 21 pages.
Huseby et al., "Assessing EOR potential from partitioning tracer data," SPE 172808-MS, in SPE Middle East Oil and Gas Show and Conference, Society of Petroleum Engineers, Mar. 2015, 15 pages.
Jenkins et al., "Ultratrace Determination of Selected Lanthanides by Luminescence Enhancement," Analytical Chemistry, vol. 68, No. 17, Jan. 1, 1996, 7 pages.
Khan et al., "Optimizing waterflood management in a giant UAE carbonate oil field using simulation-based streamlines," SPE 171777-MS, in Abu Dhabi International Petroleum Exhibition and Conference, Society of Petroleum Engineers, Nov. 10-13, 2014, 9 pages.
Kornberger and Thiele, "Experiences with an Efficient Rate-Management Approach for the 8th Tortonian Reservoir in the Vienna Basin," SPE 166393-PA, SPE Reservoir Evaluation and Engineering, vol. 17, No. 2, May 2014, 12 pages.
Kosynkin and Alaskar, "Oil Industry First Interwell Trial of Reservoir Nanoagent Tracers," SPE 181551-MS, in SPE Annual Technical Conference and Exhibition, Society of Petroleum Engineers, Sep. 2016, 15 pages.
Muller and Seubert, "Ultra trace determination of fluorobenzoic acids in tap and reservoir water using solid-phase extraction and gas chromatography-mass spectrometry," Journal of Chromatography A, 1260, Oct. 2012, 7 pages.
Parker and Williams, "Getting excited about lanthanide complexation chemistry," Journal of the Chemical Society, Dalton Transactions, vol. 18, 1996, 16 pages.
Parker et al., "Being excited by lanthanide coordination complexes: aqua species, chirality, excited-state chemistry, and exchange dynamics," Chemical Reviews, vol. 102, Issue 6, May 2002, 34 pages.
Sabbatini et al., "Luminescent lanthanide complexes as photochemical supramolecular devices," Coordination Chemistry Reviews, vol. 123, issue 1-2, Feb. 1993, 28 pages.
Sammes and Yshioglu, "Modern bioassays using metal chelates as luminescent probes," Natural Product Reports, vol. 31, No. 1, 1996, 28 pages.
Sanni et al., "A field case study of inter-well chemical tracer test," in SPE International Symposium on Oilfield Chemistry, Society of Petroleum Engineers, Apr. 2015, 17 pages.
Sanni et al., "Pushing the envelope of residual oil measurement: A field case study of a new class of inter-well chemical tracers," Journal of Petroleum Science and Engineering, vol. 163, 2018, 19 pages.
Serres-Piole et al., "Direct sensitive simultaneous determination of fluorinated benzoic acids in oil reservoir waters by ultra high-performance liquid chromatography-tandem mass spectrometry," Journal of Chromatography A, 1218, Aug. 2011, 6 pages.
Stryer et al., "Diffusion-enhanced fluorescence energy transfer," Annual Review of Biophysics and bioengineering, vol. 11, Issue 1, 1982, 21 pages.
Tang et al., "Synthesis of Novel Derivatives of Pyridine-2,6-dicarboxylic Acid," Synthetic Communications: An International Journal for Rapid Communication of Synthetic Organic Chemistry, 36(14), 2027-2034, Jun. 2006, 9 pages.
Toulhoat, "Experimentation and Modelling of U, Th and Lanthanides Transport in Fissured Rocks: Influence of Complexation," MRS Proceedings, vol. 50, Jan. 1, 1985, 8 pages.
Wang et al., "The Design and Implementation of a Full Field Inter-Well Tracer Program on a Giant UAE Carbonate Oil Field," in Abu Dhabi International Petroleum Exhibition and Conference, Society of Petroleum Engineers, SPE-177527-MS, Nov. 2015, 8 pages.
Yang et al., "The Co-Luminescence Groups of Sm—La-pyridyl Carboxylic Acids and the Binding Characteristics between the Selected Doped Complex and Bovine Serum Albumin," Bulletin of the Korean Chemical Society 33(4), 1303-1309, Apr. 20, 2012, 7 pages.
Zemel, "Chapter 3: Tracers in the Oil Field," in Tracers in the Oil Field, Technology and Engineering, Elsevier, vol. 43, Jan. 1995, 47 pages.
Badgett et al., "Totalsynthese eines Neobetanidin-Derivates und des Neobetenamins," Helvetica Chimica Acta, 1970, 53(2): 433-448, English Summary.
Coates et al., "Enhancement of luminescence of europium(III) ions in water by use of synergistic chelation. Part 1. 1:1 and 2:1 complexes," J. Chem. Soc., Perkin Trans., Jan. 1996, 2:1275-1282.
Qianming et al., "Bspda Synthesis and its Europium (III) Complexes' Fluorescence," Chemical Industry Times, Jul. 2005, 19(7): 38-41, English Abstract.
Tang et al., "Synthesis of Eu(III) and Tb(III) Complexes with Novel Pyridine-2,6-Dicarboxylic Acid Derivatives and Their Fluorescence Properties," Front. Chem. China, 2006, 4: 408-413.
Yang et al., "Paramagnetic labeling of proteins and pseudocontact shift in structural biology," Chinese Journal of Magnetic Resonance, 2014, 31(2):155-171, English Abstract.

\* cited by examiner

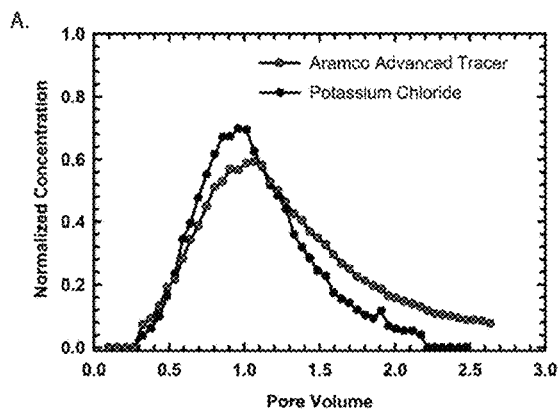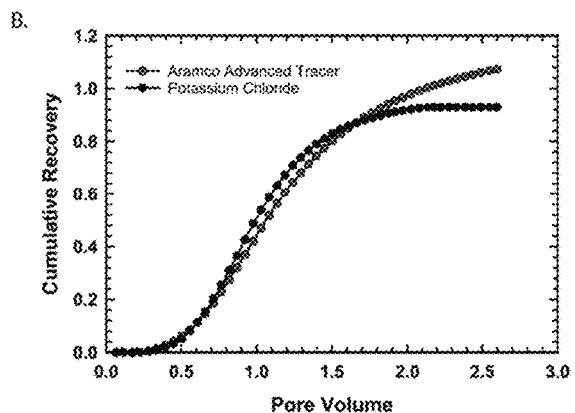
FIG. 15A  FIG. 15B
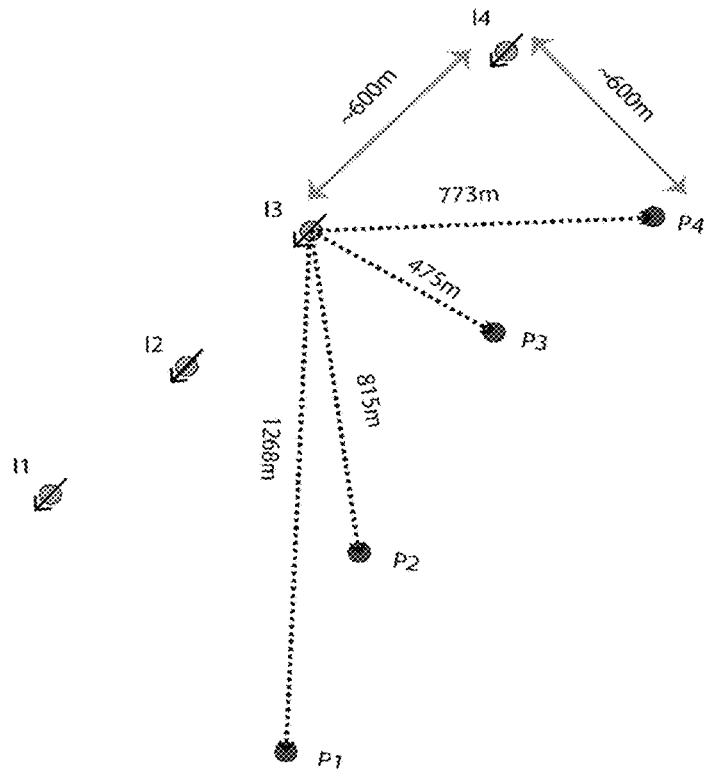
FIG. 16

TRACERS FOR PETROLEUM RESERVOIRS

CROSS-REFERENCE TO RELATED APPLICATIONS

This application claims priority to U.S. Provisional Application No. 62/619,000, filed on Jan. 18, 2018, and to U.S. Provisional Application No. 62/758,046, filed on Nov. 9, 2018, the entire contents of each of which are incorporated herein by reference.

TECHNICAL FIELD

This disclosure relates to the analysis of petroleum reservoirs using tracers, and methods of making tracers.

BACKGROUND

A petroleum reservoir is an underground pool of hydrocarbon compounds contained in porous or fractured rock formations. The petroleum in the reservoir is accessed through one or more borings in the earth that penetrate the material above the reservoir and enable transport of the petroleum to the surface. Water flooding is used, for example, to increase the pressure within the reservoir, thereby increasing oil production rates; and to displace hydrocarbons with the reservoir. Water is ideal for flooding reservoirs due to its ready availability and immiscibility with hydrocarbons. Determining the presence of fluid flow paths between oil wells, and the flow capacity between them, allows for a more detailed description of reservoir heterogeneity and facilitates water flood rate management.

SUMMARY

Cross-well tracers, also referred to as inter-well tracers, can be used to obtain information about reservoir fluid flow patterns by injecting the tracer at an injection location, and subsequently retrieving and analyzing a quantity of the injected tracer at a producing location downstream from the injection location. The ease-of-use and overall utility of a cross-well tracer depends on a number of attributes, including (1) lesser retention in rock and earth that the tracer is exposed to when traversing a fluid flow path in a reservoir, (2) thermal stability and inertness to the various compounds and materials the tracer encounters in the reservoir, (3) minimal purification, workup, and derivatization after extraction from the reservoir, (4) detectability at lesser concentrations after extraction from the reservoir, (5) a measurable and sensitive response independent of minor variations in the structure of the tracer, and (6) detectability of the response over competing measurement signals attributable to natural constituents in fluid extracted from a reservoir, such as polyaromatic hydrocarbons and salts (that is, background noise).

This disclosure features complexing agents for use as cross-well tracers. The complexing agents exhibit weak retention in rock, are thermally and chemically stable, and are typically used without purification after extraction. Instead of undergoing chemical derivatization after extraction, the complexing agents can conveniently be exposed to compositions including one or more lanthanide ions to form complexes.

The complexes formed, when exposed to excitation light, emit a fluorescence signal that is temporally delayed relative to fluorescence signals from other components of the extracted reservoir fluid. As a result, time-gated detection methods can be used to eliminate the fluorescence signals from the other components, allowing essentially background-free measurement of the complexes. Detection of tracer concentrations of parts-per-quadrillion (ppq) or even less, on a mass/mass (m/m) basis, can be achieved. For example, tracer concentrations of 100 ppq m/m or less (such as 50 ppq m/m or less, 25 ppq m/m or less, 20 ppq m/m or less, 15 ppq m/m or less, 10 ppq m/m, 5 ppq m/m, 2 ppq m/m, 1 ppq m/m) can be achieved. Within extracted fluid, tracer concentrations of 10 picomolar (pM) or less (such as 1 pM or less, 500 femtomolar (fM) or less, 200 fM or less, 100 fM or less, 50 fM or less, 25 fM or less, 15 fM or less, 10 fM or less, 5 fM or less, 1 fM or less, 500 attomolar (aM) or less, 200 aM or less, 100 aM or less, 50 aM or less) can be quantitatively detected.

Complexing agents can also be derivatized to generate libraries of structurally unique identifiers which can be independently injected at multiple injection locations and extracted at a producing location, thus allowing the evaluation and comparison of fluid flow paths that span from each of the injection location to the producing location. Thus, the disclosed complexing agents can be used to reduce the time and costs associated with mapping the connectivity and heterogeneity of petroleum reservoirs and the management of water flooding-based petroleum extraction.

In a first aspect, this disclosure features methods for analyzing a fluid extracted from a reservoir. The methods can include the steps of introducing a first composition that includes a first complexing agent into a reservoir at a first location, extracting a fluid from the reservoir at a second location different from the first location, where the extracted fluid includes a concentration of the first complexing agent, combining the fluid with a second composition that includes a concentration of a lanthanide ion to form a third composition having a concentration of a complex formed by the first complexing agent and the lanthanide ion, exposing a quantity of the complex to electromagnetic radiation for a first time period ending at a time $t_0$, detecting fluorescence emission from the quantity of the complex for a second time period starting at a time $t_1 > t_0$, where $t_1 - t_0$ is greater than 2 microseconds, and determining information about a fluid flow path between the first location and the second location within the reservoir based on the detected fluorescence emission.

Examples of the methods can include any one or more of the following features.

The complex can include water. The complex can have a 1:1:2 molar ratio of lanthanide ion to first complexing agent to water. Alternatively, the complex can have a 1:2:0 molar ratio of lanthanide ion to first complexing agent to water. As another alternative, the complex can have a 1:2:1 molar ratio of lanthanide ion to first complexing agent to water. As a further alternative, the complex can have a 1:3:0 molar ratio of lanthanide ion to first complexing agent to water.

The lanthanide ion can be a member of the group that includes samarium, europium, terbium, and dysprosium.

The methods can include, prior to extracting the fluid from the reservoir, introducing a fourth composition with a second complexing agent into the reservoir at a third location, where the third location is different from the first location and the second location, and where the extracted fluid includes a concentration of the second complexing agent. The amount of the first complexing agent introduced into the reservoir can be the same as the amount of the second complexing agent introduced into the reservoir.

The methods can include, prior to extracting the fluid from the reservoir, introducing a fourth composition with a second complexing agent into the reservoir at a third location, where the third location is different from the first location and the second location, and introducing a fifth composition with a third complexing agent into the reservoir at a fourth location, where the fourth location is different from the first location, the second location, and the third location, and where the extracted fluid includes a concentration of the second complexing agent and a concentration of the third complexing agent. The amounts of the first, second, and third complexing agents introduced into the reservoir can be the same.

The methods can include, prior to combining the fluid with the second composition, separating the first complexing agent from the second complexing agent in the fluid, and separating the third complexing agent from the first and second complexing agents if the fluid includes the third complexing agent. The steps of separating the first and third complexing agents can include performing a chromatographic separation.

A wavelength of the electromagnetic radiation can be in an ultraviolet spectral region. The time interval $t_1$-$t_0$ can be greater than 5 microseconds (for example, greater than 25 microseconds).

The information about the fluid flow path can include any one or more of a concentration of the first complexing agent, a concentration of the second complexing agent, and a concentration of the third complexing agent.

The first complexing agent can be a tridentate ligand. The first complexing agent can be a compound having a general structure given by Formula (I), or an anion or salt of the structure given by Formula (I):

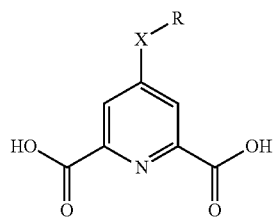

Formula (I)

In Formula (I), X can be present or absent, and when present, can be a member of the group that includes: $C_{1-10}$ alkylene, $C_{2-10}$ alkenylene, and $C_{2-10}$ alkynylene, where each of $C_{1-10}$ alkylene, $C_{2-10}$ alkenylene, and $C_{2-10}$ alkynylene can be optionally interrupted by one O, S, or NH.

In Formula (I), R can be a member of the group that includes (i) hydrogen, (ii) —$OR^a$, (iii) $C_{1-4}$ alkoxy, optionally substituted with 1-3 independent units of $R^b$, (iv) $C_{1-4}$ haloalkoxy, (v) —COH, (vi) —$CO_2R^a$, (vii) —$CONR^aR^a$, (viii) cyano, (ix) —$NR^aR^a$, (x) —$NR^aC(O)NR^aR^a$, (xi) —$NR^aC(O)OR^a$, (xii) —$NR^aC(O)R^a$, (xiii) -aryl that is optionally substituted with 1-3 independent units of $R^b$, (xiv) -heteroaryl including from 5-10 ring atoms, where 1-4 ring atoms are each independent members of the group that includes N, NH, O, and S, and where the heteroaryl can be optionally substituted with 1-3 independent units of $R^b$, (xv) —$C_{3-10}$ cycloalkyl that is optionally substituted with 1-4 independent units of $R^b$, (xvi) -heterocyclyl, including from 3-10 ring atoms, where 1-3 of the ring atoms are independent members of the group that includes N, NH and O, and where the heterocyclyl can be optionally substituted with 1-4 independent units of $R^b$, (xvii) $C_{1-4}$ thioalkoxy, (xviii) —$N_3$, (xix) —$CO_2H$, (xx) —$C(O)R^a$, (xxi) —$SO_{1-2}(R^a)$, and (xxii) —$O_nP(O)_nY_2$, where each occurrence of n can independently be 0 or 1, and where each occurrence Y can independently be one of —$OR^a$, $NR^aR^a$, and $C_{1-6}$ alkyl.

Each occurrence of $R^a$ in Formula (I) can independently be one of (i) H, (ii) $C_{1-8}$ alkyl optionally substituted with from 1-3 independent units of $R^b$, (iii) —($C_{0-6}$ alkylene)-$C_{3-10}$ cycloalkyl, where the cycloalkyl is optionally substituted with from 1-4 independent units of $R^b$, (iv) —($C_{0-6}$ alkylene)-heterocyclyl including from 3-10 ring atoms, where 1-3 of the ring atoms can each be independently members of the group that includes NH, O, and S, and where the heterocyclyl can optionally be substituted with from 1-4 independent units of $R^b$, (v) —($C_{0-6}$ alkylene)-($C_{6-10}$ aryl), where the aryl can be optionally substituted with from 1-5 independent units of $R^b$, or (vi) —($C_{0-6}$ alkylene)-heteroaryl including 5-10 ring atoms, where 1-4 of the ring atoms can each be independent members of the group that includes N, NH, O, and S, and where the heteroaryl can optionally be substituted with from 1-3 independent units of $R^b$.

Each occurrence of $R^b$ in Formula (I) can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including 3-10 ring atoms, where 1-3 of the ring atoms are each independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including from 5-10 ring atoms, where 1-4 of the ring atoms can each be independent members of the group that includes N, NH, O, and S, (xiii) —$S(O)_{1-2}$($C_{1-4}$ alkyl), (xiv) —NR'R", (xv) —OH, (xvi) —$S(O)_{1-2}$(NR'R"), (xvii) —$C_{1-4}$ thioalkoxy, (xviii) —$NO_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R").

Each occurrence of R' and R" can be an independent member of the group that includes H and $C_{1-4}$ alkyl, or, if R' and R" are bonded to the same atom, R' and R" together with the atom to which each is attached can form a ring that includes from 3-8 ring atoms, and the ring can include: (a) from 1-7 ring carbon atoms; and (b) 0-3 ring heteroatoms, in addition to the atom attached to R' and R", which are each independent members of the group that includes N, NH, O, and S.

In Formula (I), X can be $C_{1-10}$ alkylene. R can be selected from the group that includes (ii) —$OR^a$, where the $R^a$ of —$OR^a$ is not (i) H or (ii) $C_{1-8}$ alkyl substituted with —($C_{0-3}$ alkylene)-$C_{3-6}$ cycloalkyl, (vi) —$CO_2R^a$, where the $R^a$ of —$CO_2R^a$ is not H, (viii) cyano, (ix) —$NR^aR^a$, (x) —$NR^aC(O)NR^aR^a$, (xi) —$NR^aC(O)OR^a$, (xii) —$NR^aC(O)R^a$, (xiii) -aryl that is optionally substituted with from 1-3 independent units of $R^b$, (xiv) -heteroaryl including from 5-10 ring atoms, where 1-4 ring atoms are independent members of the group that includes N, NH, O, and S, where the heteroaryl is optionally substituted with from 1-3 independent units of $R^b$, (xv) —$C_{3-10}$ cycloalkyl that is optionally substituted with from 1-4 independent units of $R^b$, (xvi) -heterocyclyl including from 3-ring atoms, where 1-3 of the ring atoms are independent members of the group that includes N, NH and O, and where the heterocyclyl is optionally substituted with from 1-4 independent units of $R^b$, (xx) —C(O)$R^a$, and (xxi) —SO$_{1-2}$($R^a$). Each occurrence of $R^a$ can be an independent members of the group that includes (i) H, (ii) $C_{1-8}$ alkyl optionally substituted with from 1-3 independent units of $R^b$, (iii) —($C_{0-6}$ alkylene)-$C_{3-10}$ cycloalkyl, where the cycloalkyl is optionally substituted with from 1-4 independent units of $R^b$, (iv) —($C_{0-6}$ alkylene)-heterocyclyl including from 3-10 ring atoms, where 1-3 of the ring atoms are independent members of the group that includes NH, O, and S, and where the heterocyclyl is optionally substituted with 1-4 independent units of $R^b$, (v) —($C_{0-6}$ alkylene)-($C_{6-10}$ aryl), where the aryl is optionally substituted with 1-5 independent units of $R^b$, or (vi) —($C_{0-6}$ alkylene)-heteroaryl including from 5-10 ring atoms, where 1-4 of the ring atoms can be independent members of the group that includes N, NH, O, and S, and where the heteroaryl can be optionally substituted with 1-3 independent units of $R^b$. Each occurrence of $R^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including 3-10 ring atoms, where 1-3 of the ring atoms can be independent members of the group that includes NH, O, and S, and where the heterocyclyl can be optionally substituted with 1-4 independent units of $C_{1-4}$ alkyl; (xi) —($C_{0-3}$ alkylene)-phenyl; (xii) —($C_{0-3}$ alkylene)-heteroaryl including 5-10 ring atoms, where 1-4 of the ring atoms can be independent members of the group that includes N, NH, O, and S, (xiii) —S(O)$_{1-2}$($C_{1-4}$ alkyl), (xiv) —NR'R", (xv) —OH, (xvi) —S(O)$_{1-2}$(NR'R"), (xvii) —$C_{1-4}$ thioalkoxy, (xviii) —NO$_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R"). Each occurrence of R' and R" can be an independent member of the group that includes H and $C_{1-4}$ alkyl, or, if R' and R" are bonded to the same atom, R' and R" together with the atom to which each is attached can form a ring that includes 3-8 ring atoms, where the ring includes (a) 1-7 ring carbon atoms, and (b) 0-3 ring heteroatoms (in addition to the atom attached to R' and R"), which are each independent members of the group that includes N, NH, O, and S.

In Formula (I), X can be —CH$_2$—. In Formula (I), R can be (ii) —OR$^a$, where the R$^a$ of —OR$^a$ is not (i) H or (ii) $C_{1-8}$ alkyl substituted with —($C_{0-3}$ alkylene)-$C_{3-6}$ cycloalkyl.

In Formula (I), R can be a member of the group that includes (ix) —NR$^a$R$^a$, where one R$^a$ is H, (x) —NR$^a$C(O)NR$^a$R$^a$, where at least one R$^a$ is H, (xi) —NR$^a$C(O)OR$^a$, where the R$^a$ bonded to N is H, and (xii) —NR$^a$C(O)R$^a$.

In Formula (I), R can be a member of the group that includes (vi) —CO$_2$R$^a$, where the R$^a$ of —CO$_2$R$^a$ is not H, and (xx) —C(O)R$^a$.

The first complexing agent can be tetradentate.

The first complexing agent can be a compound having a general structure given by Formula (II), or an anion or salt of a compound having the general structure of Formula (II):

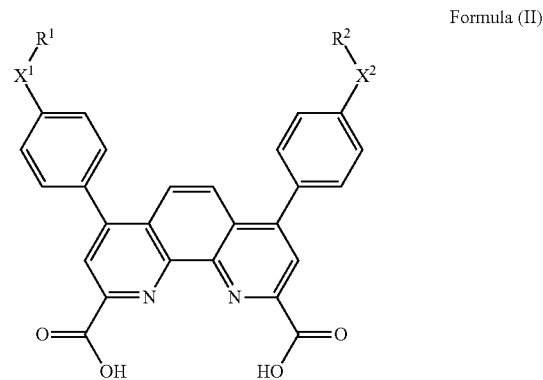

Formula (II)

In Formula (II), each of $X^1$ and $X^2$ can be independently present or absent, and when one or both are present, each can be an independent member of the group that includes $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH.

In Formula (II), each $R^1$ and $R^2$ is an independent member of the group that includes (i) hydrogen, (ii) —OR$^a$, (iii) $C_{1-4}$ alkoxy optionally substituted with 1-3 independent units of $R^b$, (iv) $C_{1-4}$ haloalkoxy, (v) —COH, (vi) —CO$_2$R$^a$, (vii) —CONR$^a$R$^a$, (viii) cyano, (ix) —NR$^a$R$^a$, (x) —NR$^a$C(O)NR$^a$R$^a$, (xi) —NR$^a$C(O)OR$^a$, (xii) —NR$^a$C(O)R$^a$, (xiii) -aryl that is optionally substituted with 1-3 independent units of $R^b$, (xiv) -heteroaryl including 5-10 ring atoms, where 1-4 ring atoms are each independent members of the group that includes N, NH, O, and S, and where the heteroaryl is optionally substituted with 1-3 independent units of $R^b$, (xv) —$C_{3-10}$ cycloalkyl that is optionally substituted with 1-4 independent units of $R^b$, (xvi) -heterocyclyl including 3-ring atoms, where 1-3 of the ring atoms can each be independent members of the group that includes N, NH and O, where the heterocyclyl is optionally substituted with 1-4 independent units of $R^b$, (xvii) $C_{1-4}$ thioalkoxy, (xviii) —N$_3$, (xix) —CO$_2$H, (xx) —C(O)R$^a$, (xxi) —SO$_{1-2}$(R$^a$), and (xxii) —O$_n$P(O)$_n$Y$_2$, where each n is independently 0 or 1, and each Y is an independent member of the group that includes —OR$^a$, NR$^a$R$^a$, and $C_{1-6}$ alkyl.

Each occurrence of $R^a$ can be an independent member of the group that includes (i) H, (ii) $C_{1-8}$ alkyl optionally substituted with 1-3 independent units of $R^b$, (iii) —($C_{0-6}$ alkylene)-$C_{3-10}$ cycloalkyl, where the cycloalkyl is optionally substituted with 1-4 independent units of $R^b$, (iv) —($C_{0-6}$ alkylene)-heterocyclyl including 3-10 ring atoms, where 1-3 of the ring atoms are independent members of the group that includes NH, O, and S, and the heterocyclyl is optionally substituted with 1-4 independent units of $R^b$, (v) —($C_{0-6}$ alkylene)-($C_{6-10}$ aryl), where the aryl is optionally substituted with 1-5 independent units of $R^b$, or (vi) —($C_{0-6}$ alkylene)-heteroaryl including 5-10 ring atoms, where 1-4 of the ring atoms are independent members of the group that includes N, NH, O, and S, and the heteroaryl is optionally substituted with 1-3 independent units of $R^b$.

Each occurrence of $R^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including from 3-10 ring atoms, where 1-3 of the ring atoms are independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including 5-10 ring atoms, where 1-4 of the ring atoms are independent members of the group that includes N, NH, O, and S, (xiii) —S(O)$_{1-2}$($C_{1-4}$ alkyl), (xiv) —NR'R", (xv) —OH, (xvi) —S(O)$_{1-2}$(NR'R"), (xvii) —$C_{1-4}$ thioalkoxy, (xviii) —NO$_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R").

Each occurrence of R' and R" can be an independent member of the group that includes H and $C_{1-4}$ alkyl, or, if R' and R" are bonded to the same atom, R' and R" together with the atom to which each is attached can form a ring including 3-8 ring atoms, where the ring includes (a) 1-7 ring carbon atoms, and (b) 0-3 ring heteroatoms (in addition to the atom attached to R' and R") which are each independent members of the group that includes N, NH, O, and S.

In Formula (II), each of $X^1$ and $X^2$ can be independently present or absent, and when one or both are present, each can be an independent member of the group that includes $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH. Each of $R^1$ and $R^2$ can be an independent member of the group that includes (ii) —OR$^a$, (iii) $C_{1-4}$ alkoxy optionally substituted with 1-3 independent units of R$^b$, (iv) $C_{1-4}$ haloalkoxy, (vi) —CO$_2$R$^a$, (vii) —CONR$^a$R$^a$, (viii) cyano, (ix) —NR$^a$R$^a$, (x) —NR$^a$C(O)NR$^a$R$^a$, (xi) —NR$^a$C(O)OR$^a$, (xii) —NR$^a$C(O)R$^a$, (xiii) -aryl that is optionally substituted with 1-3 independent units of R$^b$, (xiv) -heteroaryl including 5-10 ring atoms, where 1-4 of the ring atoms are independent members of the group that includes N, NH, O, and S, and where the heteroaryl is optionally substituted with 1-3 independent units of R$^b$, (xv) —$C_{3-10}$ cycloalkyl that is optionally substituted with 1-4 independent units of R$^b$, (xvi) -heterocyclyl including 3-10 ring atoms, where 1-3 of the ring atoms are independent members of the group that includes N, NH and O, and where the heterocyclyl is optionally substituted with 1-4 independent units of R$^b$, (xix) —CO$_2$H, (xx) —C(O)R$^a$, and (xxi) —SO$_{1-2}$(R$^a$). Each occurrence of R$^a$ can be an independent member of the group that includes (i) H, (ii) $C_{1-8}$ alkyl optionally substituted with 1-3 independent units of R$^b$, (iii) —($C_{0-6}$ alkylene)-$C_{3-10}$ cycloalkyl, where the cycloalkyl is optionally substituted with 1-4 independent units of R$^b$, (iv) —($C_{0-6}$ alkylene)-heterocyclyl including 3-10 ring atoms, where 1-3 ring atoms are independent members of the group that includes NH, O, and S, and where the heterocyclyl is optionally substituted with 1-4 independent units of R$^b$, (v) —($C_{0-6}$ alkylene)-($C_{6-10}$ aryl), where the aryl is optionally substituted with 1-5 independent units of R$^b$, or (vi) —($C_{0-6}$ alkylene)-heteroaryl including 5-10 ring atoms, where 1-4 of the ring atoms can be independent members of the group that includes N, NH, O, and S, and where the heteroaryl is optionally substituted with 1-3 independent units of R$^b$. Each occurrence of R$^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including 3-10 ring atoms, where 1-3 ring atoms are independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including 5-10 ring atoms, where 1-4 ring atoms are independent members of the group that includes N, NH, O, and S, (xiii) —S(O)$_{1-2}$($C_{1-4}$ alkyl), (xiv) —NR'R", (xv) —OH, (xvi) —S(O)$_{1-2}$(NR'R"), (xvii) —$C_{1-4}$ thioalkoxy, (xviii) —NO$_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R").

Each occurrence of R' and R" can be an independent member of the group that includes H and $C_{1-4}$ alkyl, or, if R' and R" are bonded to the same atom, R' and R" together with the atom to which each is attached can form a ring including 3-8 ring atoms, where the ring includes (a) 1-7 ring carbon atoms, and (b) 0-3 ring heteroatoms (in addition to the atom attached to R' and R"), which are each independent members of the group that includes N, NH, O, and S.

In Formula (II), $X^1$ and $X^2$ can both be absent.

In Formula (II), $R^1$ and $R^2$ can each be independent members of the group that includes (ix) —NR$^a$R$^a$, (x) —NR$^a$C(O)NR$^a$R$^a$, (xi) —NR$^a$C(O)OR$^a$, and (xii) —NR$^a$C(O)R$^a$. Alternatively, in Formula (II), $R^1$ and $R^2$ can each be independent members of the group that includes (ix) —NHR$^a$, (x) —NHC(O)NHR$^a$, (xi) —NHC(O)OR$^a$, and (xii) —NHC(O)R$^a$. As another alternative, in Formula (II), $R^1$ and $R^2$ can each be (ix) —NHR$^a$.

In Formula (II), R$^a$ can be (ii) $C_{1-8}$ alkyl substituted with 1-3 independent units of R$^b$, where at least one of the R$^b$ is (xv) —OH. Alternatively, in Formula (II), $R^1$ and $R^2$ can each be (x) —NHC(O)NHR$^a$. As another alternative, in Formula (II), $R^1$ and $R^2$ can each be (xi) —NHC(O)OR$^a$. As a further alternative, in Formula (II), $R^1$ and $R^2$ can each be (xii) —NHC(O)R$^a$.

In Formula (II), each of $R^1$ and $R^2$ can be the same, or alternatively, each of $R^1$ and $R^2$ can be different.

The first complexing agent can be a compound having a general structure given by Formula (III), or an anion or salt of a compound having the general structure of Formula (III):

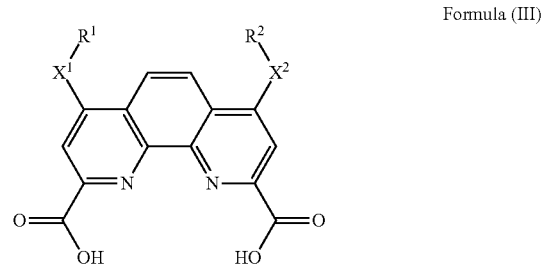

Formula (III)

In Formula (III), each of $X^1$ and $X^2$ can be independently present or absent, and when one or both are present, each can be an independent member of the group that includes $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH.

In Formula (II), each $R^1$ and $R^2$ is an independent member of the group that includes (i) hydrogen, (ii) —OR$^a$, (iii) $C_{1-4}$ alkoxy optionally substituted with 1-3 independent units of R$^b$, (iv) $C_{1-4}$ haloalkoxy, (v) —COH, (vi) —CO$_2$R$^a$, (vii) —CONR$^a$R$^a$, (viii) cyano, (ix) —NR$^a$R$^a$, (x) —NR$^a$C(O)NR$^a$R$^a$, (xi) —NR$^a$C(O)OR$^a$, (xii) —NR$^a$C(O)R$^a$, (xiii) -aryl that is optionally substituted with 1-3 independent units of R$^b$, (xiv) -heteroaryl including 5-10 ring atoms, where 1-4 ring atoms are each independent members of the group that includes N, NH, O, and S, and where the heteroaryl is optionally substituted with 1-3 independent units of R$^b$, (xv) —$C_{3-10}$ cycloalkyl that is optionally substituted with 1-4 independent units of R$^b$, (xvi) -heterocyclyl including 3-ring atoms, where 1-3 of the ring atoms can each be independent members of the group that includes N, NH and O, where the heterocyclyl is optionally substituted with 1-4 independent units of $R^b$, (xvii) $C_{1-4}$ thioalkoxy, (xviii) —$N_3$, (xix) —$CO_2H$, (xx) —C(O)$R^a$, (xxi) —$SO_{1-2}(R^a)$, (xxii) —$O_nP$ $(O)_nY_2$, where each n is independently 0 or 1, and (xxiii) halo (e.g., —F, —Cl, —Br, or —I), and each Y is an independent member of the group that includes —$OR^a$, $NR^aR^a$, and $C_{1-6}$ alkyl.

Each occurrence of $R^a$ can be an independent member of the group that includes (i) H, (ii) $C_{1-8}$ alkyl optionally substituted with 1-3 independent units of $R^b$, (iii) —($C_{0-6}$ alkylene)-$C_{3-10}$ cycloalkyl, where the cycloalkyl is optionally substituted with 1-4 independent units of $R^b$, (iv) —($C_{0-6}$ alkylene)-heterocyclyl including 3-10 ring atoms, where 1-3 of the ring atoms are independent members of the group that includes NH, O, and S, and the heterocyclyl is optionally substituted with 1-4 independent units of $R^b$, (v) —($C_{0-6}$ alkylene)-($C_{6-10}$ aryl), where the aryl is optionally substituted with 1-5 independent units of $R^b$, or (vi) —($C_{0-6}$ alkylene)-heteroaryl including 5-10 ring atoms, where 1-4 of the ring atoms are independent members of the group that includes N, NH, O, and S, and the heteroaryl is optionally substituted with 1-3 independent units of $R^b$.

Each occurrence of $R^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including from 3-10 ring atoms, where 1-3 of the ring atoms are independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including 5-10 ring atoms, where 1-4 of the ring atoms are independent members of the group that includes of N, NH, O, and S, (xiii) —S(O)$_{1-2}$($C_{1-4}$alkyl), (xiv) —NR'R", (xv) —OH, (xvi) —S(O)$_{1-2}$(NR'R"), (xvii) —$C_{1-4}$ thioalkoxy, (xviii) —$NO_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R").

Each occurrence of R' and R" can be an independent member of the group that includes H and $C_{1-4}$ alkyl, or, if R' and R" are bonded to the same atom, R' and R" together with the atom to which each is attached can form a ring including 3-8 ring atoms, where the ring includes (a) 1-7 ring carbon atoms, and (b) 0-3 ring heteroatoms (in addition to the atom attached to R' and R") which are each independent members of the group that includes N, NH, O, and S.

In Formula (III), each of $X^1$ and $X^2$ can be independently present or absent, and when one or both are present, each can be an independent member of the group that includes $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH. Each of $R^1$ and $R^2$ can be an independent member of the group that includes (ii) —$OR^a$, (iii) $C_{1-4}$ alkoxy optionally substituted with 1-3 independent units of $R^b$, (iv) $C_{1-4}$ haloalkoxy, (vi) —$CO_2R^a$, (vii) —$CONR^aR^a$, (viii) cyano, (ix) —$NR^aR^a$, (x) —$NR^aC(O)NR^aR^a$, (xi) —$NR^aC(O)OR^a$, (xii) —$NR^aC(O)R^a$, (xiii) -aryl that is optionally substituted with 1-3 independent units of $R^b$, (xiv) -heteroaryl including 5-10 ring atoms, where 1-4 of the ring atoms are independent members of the group that includes N, NH, O, and S, and where the heteroaryl is optionally substituted with 1-3 independent units of $R^b$, (xv) —$C_{3-10}$ cycloalkyl that is optionally substituted with 1-4 independent units of $R^b$, (xvi) -heterocyclyl including 3-10 ring atoms, where 1-3 of the ring atoms are independent members of the group that includes N, NH and O, and where the heterocyclyl is optionally substituted with 1-4 independent units of $R^b$, (xix) —$CO_2H$, (xx) —C(O)$R^a$, and (xxi) —$SO_{1-2}(R^a)$. Each occurrence of $R^a$ can be an independent member of the group that includes (i) H, (ii) $C_{1-8}$ alkyl optionally substituted with 1-3 independent units of $R^b$, (iii) —($C_{0-6}$ alkylene)-$C_{3-10}$ cycloalkyl, where the cycloalkyl is optionally substituted with 1-4 independent units of $R^b$, (iv) —($C_{0-6}$ alkylene)-heterocyclyl including 3-10 ring atoms, where 1-3 ring atoms are independent members of the group that includes NH, O, and S, and where the heterocyclyl is optionally substituted with 1-4 independent units of $R^b$, (v) —($C_{0-6}$ alkylene)-($C_{6-10}$ aryl), where the aryl is optionally substituted with 1-5 independent units of $R^b$, or (vi) —($C_{0-6}$ alkylene)-heteroaryl including 5-10 ring atoms, where 1-4 of the ring atoms can be independent members of the group that includes N, NH, O, and S, and where the heteroaryl is optionally substituted with 1-3 independent units of $R^b$.

Each occurrence of $R^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including 3-10 ring atoms, where 1-3 ring atoms are independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including 5-10 ring atoms, where 1-4 ring atoms are independent members of the group that includes N, NH, O, and S, (xiii) —S(O)$_{1-2}$($C_{1-4}$ alkyl), (xiv) —NR'R", (xv) —OH, (xvi) —S(O)$_{1-2}$(NR'R"), (xvii) —$C_{1-4}$ thioalkoxy, (xviii) —$NO_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R"). Each occurrence of R' and R" can be an independent member of the group that includes H and $C_{1-4}$ alkyl, or, if R' and R" are bonded to the same atom, R' and R" together with the atom to which each is attached can form a ring including 3-8 ring atoms, where the ring includes (a) 1-7 ring carbon atoms, and (b) 0-3 ring heteroatoms (in addition to the atom attached to R' and R"), which are each independent members of the group that includes N, NH, O, and S.

In Formula (III), $X^1$ and $X^2$ can both be absent.

In Formula (III), $R^1$ and $R^2$ can each be independent members of the group that includes (ix) —$NR^aR^a$, (x) —$NR^aC(O)NR^aR^a$, (xi) —$NR^aC(O)OR^a$, and (xii) —$NR^aC(O)R^a$. Alternatively, in Formula (III), $R^1$ and $R^2$ can each be independent members of the group that includes (ix) —$NHR^a$, (x) —$NHC(O)NHR^a$, (xi) —$NHC(O)OR^a$, and (xii) —$NHC(O)R^a$. As another alternative, in Formula (III), $R^1$ and $R^2$ can each be (ix) —$NHR^a$.

In Formula (III), $R^a$ can be (ii) $C_{1-8}$ alkyl substituted with 1-3 independent units of $R^b$, where at least one of the $R^b$ is (xv) —OH. Alternatively, in Formula (III), $R^1$ and $R^2$ can each be (x) —NHC(O)NHR$^a$. As another alternative, in Formula (III), $R^1$ and $R^2$ can each be (xi) —NHC(O)OR$^a$. As a further alternative, in Formula (III), $R^1$ and $R^2$ can each be (xii) —NHC(O)R$^a$.

In Formula (III), each of $R^1$ and $R^2$ can be the same, or alternatively, each of $R^1$ and $R^2$ can be different.

Embodiments of the methods can also include any of the other features discussed, including features associated with different embodiments, in any combination unless expressly stated otherwise.

In another aspect, this disclosure features methods of forming a complex that includes a complexing agent and a lanthanide ion, the methods including introducing the complexing agent into a subterranean reservoir at a first location, allowing the complexing agent to propagate through at least a portion of the reservoir to a second location different from the first location, extracting the complexing agent from the reservoir at the second location, and combining the extracted complexing agent with a solution that includes the lanthanide ion to form the complex, where the complexing agent has a general structure given by Formula (I), or an anion or salt of the structure given by Formula (I):

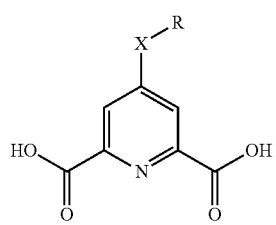

Formula (I)

In Formula (I), X can be present or absent, and when present, can be a member of the group that includes: $C_{1-10}$ alkylene, $C_{2-10}$ alkenylene, and $C_{2-10}$ alkynylene, where each of $C_{1-10}$ alkylene, $C_{2-10}$ alkenylene, and $C_{2-10}$ alkynylene can be optionally interrupted by one O, S, or NH. R can be a member of the group that includes (i) hydrogen, (ii) —OR$^a$, (iii) $C_{1-4}$ alkoxy, optionally substituted with 1-3 independent units of $R^b$, (iv) $C_{1-4}$ haloalkoxy, (v) —COH, (vi) —CO$_2$R$^a$, (vii) —CONR$^a$R$^a$, (viii) cyano, (ix) —NR$^a$R$^a$, (x) —NR$^a$C(O)NR$^a$R$^a$, (xi) —NR$^a$C(O)OR$^a$, (xii) —NR$^a$C(O)R$^a$, (xiii) -aryl that is optionally substituted with 1-3 independent units of $R^b$, (xiv) -heteroaryl including from 5-10 ring atoms, where 1-4 ring atoms are each independent members of the group that includes N, NH, O, and S, and where the heteroaryl can be optionally substituted with 1-3 independent units of $R^b$, (xv) —$C_{3-10}$ cycloalkyl that is optionally substituted with 1-4 independent units of $R^b$, (xvi) -heterocyclyl, including from 3-10 ring atoms, where 1-3 of the ring atoms are independent members of the group that includes N, NH and O, and where the heterocyclyl can be optionally substituted with 1-4 independent units of $R^b$, (xvii) $C_{1-4}$ thioalkoxy, (xviii) —N$_3$, (xix) —CO$_2$H, (xx) —C(O)R$^a$, (xxi) —SO$_{1-2}$(R$^a$), and (xxii) —O$_n$P(O)$_n$Y$_2$, where each occurrence of n can independently be 0 or 1, and where each occurrence Y can independently be one of —OR$^a$, NR$^a$R$^a$, and $C_{1-6}$ alkyl. Each occurrence of R$^a$ in Formula (I) can independently be one of (i) H, (ii) $C_{1-8}$ alkyl optionally substituted with from 1-3 independent units of R$^b$, (iii) —($C_{0-6}$ alkylene)-$C_{3-10}$ cycloalkyl, where the cycloalkyl is optionally substituted with from 1-4 independent units of R$^b$, (iv) —($C_{0-6}$ alkylene)-heterocyclyl including from 3-10 ring atoms, where 1-3 of the ring atoms can each be independently members of the group that includes NH, O, and S, and where the heterocyclyl can optionally be substituted with from 1-4 independent units of R$^b$, (v) —($C_{0-6}$ alkylene)-($C_{6-10}$ aryl), where the aryl can be optionally substituted with from 1-5 independent units of R$^b$, or (vi) —($C_{0-6}$ alkylene)-heteroaryl including 5-10 ring atoms, where 1-4 of the ring atoms can each be independent members of the group that includes N, NH, O, and S, and where the heteroaryl can optionally be substituted with from 1-3 independent units of R$^b$. Each occurrence of R$^b$ in Formula (I) can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including 3-10 ring atoms, where 1-3 of the ring atoms are each independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including from 5-10 ring atoms, where 1-4 of the ring atoms can each be independent members of the group that includes N, NH, O, and S, (xiii) —S(O)$_{1-2}$($C_{1-4}$ alkyl), (xiv) —NR'R", (xv) —OH, (xvi) —S(O)$_{1-2}$(NR'R"), (xvii) —$C_{1-4}$ thioalkoxy, (xviii) —NO$_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R"). Each occurrence of R' and R" can be an independent member of the group that includes H and $C_{1-4}$ alkyl, or, if R' and R" are bonded to the same atom, R' and R" together with the atom to which each is attached can form a ring that includes from 3-8 ring atoms, and the ring can include: (a) from 1-7 ring carbon atoms; and (b) 0-3 ring heteroatoms, in addition to the atom attached to R' and R", which are each independent members of the group that includes N, NH, O, and S.

Embodiments of the methods can include any one or more of the following features.

X, R, each occurrence of R$^a$, each occurrence of R$^b$, each occurrence of R' and R", and combinations of these structural units, can have any of the features discussed in connection with Formula (I) for these structural units.

The complex can include water. The complex can include a molar ratio of lanthanide ion to complexing agent to water of 1:1:2, or 1:2:1, or 1:3:0. The lanthanide ion can be selected from the group that includes samarium, europium, terbium, and dysprosium.

Embodiments of the methods can also include any of the other features discussed, including features associated with different embodiments, in any combination unless expressly stated otherwise.

In a further aspect, this disclosure features methods of forming a complex that includes a complexing agent and a lanthanide ion, the methods including introducing the complexing agent into a subterranean reservoir at a first location, allowing the complexing agent to propagate through at least a portion of the reservoir to a second location different from the first location, extracting the complexing agent at a second location, and combining the extracted complexing agent with a solution that includes the lanthanide ion to form the complex, where the complexing agent has a general structure given by Formula (II), or an anion or salt of the structure given by Formula (II):

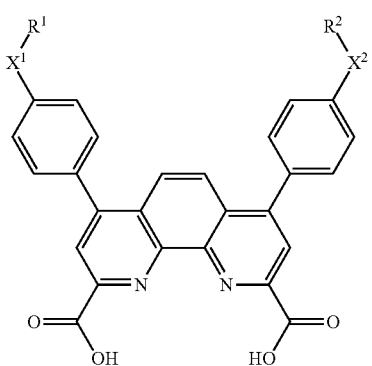

Formula (II)

In Formula (II), each of $X^1$ and $X^2$ can be independently present or absent, and when one or both are present, each can be an independent member of the group that includes $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH. Each $R^1$ and $R^2$ is an independent member of the group that includes (i) hydrogen, (ii) —$OR^a$, (iii) $C_{1-4}$ alkoxy optionally substituted with 1-3 independent units of $R^b$, (iv) $C_{1-4}$ haloalkoxy, (v) —COH, (vi) —$CO_2R^a$, (vii) —$CONR^aR^a$, (viii) cyano, (ix) —$NR^aR^a$, (x) —$NR^aC(O)NR^aR^a$, (xi) —$NR^aC(O)OR^a$, (xii) —$NR^aC(O)R^a$, (xiii) -aryl that is optionally substituted with 1-3 independent units of $R^b$, (xiv) -heteroaryl including 5-10 ring atoms, where 1-4 ring atoms are each independent members of the group that includes N, NH, O, and S, and where the heteroaryl is optionally substituted with 1-3 independent units of $R^b$, (xv) —$C_{3-10}$ cycloalkyl that is optionally substituted with 1-4 independent units of $R^b$, (xvi) -heterocyclyl including 3-10 ring atoms, where 1-3 of the ring atoms can each be independent members of the group that includes N, NH and O, where the heterocyclyl is optionally substituted with 1-4 independent units of $R^b$, (xvii) $C_{1-4}$ thioalkoxy, (xviii) —$N_3$, (xix) —$CO_2H$, (xx) —$C(O)R^a$, (xxi) —$SO_{12}(R^a)$, and (xxii) —$O_nP(O)_nY_2$, where each n is independently 0 or 1, and each Y is an independent member of the group that includes —$OR^a$, $NR^aR^a$, and $C_{1-6}$ alkyl. Each occurrence of $R^a$ can be an independent member of the group that includes (i) H, (ii) $C_{1-8}$ alkyl optionally substituted with 1-3 independent units of $R^b$, (iii) —$(C_{0-6}$ alkylene)-$C_{3-10}$ cycloalkyl, where the cycloalkyl is optionally substituted with 1-4 independent units of $R^b$, (iv) —$(C_{0-6}$ alkylene)-heterocyclyl including 3-10 ring atoms, where 1-3 of the ring atoms are independent members of the group that includes NH, O, and S, and the heterocyclyl is optionally substituted with 1-4 independent units of $R^b$, (v) —$(C_{0-6}$ alkylene)-$(C_{6-10}$ aryl), where the aryl is optionally substituted with 1-5 independent units of $R^b$, or (vi) —$(C_{0-6}$ alkylene)-heteroaryl including 5-10 ring atoms, where 1-4 of the ring atoms are independent members of the group that includes N, NH, O, and S, and the heteroaryl is optionally substituted with 1-3 independent units of $R^b$. Each occurrence of $R^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —$(C_{0-3}$ alkylene)-$C_{3-6}$ cycloalkyl optionally substituted with 1-4 independent units of $C_{1-4}$ alkyl, (x) —$(C_{0-3}$ alkylene)-heterocyclyl including from 3-10 ring atoms, where 1-3 of the ring atoms are independent members of the group that includes NH, O, and S, and where the heterocyclyl is optionally substituted with 1-4 independent units of $C_{1-4}$ alkyl, (xi) —$(C_{0-3}$ alkylene)-phenyl, (xii) —$(C_{0-3}$ alkylene)-heteroaryl including 5-10 ring atoms, where 1-4 of the ring atoms are independent members of the group that includes of N, NH, O, and S, (xiii) —$S(O)_{1-2}(C_{1-4}$ alkyl), (xiv) —NR'R", (xv) —OH, (xvi) —$S(O)_{1-2}$(NR'R"), (xvii) —$C_{1-4}$ thioalkoxy, (xviii) —$NO_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R"). Each occurrence of R' and R" can be an independent member of the group that includes H and $C_{1-4}$ alkyl, or, if R' and R" are bonded to the same atom, R' and R" together with the atom to which each is attached can form a ring including 3-8 ring atoms, where the ring includes (a) 1-7 ring carbon atoms, and (b) 0-3 ring heteroatoms (in addition to the atom attached to R' and R") which are each independent members of the group that includes N, NH, O, and S.

Embodiments of the methods can include any one or more of the following features.

$X^1$, $X^2$, $R^1$, $R^2$, each occurrence of $R^a$, each occurrence of $R^b$, each occurrence of R' and R", and combinations of these structural units, can have any of the features discussed in connection with Formula (II) for these structural units.

The complex can include water. A molar ratio of lanthanide ion to complexing agent to water can be 1:1:2 or 1:2:0. The lanthanide ion can be selected from the group that includes samarium, europium, terbium, and dysprosium.

Embodiments of the methods can also include any of the other features discussed, including features associated with different embodiments, in any combination unless expressly stated otherwise.

In another aspect, this disclosure features methods of forming a complex that includes a complexing agent and a lanthanide ion, the methods including introducing the complexing agent into a subterranean reservoir at a first location, allowing the complexing agent to propagate through at least a portion of the reservoir to a second location different from the first location, extracting the complexing agent at a second location, and combining the extracted complexing agent with a solution that includes the lanthanide ion to form the complex, where the complexing agent has a general structure given by Formula (III), or an anion or salt of the structure given by Formula (III):

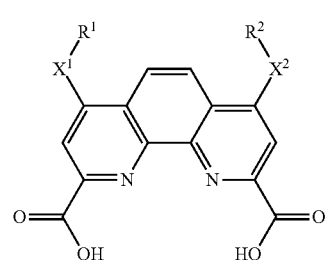

Formula (III)

In Formula (III), each of $X^1$ and $X^2$ can be independently present or absent, and when one or both are present, each can be an independent member of the group that includes $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH. Each $R^1$ and $R^2$ is an independent member of the group that includes (i) hydrogen, (ii) —$OR^a$, (iii) $C_{1-4}$ alkoxy optionally substituted with 1-3 independent units of $R^b$, (iv) $C_{1-4}$ haloalkoxy, (v) —COH, (vi) —$CO_2R^a$, (vii) —$CONR^aR^a$, (viii) cyano, (ix) —$NR^aR^a$, (x) —$NR^aC(O)NR^aR^a$, (xi) —$NR^aC(O)OR^a$, (xii) —$NR^aC(O)R^a$, (xiii) -aryl that is optionally substituted with 1-3 independent units of $R^b$, (xiv) -heteroaryl including 5-10 ring atoms, where 1-4 ring atoms are each independent members of the group that includes N, NH, O, and S, and where the heteroaryl is optionally substituted with 1-3 independent units of $R^b$, (xv) —$C_{3-10}$ cycloalkyl that is optionally substituted with 1-4 independent units of $R^b$, (xvi) -heterocyclyl including 3-10 ring atoms, where 1-3 of the ring atoms can each be independent members of the group that includes N, NH and O, where the heterocyclyl is optionally substituted with 1-4 independent units of $R^b$, (xvii) $C_{1-4}$ thioalkoxy, (xviii) —$N_3$, (xix) —$CO_2H$, (xx) —$C(O)R^a$, (xxi) —$SO_{1-2}(R^a)$, (xxii) —$O_nP(O)_nY_2$, where each n is independently 0 or 1, and (xxiii) halo (e.g., —F, —Cl, —Br, or —I), and each Y is an independent member of the group that includes —$OR^a$, $NR^aR^a$, and $C_{1-6}$ alkyl. Each occurrence of $R^a$ can be an independent member of the group that includes (i) H, (ii) $C_{1-8}$ alkyl optionally substituted with 1-3 independent units of $R^b$, (iii) —($C_{0-6}$ alkylene)-$C_{3-10}$ cycloalkyl, where the cycloalkyl is optionally substituted with 1-4 independent units of $R^b$, (iv) —($C_{0-6}$ alkylene)-heterocyclyl including 3-10 ring atoms, where 1-3 of the ring atoms are independent members of the group that includes NH, O, and S, and the heterocyclyl is optionally substituted with 1-4 independent units of $R^b$, (v) —($C_{0-6}$ alkylene)-($C_{6-10}$ aryl), where the aryl is optionally substituted with 1-5 independent units of $R^b$, or (vi) —($C_{0-6}$ alkylene)-heteroaryl including 5-10 ring atoms, where 1-4 of the ring atoms are independent members of the group that includes N, NH, O, and S, and the heteroaryl is optionally substituted with 1-3 independent units of $R^b$. Each occurrence of $R^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including from 3-10 ring atoms, where 1-3 of the ring atoms are independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including 5-10 ring atoms, where 1-4 of the ring atoms are independent members of the group that includes of N, NH, O, and S, (xiii) —$S(O)_{1-2}(C_{1-4}$ alkyl), (xiv) —NR'R", (xv) —OH, (xvi) —$S(O)_{1-2}(NR'R")$, (xvii) —$C_{1-4}$ thioalkoxy, (xviii) —$NO_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R"). Each occurrence of R' and R" can be an independent member of the group that includes H and $C_{1-4}$ alkyl, or, if R' and R" are bonded to the same atom, R' and R" together with the atom to which each is attached can form a ring including 3-8 ring atoms, where the ring includes (a) 1-7 ring carbon atoms, and (b) 0-3 ring heteroatoms (in addition to the atom attached to R' and R") which are each independent members of the group that includes N, NH, O, and S.

Embodiments of the methods can include any one or more of the following features.

$X^1$, $X^2$, $R^1$, $R^2$, each occurrence of $R^a$, each occurrence of $R^b$, each occurrence of R' and R", and combinations of these structural units, can have any of the features discussed in connection with Formula (III) for these structural units.

The complex can include water. A molar ratio of lanthanide ion to complexing agent to water can be 1:1:2 or 1:2:0. The lanthanide ion can be selected from the group that includes samarium, europium, terbium, and dysprosium.

Embodiments of the methods can also include any of the other features discussed, including features associated with different embodiments, in any combination unless expressly stated otherwise.

In a further aspect, this disclosure features complexing agents having a general structure given by Formula (I), and anions and salts of the general structure of Formula (I):

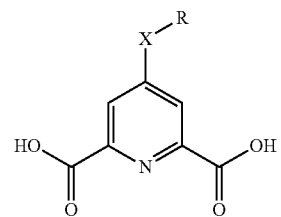

Formula (I)

In Formula (I), X can be present or absent, and when present, can be a member of the group that includes: $C_{1-10}$ alkylene, $C_{2-10}$ alkenylene, and $C_{2-10}$ alkynylene, where each of $C_{1-10}$ alkylene, $C_{2-10}$ alkenylene, and $C_{2-10}$ alkynylene can be optionally interrupted by one O, S, or NH. R can be a member of the group that includes (i) hydrogen, (ii) —$OR^a$, (iii) $C_{1-4}$ alkoxy, optionally substituted with 1-3 independent units of $R^b$, (iv) $C_{1-4}$ haloalkoxy, (v) —COH, (vi) —$CO_2R^a$, (vii) —$CONR^aR^a$, (viii) cyano, (ix) —$NR^aR^a$, (x) —$NR^aC(O)NR^aR^a$, (xi) —$NR^aC(O)OR^a$, (xii) —$NR^aC(O)R^a$, (xiii) -aryl that is optionally substituted with 1-3 independent units of $R^b$, (xiv) -heteroaryl including from 5-10 ring atoms, where 1-4 ring atoms are each independent members of the group that includes N, NH, O, and S, and where the heteroaryl can be optionally substituted with 1-3 independent units of $R^b$, (xv) —$C_{3-10}$ cycloalkyl that is optionally substituted with 1-4 independent units of $R^b$, (xvi) -heterocyclyl, including from 3-10 ring atoms, where 1-3 of the ring atoms are independent members of the group that includes N, NH and O, and where the heterocyclyl can be optionally substituted with 1-4 independent units of $R^b$, (xvii) $C_{1-4}$ thioalkoxy, (xviii) —$N_3$, (xix) —$CO_2H$, (xx) —$C(O)R^a$, (xxi) —$SO_{1-2}(R^a)$, and (xxii) —$O_nP(O)_nY_2$, where each occurrence of n can independently be 0 or 1, and where each occurrence Y can independently be one of —$OR^a$, $NR^aR^a$, and $C_{1-6}$ alkyl. Each occurrence of $R^a$ in Formula (I) can independently be one of (i) H, (ii) $C_{1-8}$ alkyl optionally substituted with from 1-3 independent units of $R^b$, (iii) —($C_{0-6}$ alkylene)-$C_{3-10}$ cycloalkyl, where the cycloalkyl is optionally substituted with from 1-4 independent units of $R^b$, (iv) —($C_{0-6}$ alkylene)-heterocyclyl including from 3-10 ring atoms, where 1-3 of the ring atoms can each be independently members of the group that includes NH, O, and S, and where the heterocyclyl can optionally be substituted with from 1-4 independent units of $R^b$, (v) —($C_{0-6}$ alkylene)-($C_{6-10}$ aryl), where the aryl can be optionally substituted with from 1-5 independent units of $R^b$, or (vi) —(C$_{0-6}$ alkylene)-heteroaryl including 5-10 ring atoms, where 1-4 of the ring atoms can each be independent members of the group that includes N, NH, O, and S, and where the heteroaryl can optionally be substituted with from 1-3 independent units of R$^b$. Each occurrence of R$^b$ in Formula (I) can be an independent member of the group that includes (i) halo, (ii) cyano, (iii) C$_{1-6}$ alkyl, (iv) C$_{2-6}$ alkenyl, (v) C$_{2-6}$ alkynyl, (vi) C$_{1-4}$ haloalkyl, (vii) C$_{1-4}$ alkoxy, (viii) C$_{1-4}$ haloalkoxy, (ix) —(C$_{0-3}$ alkylene)-C$_{3-6}$ cycloalkyl optionally substituted with 1-4 independent units of C$_{1-4}$ alkyl, (x) —(C$_{0-3}$ alkylene)-heterocyclyl including 3-10 ring atoms, where 1-3 of the ring atoms are each independent members of the group that includes NH, O, and S, and where the heterocyclyl is optionally substituted with 1-4 independent units of C$_{1-4}$ alkyl, (xi) —(C$_{0-3}$ alkylene)-phenyl, (xii) —(C$_{0-3}$ alkylene)-heteroaryl including from 5-10 ring atoms, where 1-4 of the ring atoms can each be independent members of the group that includes N, NH, O, and S, (xiii) —S(O)$_{1-2}$(C$_{1-4}$ alkyl), (xiv) —NR'R'', (xv) —OH, (xvi) —S(O)$_{1-2}$(NR'R''), (xvii) —C$_{1-4}$ thioalkoxy, (xviii) —NO$_2$, (xix) —N(R')(C(=O)C$_{1-3}$ alkyl), (xx) —C(=O)(C$_{1-4}$ alkyl), (xxi) —C(=O)O(C$_{1-4}$ alkyl), (xxii) —C(=O)OH, and (xxiii) —C(=O)N(R')(R''). Each occurrence of R' and R'' can be an independent member of the group that includes H and C$_{1-4}$ alkyl, or, if R' and R'' are bonded to the same atom, R' and R'' together with the atom to which each is attached can form a ring that includes from 3-8 ring atoms, and the ring can include: (a) from 1-7 ring carbon atoms; and (b) 0-3 ring heteroatoms, in addition to the atom attached to R' and R'', which are each independent members of the group that includes N, NH, O, and S.

Embodiments of the complexing agents can include any one or more of the following features.

X, R, each occurrence of R$^a$, each occurrence of R$^b$, each occurrence of R' and R'', and combinations of these structural units, can have any of the features discussed in connection with Formula (I) for these structural units.

Embodiments of the complexing agents can also include any of the other features discussed, including features associated with different embodiments, in any combination unless expressly stated otherwise.

In another aspect, this disclosure features complexing agents having a general structure given by Formula (II), and anions and salts of the general structure of Formula (II):

Formula (II)

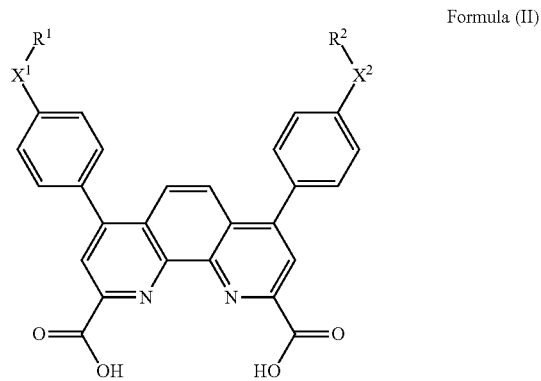

In Formula (II), each of X$^1$ and X$^2$ can be independently present or absent, and when one or both are present, each can be an independent member of the group that includes C$_{1-10}$ alkylene, C$_{2-10}$ alkenylene, and C$_{2-10}$ alkynylene, where each C$_{1-10}$ alkylene, C$_{2-10}$ alkenylene, and C$_{2-10}$ alkynylene is optionally interrupted by one O, S, or NH. Each R$^1$ and R$^2$ is an independent member of the group that includes (i) hydrogen, (ii) —OR$^a$, (iii) C$_{1-4}$ alkoxy optionally substituted with 1-3 independent units of R$^b$, (iv) C$_{1-4}$ haloalkoxy, (v) —COH, (vi) —CO$_2$R$^a$, (vii) —CONR$^a$R$^a$, (viii) cyano, (ix) —NR$^a$R$^a$, (x) —NR$^a$C(O)NR$^a$R$^a$, (xi) —NR$^a$C(O)OR$^a$, (xii) —NR$^a$C(O)R$^a$, (xiii) -aryl that is optionally substituted with 1-3 independent units of R$^b$, (xiv) -heteroaryl including 5-10 ring atoms, where 1-4 ring atoms are each independent members of the group that includes N, NH, O, and S, and where the heteroaryl is optionally substituted with 1-3 independent units of R$^b$, (xv) —C$_{3-10}$ cycloalkyl that is optionally substituted with 1-4 independent units of R$^b$, (xvi) -heterocyclyl including 3-10 ring atoms, where 1-3 of the ring atoms can each be independent members of the group that includes N, NH and O, where the heterocyclyl is optionally substituted with 1-4 independent units of R$^b$, (xvii) C$_{1-4}$ thioalkoxy, (xviii) —N$_3$, (xix) —CO$_2$H, (xx) —C(O)R$^a$, (xxi) —SO$_{12}$(R$^a$), and (xxii) —O$_n$P(O)$_n$Y$_2$, where each n is independently 0 or 1, and each Y is an independent member of the group that includes —OR$^a$, NR$^a$R$^a$, and C$_{1-6}$ alkyl. Each occurrence of R$^a$ can be an independent member of the group that includes (i) H, (ii) C$_{1-8}$ alkyl optionally substituted with 1-3 independent units of R$^b$, (iii) —(C$_{0-6}$ alkylene)-C$_{3-10}$ cycloalkyl, where the cycloalkyl is optionally substituted with 1-4 independent units of R$^b$, (iv) —(C$_{0-6}$ alkylene)-heterocyclyl including 3-10 ring atoms, where 1-3 of the ring atoms are independent members of the group that includes NH, O, and S, and the heterocyclyl is optionally substituted with 1-4 independent units of R$^b$, (v) —(C$_{0-6}$ alkylene)-(C$_{6-10}$ aryl), where the aryl is optionally substituted with 1-5 independent units of R$^b$, or (vi) —(C$_{0-6}$ alkylene)-heteroaryl including 5-10 ring atoms, where 1-4 of the ring atoms are independent members of the group that includes N, NH, O, and S, and the heteroaryl is optionally substituted with 1-3 independent units of R$^b$. Each occurrence of R$^b$ can be an independent member of the group that includes (i) halo, (ii) cyano, (iii) C$_{1-6}$ alkyl, (iv) C$_{2-6}$ alkenyl, (v) C$_{2-6}$ alkynyl, (vi) C$_{1-4}$ haloalkyl, (vii) C$_{1-4}$ alkoxy, (viii) C$_{1-4}$ haloalkoxy, (ix) —(C$_{0-3}$ alkylene)-C$_{3-6}$ cycloalkyl optionally substituted with 1-4 independent units of C$_{1-4}$ alkyl, (x) —(C$_{0-3}$ alkylene)-heterocyclyl including from 3-10 ring atoms, where 1-3 of the ring atoms are independent members of the group that includes NH, O, and S, and where the heterocyclyl is optionally substituted with 1-4 independent units of C$_{1-4}$ alkyl, (xi) —(C$_{0-3}$ alkylene)-phenyl, (xii) —(C$_{0-3}$ alkylene)-heteroaryl including 5-10 ring atoms, where 1-4 of the ring atoms are independent members of the group that includes of N, NH, O, and S, (xiii) —S(O)$_{1-2}$(C$_{1-4}$ alkyl), (xiv) —NR'R'', (xv) —OH, (xvi) —S(O)$_{1-2}$(NR'R''), (xvii) —C$_{1-4}$ thioalkoxy, (xviii) —NO$_2$, (xix) —N(R')(C(=O)C$_{1-3}$ alkyl), (xx) —C(=O)(C$_{1-4}$ alkyl), (xxi) —C(=O)O(C$_{1-4}$ alkyl), (xxii) —C(=O)OH, and (xxiii) —C(=O)N(R')(R''). Each occurrence of R' and R'' can be an independent member of the group that includes H and C$_{1-4}$ alkyl, or, if R' and R'' are bonded to the same atom, R' and R'' together with the atom to which each is attached can form a ring including 3-8 ring atoms, where the ring includes (a) 1-7 ring carbon atoms, and (b) 0-3 ring heteroatoms (in addition to the atom attached to R' and R'') which are each independent members of the group that includes N, NH, O, and S.

Embodiments of the complexing agents can include any one or more of the following features.

X$^1$, X$^2$, R$^1$, R$^2$, each occurrence of R$^a$, each occurrence of R$^b$, each occurrence of R' and R'', and combinations of these structural units, can have any of the features discussed in connection with Formula (II) for these structural units.

Embodiments of the complexing agents can also include any of the other features discussed, including features associated with different embodiments, in any combination unless expressly stated otherwise.

In a further aspect, this disclosure features complexing agents having a general structure given by Formula (III), and anions and salts of the general structure of Formula (III):

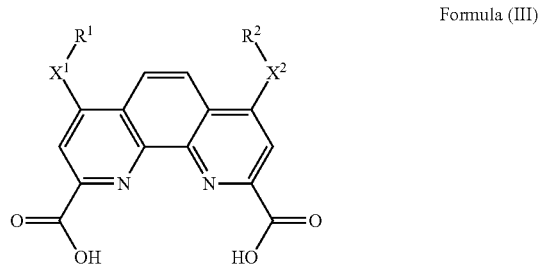

Formula (III)

In Formula (III), each of $X^1$ and $X^2$ can be independently present or absent, and when one or both are present, each can be an independent member of the group that includes $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH. Each $R^1$ and $R^2$ is an independent member of the group that includes (i) hydrogen, (ii) —$OR^a$, (iii) $C_{1-4}$ alkoxy optionally substituted with 1-3 independent units of $R^b$, (iv) $C_{1-4}$ haloalkoxy, (v) —COH, (vi) —$CO_2R^a$, (vii) —$CONR^aR^a$, (viii) cyano, (ix) —$NR^aR^a$, (x) —$NR^aC(O)NR^aR^a$, (xi) —$NR^aC(O)OR^a$, (xii) —$NR^aC(O)R^a$, (xiii) -aryl that is optionally substituted with 1-3 independent units of $R^b$, (xiv) -heteroaryl including 5-10 ring atoms, where 1-4 ring atoms are each independent members of the group that includes N, NH, O, and S, and where the heteroaryl is optionally substituted with 1-3 independent units of $R^b$, (xv) —$C_{3-10}$ cycloalkyl that is optionally substituted with 1-4 independent units of $R^b$, (xvi) -heterocyclyl including 3-10 ring atoms, where 1-3 of the ring atoms can each be independent members of the group that includes N, NH and O, where the heterocyclyl is optionally substituted with 1-4 independent units of $R^b$, (xvii) $C_{1-4}$ thioalkoxy, (xviii) —$N_3$, (xix) —$CO_2H$, (xx) —$C(O)R^a$, (xxi) —$SO_{1,2}(R^a)$, (xxii) —$O_nP(O)_nY_2$, where each n is independently 0 or 1, and (xxiii) halo (e.g., —F, —Cl, —Br, or —I), and each Y is an independent member of the group that includes —$OR^a$, $NR^aR^a$, and $C_{1-6}$ alkyl. Each occurrence of $R^a$ can be an independent member of the group that includes (i) H, (ii) $C_{1-8}$ alkyl optionally substituted with 1-3 independent units of $R^b$, (iii) —($C_{0-6}$ alkylene)-$C_{3-10}$ cycloalkyl, where the cycloalkyl is optionally substituted with 1-4 independent units of $R^b$, (iv) —($C_{0-6}$ alkylene)-heterocyclyl including 3-10 ring atoms, where 1-3 of the ring atoms are independent members of the group that includes NH, O, and S, and the heterocyclyl is optionally substituted with 1-4 independent units of $R^b$, (v) —($C_{0-6}$ alkylene)-($C_{6-10}$ aryl), where the aryl is optionally substituted with 1-5 independent units of $R^b$, or (vi) —($C_{0-6}$ alkylene)-heteroaryl including 5-10 ring atoms, where 1-4 of the ring atoms are independent members of the group that includes N, NH, O, and S, and the heteroaryl is optionally substituted with 1-3 independent units of $R^b$. Each occurrence of $R^b$ can be an independent member of the group that includes (i) halo, (ii) cyano, (iii) $C_{1-6}$ alkyl, (iv) $C_{2-6}$ alkenyl, (v) $C_{2-6}$ alkynyl, (vi) $C_{1-4}$ haloalkyl, (vii) $C_{1-4}$ alkoxy, (viii) $C_{1-4}$ haloalkoxy, (ix) —($C_{0-3}$ alkylene)-$C_{3-6}$ cycloalkyl optionally substituted with 1-4 independent units of $C_{1-4}$ alkyl, (x) —($C_{0-3}$ alkylene)-heterocyclyl including from 3-10 ring atoms, where 1-3 of the ring atoms are independent members of the group that includes NH, O, and S, and where the heterocyclyl is optionally substituted with 1-4 independent units of $C_{1-4}$ alkyl, (xi) —($C_{0-3}$ alkylene)-phenyl, (xii) —($C_{0-3}$ alkylene)-heteroaryl including 5-10 ring atoms, where 1-4 of the ring atoms are independent members of the group that includes of N, NH, O, and S, (xiii) —$S(O)_{1-2}(C_{1-4}$ alkyl), (xiv) —NR'R", (xv) —OH, (xvi) —$S(O)_{1-2}$(NR'R"), (xvii) —$C_{1-4}$ thioalkoxy, (xviii) —$NO_2$, (xix) —N(R')(C(=O)$C_{1-3}$ alkyl), (xx) —C(=O)($C_{1-4}$ alkyl), (xxi) —C(=O)O($C_{1-4}$ alkyl), (xxii) —C(=O)OH, and (xxiii) —C(=O)N(R')(R"). Each occurrence of R' and R" can be an independent member of the group that includes H and $C_{1-4}$ alkyl, or, if R' and R" are bonded to the same atom, R' and R" together with the atom to which each is attached can form a ring including 3-8 ring atoms, where the ring includes (a) 1-7 ring carbon atoms, and (b) 0-3 ring heteroatoms (in addition to the atom attached to R' and R") which are each independent members of the group that includes N, NH, O, and S.

Embodiments of the complexing agents can include any one or more of the following features.

$X^1$, $X^2$, $R^1$, $R^2$, each occurrence of $R^a$, each occurrence of $R^b$, each occurrence of R' and R", and combinations of these structural units, can have any of the features discussed in connection with Formula (III) for these structural units.

Embodiments of the complexing agents can also include any of the other features discussed, including features associated with different embodiments, in any combination unless expressly stated otherwise.

Definitions

As used throughout, the terms "about" and "approximately" are used interchangeably, and when used to refer to modify a numerical value, encompass a range of uncertainty of the numerical value of from ½ of the numerical value to twice the numerical value.

As used throughout, the singular forms "a," "an," and "the" include plural referents unless the context clearly dictates otherwise.

As used throughout, the term "distinguishing moiety" refers to a moiety bonded to the fluorescent (for example, aromatic) portion of a complexing agent that distinguishes the complexing agent on the basis of chemical structure from other complexing agents with different moieties bound to their respective fluorescent portions.

As used throughout, the terms "tracer", "cross-well tracer", and "inter-well tracer" each refer to a compound or agent (for example, a complexing agent) that is typically injected into one location of a reservoir, and then extracted from another location (that is, as part of a sample of fluid extracted from the reservoir). The presence or absence of the tracer, for example, can provide information about the connectivity between the injection and extraction locations, and the concentration of the tracer can provide information about flow capacity between the two locations.

As used throughout, the term "hydrocarbon" refers to a fluid that includes 1% or more by volume of one or more organic compounds from natural sources. For example, the one or more organic compounds can include naturally occurring compounds extracted or otherwise liberated from a subterranean reservoir. The fluid can also include other compounds such as, but not limited to, water.

The details of one or more embodiments are set forth in the accompanying drawings and the description. Other features will also be apparent from the description, drawings, and claims.

DESCRIPTION OF DRAWINGS

FIG. 15A is a plot showing recovered normalized concentration as a function of pore volume for a molecular tracer and KCl reference tracer in a limestone core.

FIG. 15B is a plot showing cumulative recovery as a function of pore volume for a molecular tracer and KCl reference tracer in a limestone core.

FIG. 16 is a schematic diagram showing injector and producer wells in an oilfield.

Like reference symbols in the various drawings indicate like elements.

DETAILED DESCRIPTION

Figure 1:
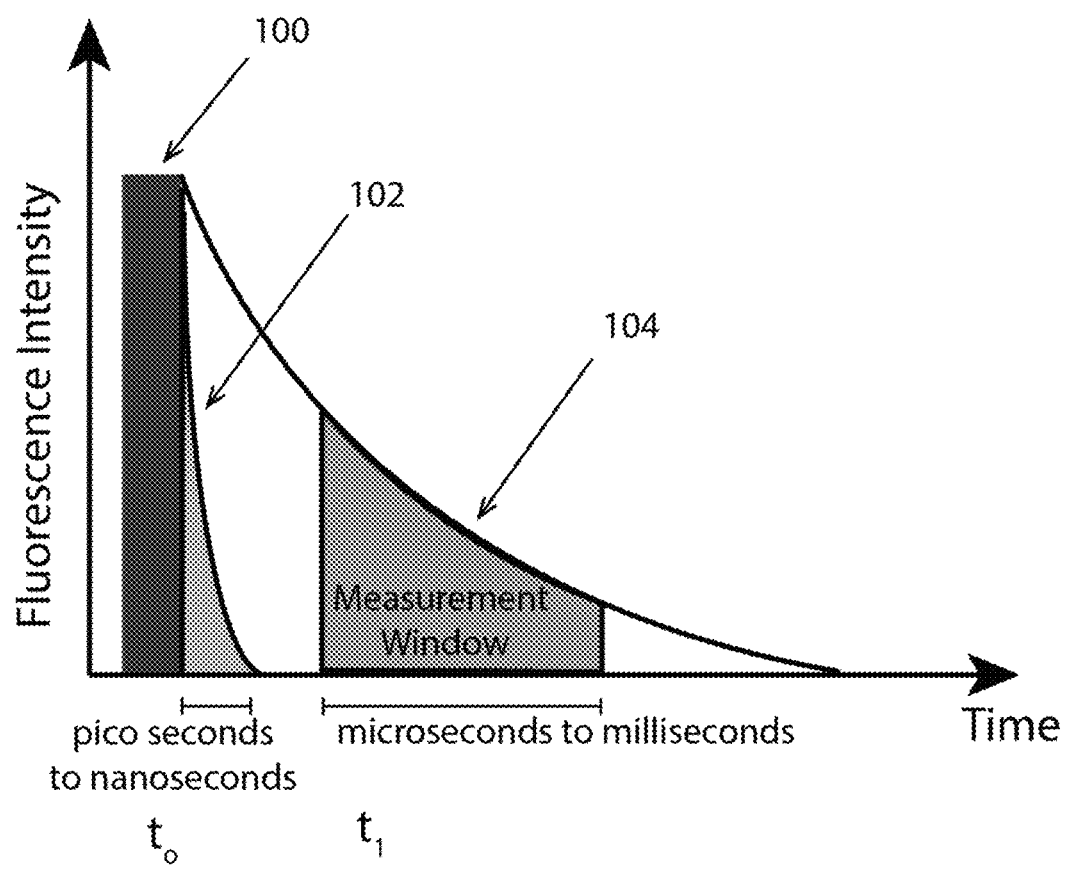
FIG. 1 is a schematic plot of time-resolved luminescence emission of components of a fluid extracted from a petroleum reservoir.

Using cross-well tracers to map the connectivity and heterogeneity of hydrocarbon reservoirs enables the identification of wells that are contributing to hydrocarbon production and fluid tracing, allowing informed adjustment of well rates to achieve a more balanced water flood. Further, for mature fields under peripheral water flooding programs that could benefit from infill drilling, implementation of a full-field cross-well tracer program that elucidates the existence of faults and greater permeability zones can greatly reduce the uncertainties for waterflood management and justify the expensive drilling/workover programs for the field.

A commonly used category of tracer is fluorinated benzoic acids (FBA's). FBA's have exhibited weak interactions with reservoir matrices and can be detected using ultra-sensitive gas chromatography mass spectrometry (GC/MS). When using GC/MS to detect FBA tracers under favorable conditions (that is, under correct ionization mode), the FBA's can be detected between 10-100 parts per trillion (ppt), depending on the fluorinated benzoic acid used and the unique response of the other components that naturally occur in produced fluids. In general, separate calibrations are used for each different analyte that undergoes mass spectral analysis.

Recent simulations have suggested that data obtained from long-term deployment of inter-well tracers may improve both history matching and production optimization in realistic reservoir models. To facilitate the collection and quantification of injected tracers in large fields, the present disclosure features families of inter-well tracers that can be detected rapidly (e.g., in real time or near-real time), that can be sampled automatically with reduced work-up relative to conventional tracers, that can be transported comparatively long distances between injection and production sites, and that exhibit reduced retention in the reservoir matrix relative to conventional tracers.

After injection at a particular location in a reservoir, the molecular tracers (also referred to as complexing agents) described are able to traverse a pathway from the injection location to a designated producing well for extraction. The tracers are designed to have relatively high solubility in fluids that naturally occur and circulate in reservoirs (for example, water or hydrocarbon compounds), and a relatively weak affinity for the various bedrock and earth formations that the tracers are exposed to while moving through the reservoir.

These features contribute to the tracers disclosed herein having a relatively high reservoir mobility. For certain tracers, having a relatively high mobility manifests as having a relatively low retention in reservoir rocks. For example, in some embodiments, the tracers disclosed herein have a retention in reservoir rocks of less than 50 micrograms per gram (μg/g) of reservoir rocks (such as less than 40 μg/g, less than 30 μg/g, less than 20 μg/g, less than 15 μg/g, less than 10 μg/g, less than 5 μg/g, less than 2 μg/g, less than 1 μg/g).

Without wishing to be bound by theory, it is believed that the various structural features of the tracers may be responsible for the relatively high reservoir fluid solubility and relatively low earth retention characteristics of the tracers. This may be due, for example, to the combination of polar functional groups and lipophilic aromatic groups present in some embodiments of the tracers. The relatively high mobility of the tracers will later be demonstrated and discussed in the context of mobility experiments that simulate the conditions that the tracers encounter in reservoirs.

The tracers, after recovery from a producing well, are optically detectable in the produced fluid at parts per quadrillion concentrations or less after a facile and selective complex formation step with trivalent lanthanide elements, and with minimal background signal due to other contaminants. Not wishing to be bound by theory, it is believed that when used as inter-well tracers, the disclosed complexing agents encounter reservoir fluids with excess naturally-occurring divalent and trivalent ions. Such divalent and trivalent ions may bind with lanthanide ions competitively, generating complexes that may also fluoresce, thus contributing to the fluorescence background. The fluorescence background may also contain, for example, contributions due to polyaromatic hydrocarbons (PAH's).

FIG. 1 is a schematic plot of time-resolved fluorescence and luminescence emission of components of a fluid extracted from a petroleum reservoir, after exposure to trivalent lanthanide elements. After flash excitation 100, which ends at a time $t_0$, the lanthanide complexes formed between the tracers and lanthanide elements have a long excited state lifetime 104, luminescing on a time scale of milliseconds (ms) to microseconds (μs). In some embodiments, the complex's luminescence occurs for a time period greater than 5 microseconds (for example, greater than 8 μs, greater than 10 μs, greater than 15 μs, greater than 20 μs, greater than 25 μs, greater than 30 μs, greater than 35 μs, greater than 40 μs, greater than 50 μs, greater than 100 μs, greater than 200 μs, greater than 300 μs, greater than 500 μs, greater than 700 μs, greater than 1 millisecond (ms), greater than 2 ms, greater than 5 ms, greater than 10 ms) after excitation is complete.

Without wishing to be bound by theory, the long excited state lifetime occurs due to parity-forbidden transitions between lanthanide ion excited and ground states, which occur significantly more slowly than parity-allowed state-to-state transitions during excitation and further, significantly more slowly than background fluorescence arising from parity allowed excited-to-ground state transitions among other components of the reservoir fluid. When a lanthanide ion is in close proximity to a sensitizing chromophore that either has a strong dipole moment or is anionic such that is can associate ionically with the lanthanide ion, significant enhancement of the lanthanide ion luminescence occurs because the sensitization process circumvents the LaPorte selection rules that normally forbid f-f transitions.

This difference in time scales separates the luminescence signal of the lanthanide complex from the background fluorescent signals 102, which are emitted from the other components (which, in some embodiments, are contaminants) found in the extracted fluid, and become undetectable at a time $t_1$. In turn, the difference in excited state lifetimes and concomitant difference in the temporal evolution of emission from the lanthanide complexes and background components allows gating of the optical detector such that the detector can be used to measure luminescence from the complex alone, after fluorescence from background components in the extracted fluid has decayed.

Figure 2A:
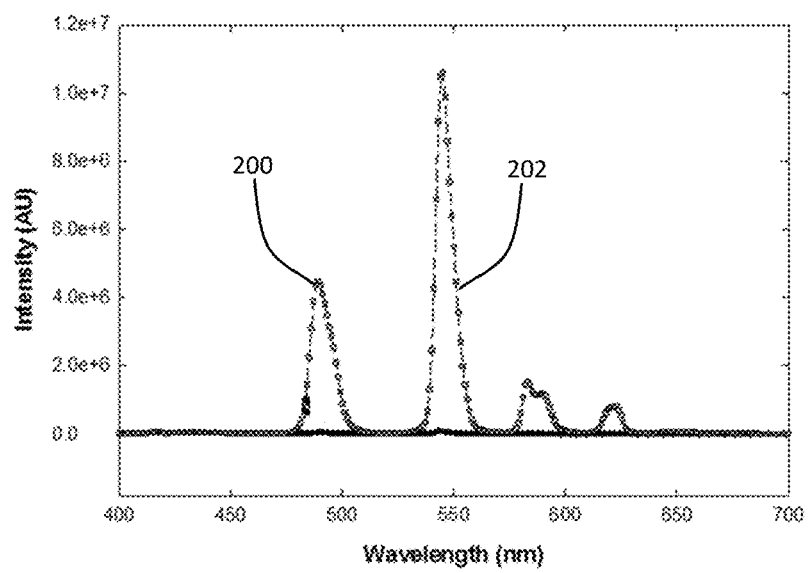
FIG. 2A is a luminescence spectrum of a complexed lanthanide ion and a bare lanthanide ion.
Figure 2B:
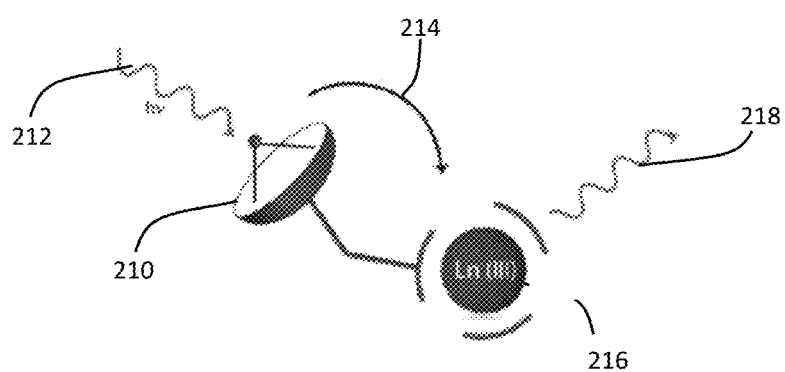
FIG. 2B is a schematic diagram showing absorption of incident light and luminescence emission from a complexed lanthanide ion.

In addition to reducing or eliminating confounding effects of background fluorescence, the relatively greater sensitivity that can be achieved when measuring the disclosed tracers is in part due to the relatively strong luminescence emission of the complexes. FIG. 2A is a luminescence spectrum of a complexed lanthanide ion and a bare lanthanide ion. The bare lanthanide ion has a peak 200 that is of lesser intensity than the intensity of the complexed lanthanide ion peak 202. FIG. 2B is a schematic diagram showing absorption of incident light and luminescence emission from a complexed lanthanide ion. The greater quantum yield of luminescence from the lanthanide complex is due to the antenna-like function of the fluorophoric complexing agent 210, which absorbs incident light 212. The ligand then transfers this excitation by process 214 to the lanthanide ion 216, which then emits fluorescence 218. In effect, the ligand functions as an energy harvester to, for example, overcome the lesser magnitude molar absorptivities of lanthanide ions and bypass the selection rules associated with transitions to the luminescent lanthanide excited state, thus increasing the quantum yield of the luminescence process.

As a result, luminescence can be enhanced by, for example, three orders of magnitude relative to a bare lanthanide ion. The luminescence intensities of lanthanide ions can be enhanced to this degree by exposing the ions to a molar excess of tracer (also referred to as complexing agent) relative to the ion. It is believed that this results in the exclusion of water molecules from the formed complex, thus maximizing the number of complexing ligands included in the complex.

Another feature of the disclosed tracers is the ability to derivatize the tracers with functional groups (also referred to as "distinguishing moieties") to generate analogs. Each of several of these analogs can be injected at a different injection location in a reservoir. After extracting a fluid from a producing well, the various analogs can be separated by virtue of their different chemical identities. The resulting purified tracers form complexes with lanthanide ions and are detected via luminescence emission. Since the light-capturing portion of each tracer is the same, each complex will luminesce with similar intensity, and over a similar temporal window. This allows for information to be gathered on multiple flow paths extending between different injection sites and a common recovery site.

Analyzing a Fluid Extracted from a Reservoir

Figure 10:
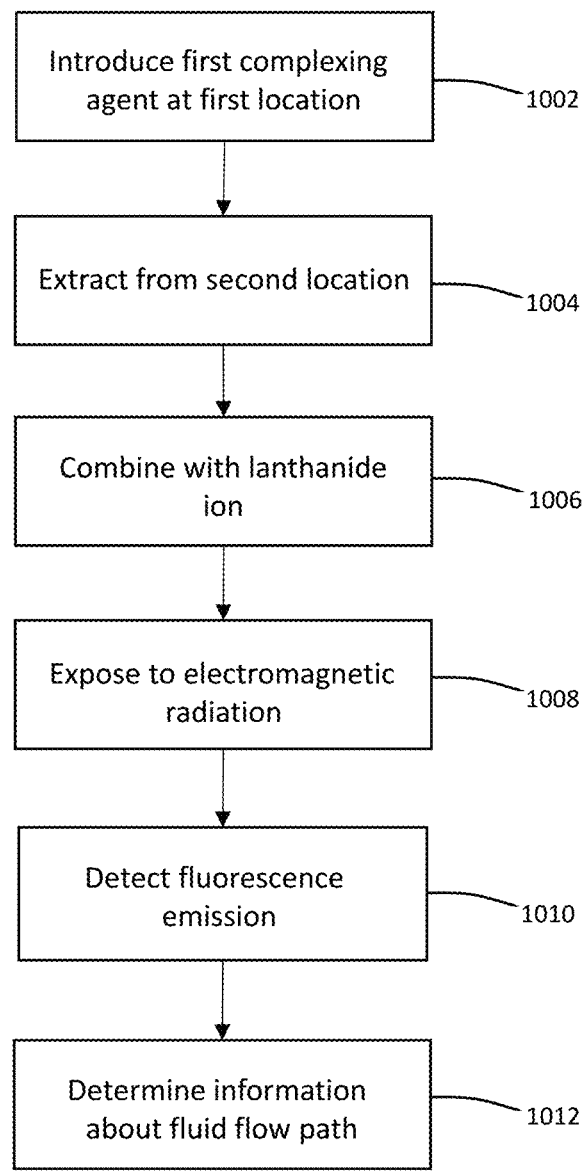
FIG. 10 is a flowchart showing example steps for a method of analyzing a fluid that includes a complexing agent extracted from a reservoir.

FIG. 10 is a flowchart showing a series of example steps for a method of analyzing a fluid extracted from a reservoir. In step 1002, a first composition including a first complexing agent is introduced into a reservoir at a first location. In some embodiments, the first location is an injection well.

In step 1004, a fluid is extracted from the reservoir at a second location different from the first location, the fluid including a concentration of the first complexing agent that is present in the fluid following injection at the first location in step 1002. The fluid may also include materials and compounds typically found in the earth's crust, for example: water, heavy metals (for example, iron, manganese, chromium, vanadium, or zirconium), salts (for example, potassium salts, calcium salts, magnesium salts, or sodium salts (for example, sodium chloride)), naturally occurring radioactive material (for example, uranium, thorium, radium, or radon), zinc, lead, sulfur, barium, or any combination of the previously listed components. In some embodiments, the fluid includes hydrocarbons (for example, hydrocarbons derived from various forms of petroleum including, but not limited to, paraffinic petroleum, paraffinic-naphthenic petroleum, naphthenic petroleum, paraffinic-naphthenic-aromatic petroleum, and aromatic petroleum) and polyaromatic hydrocarbons. In some embodiments, a separation of the complexing agent from one or more of the other components in the fluid is performed, for example to reduce or eliminate spectral contributions from the other components (that is, "background noise") during measurement, a discussion of which is forthcoming.

In step 1006, the extracted fluid (or a separated/purified portion of the fluid) is combined with a second composition including a concentration of a lanthanide ion to form a third composition that includes a concentration of a complex formed by the first complexing agent and the lanthanide ion. As previously discussed, a separation of the complex that is formed from one or more of the other components in the third composition can optionally be performed at this stage to purify the complex prior to subsequent detection.

In step 1008, a quantity of the third composition (or a purified solution derived from the third composition) is exposed to electromagnetic radiation to detect (and, in some embodiments, quantitatively measure) the complex. In some embodiments, the wavelength of the exciting electromagnetic radiation is in the ultraviolet region of the spectrum.

In general, exposure to the illumination radiation occurs for a first time period ending at a time $t_0$. As explained previously, background components in the third composition undergo fluorescence from time $t_0$ (which is defined as the time point at which the excitation process has ended) until a later time $t_1$ (which is defined as the time point at which fluorescence from the background components has decayed to an intensity level that is no longer detectable).

In step 1010, luminescence emission is detected from the irradiated complex, beginning at time $t_1 > t_0$. In general, the interval $t_1 - t_0$ is selected to ensure that the measured luminescence emission from the irradiated complex is not contaminated with significant contributions from background components (that is, other components present in the third composition). In some embodiments, for example, the interval $t_1 - t_0$ is greater than 2 microseconds (for example, greater than 5 microseconds, greater than 8 μs, greater than 10 μs, greater than 15 μs, greater than 20 μs, greater than 25 μs, greater than 30 μs, greater than 35 μs, greater than 40 μs, greater than 50 μs, or greater than 100 μs).

In step 1012, information is determined about fluid flow between the first location (the injection site) and the second location (the extraction site) within the reservoir based on the detected luminescence emission. The information can indicate, for example, whether a particular injection bore and extraction bore are interconnected through the reservoir, and, if connected, can also indicate how fluid flows through the reservoir.

For example, if a tracer is introduced into a reservoir and subsequent sample extraction from a producing bore shows the presence of the tracer, a connection exists between the point of injection and the point of extraction.

Correlations between the presence of the tracer in the extracted fluid and the elapsed time between injection and detection of the tracer can also provide information about fluid flow through the reservoir. As an example, the elapsed time between injection and the appearance of the tracer in the extracted fluid (for example, in a measurement process where fluid is extracted periodically and analyzed) can provide information about the fluid flow capacity of the reservoir, the interconnected-ness of flow pathways, and residual oil saturation, which is difficult to acquire directly by other means.

In some embodiments, the information includes the concentration of the first complexing agent. Due to the enhancement of luminescence of the complexes and reduction or elimination of background fluorescence, as discussed previously, a minimum concentration of the first complexing agent in the third composition (formed in step 1006) that can be detected is between about 1 part per million and about 1 part per sextillion (for example, about 1 part per million and about 299 parts per billion, about 300 parts per billion (ppb) and about 1.1 parts per billion (ppb), about 1 part per billion (ppb) and about 499 parts per quadrillion (ppq), about 500 parts per quadrillion and about 1.1 parts per quadrillion, about 1 part per quadrillion (ppb) and about 499 parts per quintillion (ppq), about 500 parts per quintillion and about 1.1 parts per quintillion, about 1 part per quintillion and about 499 parts per sextillion, about 500 parts per sextillion and about 1 part per sextillion).

Figure 4:
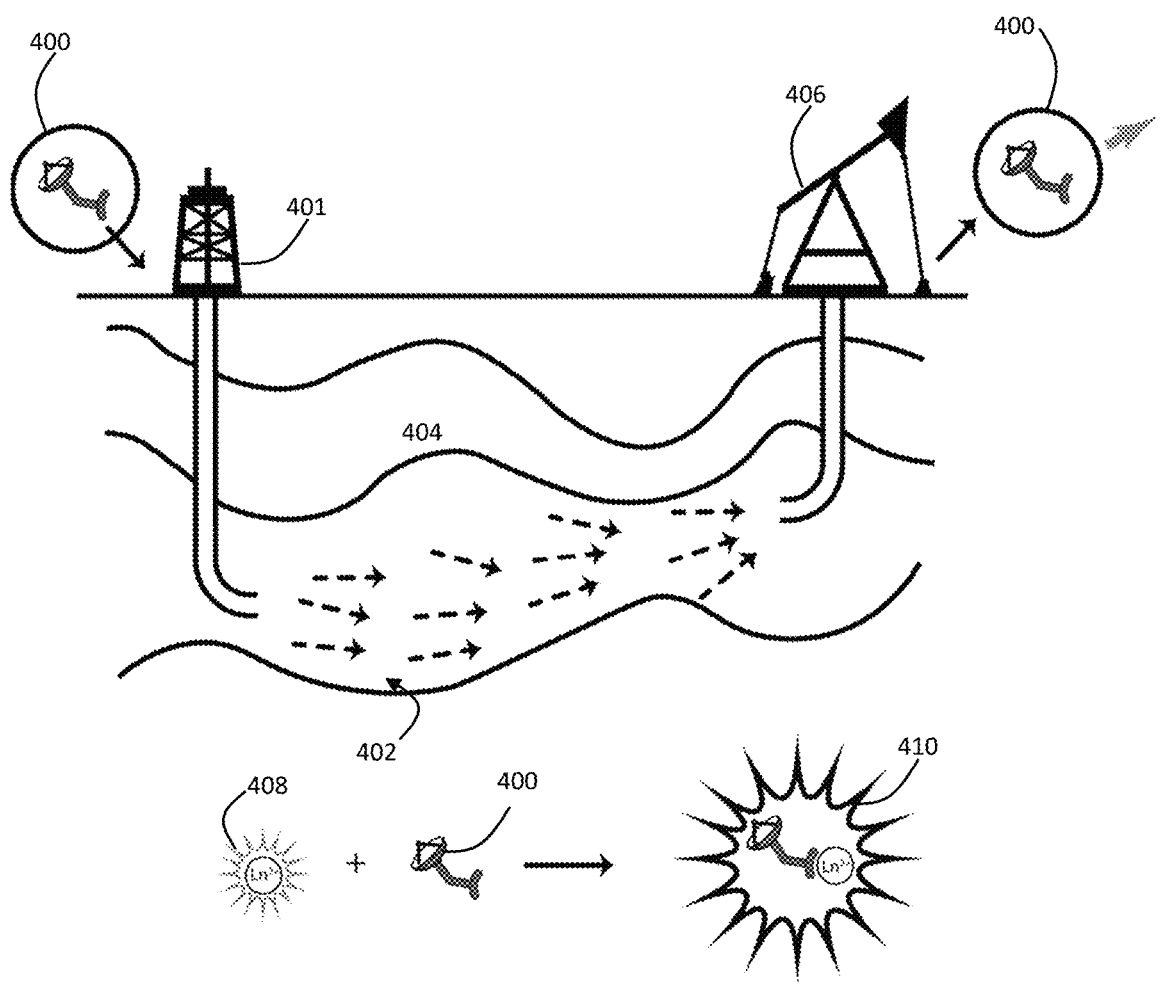
FIG. 4 is a schematic diagram showing a process for the use of a complexing agent as a cross-well tracer, and subsequent complex formation.

FIG. 4 is a schematic diagram showing an example of a process for the use of a complexing agent as a cross-well tracer. The complexing agent 400 is introduced into the reservoir 404 through an injection bore at a first location 401, and propagates through at least a portion of the reservoir 402. A fluid sample is collected from a producing bore at a second location 406 different from the first location 401. The fluid sample, which includes the complexing agent, is mixed with a solution 408 containing a specific concentration of one or more lanthanide ions (which, when bare or uncomplexed, have low fluorescence intensities), resulting in the formation of one or more types of complexes 410.

In general, it is possible to use more than one (for example, 2, 3, 4, 5, from 6 to 10, from 11 to 20, from 21 to 50, or from 51 to 100) complexing agents in the disclosed methods, for example to determine information about flow paths between multiple injection locations and an extraction location of a reservoir.

Figure 11:
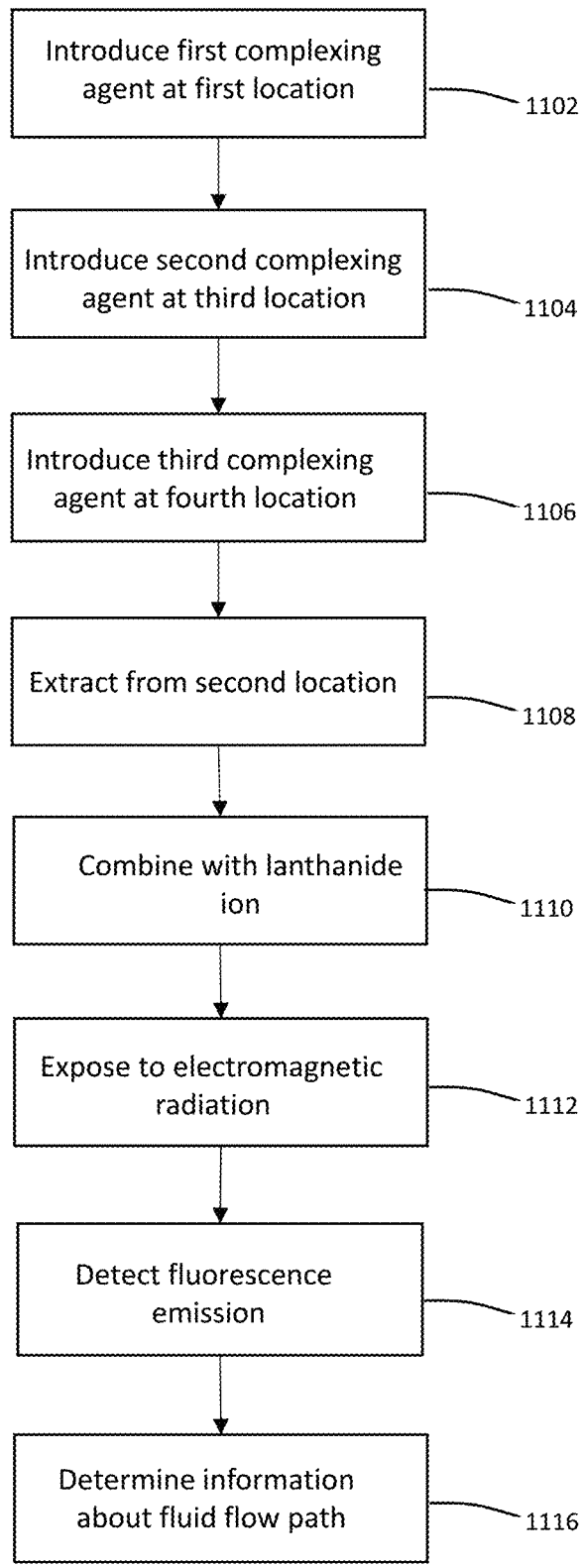
FIG. 11 is a flowchart showing example steps for a method of analyzing a fluid that includes three complexing agents extracted from a reservoir.

FIG. 11 is a flowchart showing a series of example steps of a procedure for analyzing a fluid extracted from a reservoir. In the procedure shown in FIG. 11, multiple complexing agents, each including a different distinguishing moiety, are introduced into the reservoir at different injection sites. Deployment of multiple complexing agents, each injected at a different location into a reservoir, allows determination of information about flow paths (such as flow rates) between each injection site and the extraction site. In general, unless expressly stated otherwise, the features and aspects of the method of FIG. 11 are similar to those already discussed in connection with FIG. 10.

In FIG. 11, a first composition that includes a first complexing agent is introduced into a reservoir at a first location in step 1102. Similarly, in steps 1104 and 1106, fourth and fifth compositions (which include a second complexing agent and a third complexing agent, respectively, with the designations of these being consistent with the designations previously discussed in connection with FIG. 10) are introduced into the reservoir at third and fourth locations, respectively. The fourth composition includes a second complexing agent, and the fifth composition includes a third complexing agent. Each of the first, third, and fourth locations are different.

Although not shown in FIG. 11, the procedure can also include introducing additional compositions into the reservoir at additional locations. In general, any number of compositions can be introduced. For example, the number of compositions that are introduced can be three or more (e.g., five or more, ten or more, 15 or more, 20 or more, or more, 40 or more, 50 or more, 70 or more, 100 or more, 150 or more, 200 or more, or even more).

Typically, at each location, the complexing agent introduced differs from the complexing agents introduced at the other locations so that information specific to the flow path between that location and the extraction location can be determined. Each of the complexing agents that are introduced can correspond to one of the complexing agents discussed in a subsequent section.

Further, in some embodiments, step 1106 is omitted and the resulting method includes the introduction of only the first and second complexing agents, with subsequent steps excluding the processing and presence of the third complexing agent.

In step 1108, a fluid is extracted from the reservoir at a second location that differs from each of the locations where the various compositions were introduced into the reservoir. The extracted fluid generally includes a quantity (that is, a concentration) of each of the first, second, and third complexing agents. Optionally, a separation procedure can be performed on the extracted fluid to isolate portions of the first, second, and third complexing agents from one another to facilitate analysis of the complexing agents.

Figure 19:
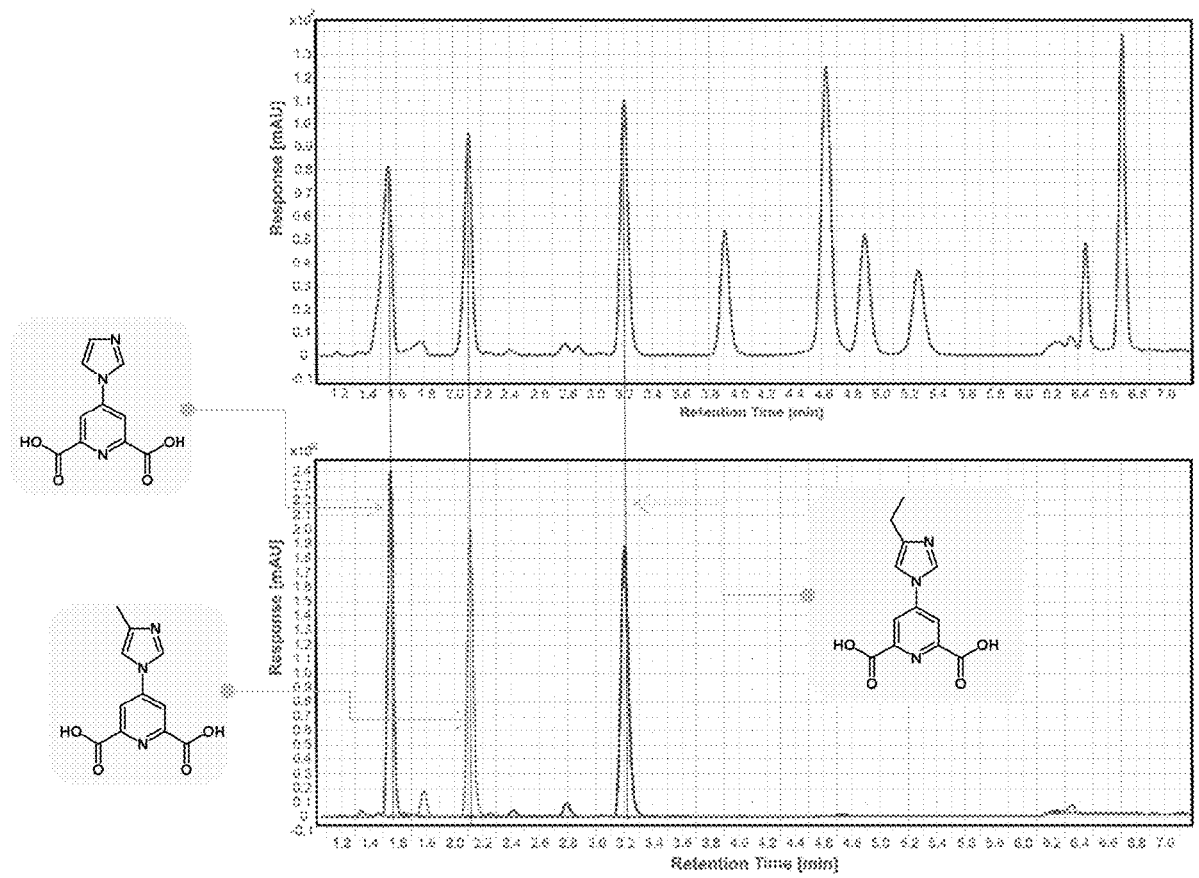
FIG. 19 is a set of plots showing liquid chromatograms for nine different molecular tracers.
Figure 19:
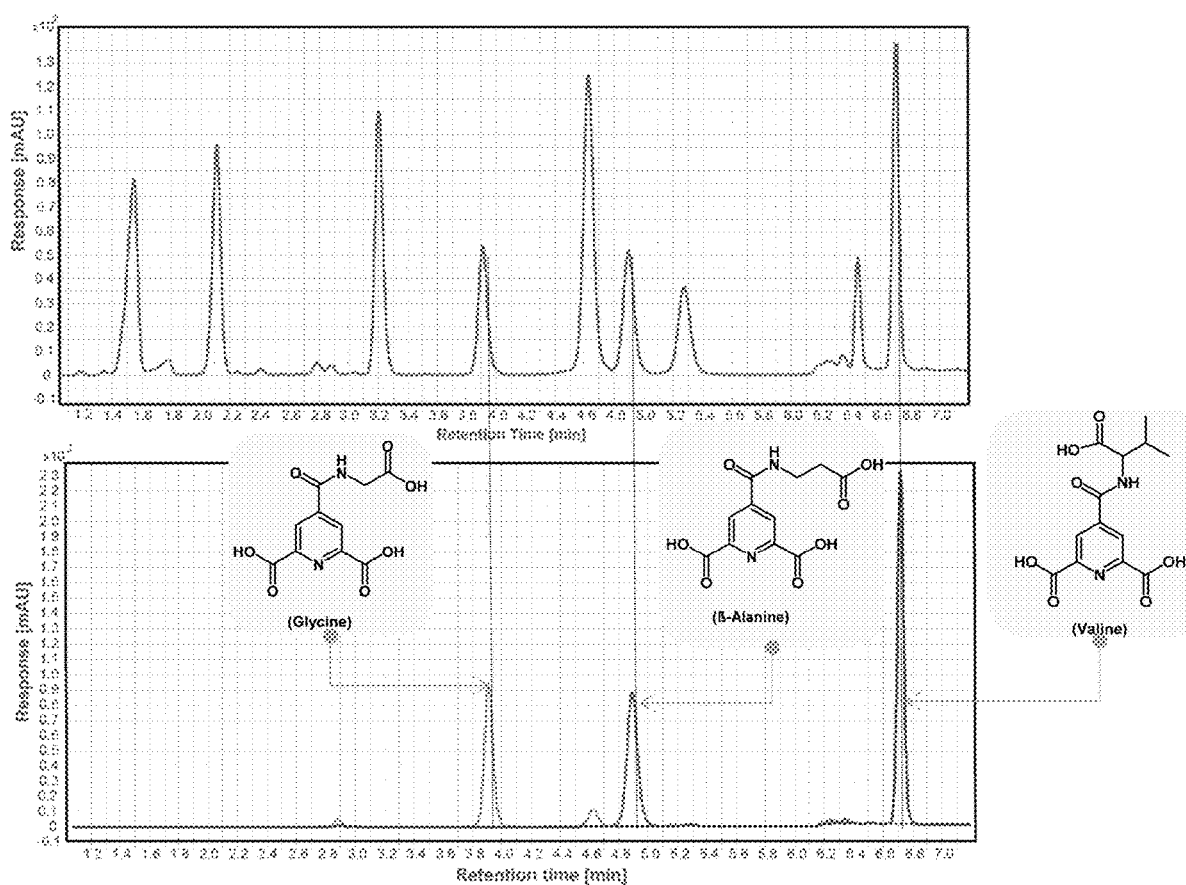
Figure 19:
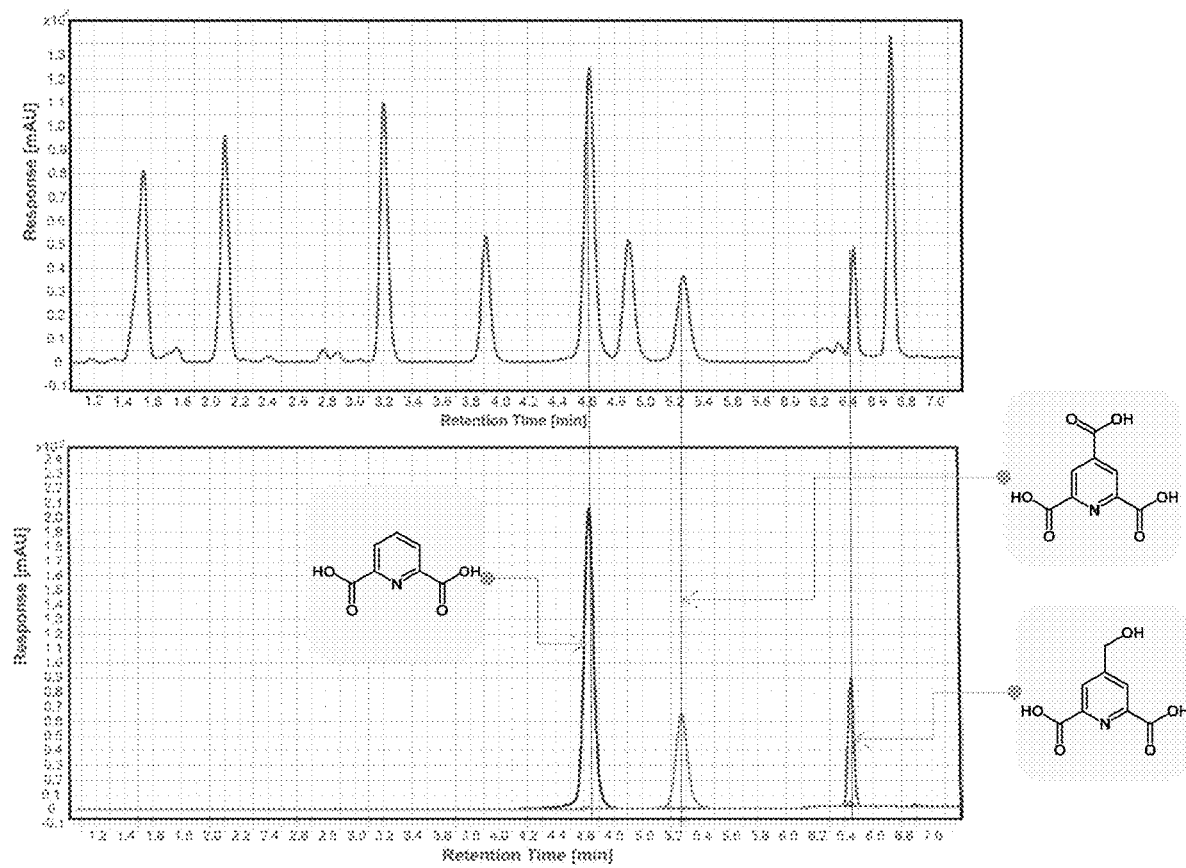

Suitable separation procedures for isolating the different complexing agents include, but are not limited to, chromatographic separation techniques such as liquid chromatography and gas chromatography. In general, these techniques can isolate a relative large number of different complexing agents from an initial mixture. For example, FIG. 19 shows liquid chromatographic traces for nine different complexing agents, each of which elutes from the chromatography column at a different retention time (and is therefore separated from the other complexing agents).

In step 1110, the extracted fluid (or the complexing agents isolated from the extracted fluid) is (are) combined with a second composition that includes a concentration of one or more types of lanthanide ions to form a third composition. In general, complexes are formed between each of the complexing agents present in the extracted fluid and the one or more types of lanthanide ions. Following formation of the different types of complexes (for example, complexes involving lanthanide ions and each of the first, second, and third complexing agents), a separation procedure is typically performed to isolate quantities of the various types of complexes. Each type of complex formed acts, in effect, as a "reporter" for fluid flow information within the reservoir between the injection site of the corresponding complexing agent and the extraction site. A variety of different separation procedures can be used in step 1110, including (but not limited to) chromatographic methods (for example, liquid chromatography), extraction, and fractionation.

In step 1112, each of the isolated quantities of the various complexes are exposed to electromagnetic radiation for a time period ending at time $t_0$ to induce luminescence emission from each of the complexes. The luminescence emission is detected in step 1114 starting at time $t_1 > t_0$, following the end of the illumination. As discussed previously, the interval $t_1 - t_0$ is selected so that at time $t_1$, fluorescence emission from background components has decayed to a nearly (or completely) undetectable level, such that measurement of luminescence emission from each of the complexes occurs without confounding spectral contributions from background components. As in the methods of FIG. 10, in some embodiments, the interval $t_1 - t_0$ can be greater than 2 microseconds.

In step 1116, information is determined about fluid flow paths between the various injection sites of the complexing agents (the first, third, and fourth locations) and the extraction site (the second location) from the measured luminescence of each of the complexes formed from complexing agents recovered at the extraction site. As discussed previously in connection with FIG. 10, this information can include concentrations of each of the complexes (or complexing agents) recovered at the extraction site, flow rates between the various injection sites and the extraction site, and other information about the reservoir structure.

Figure 12:
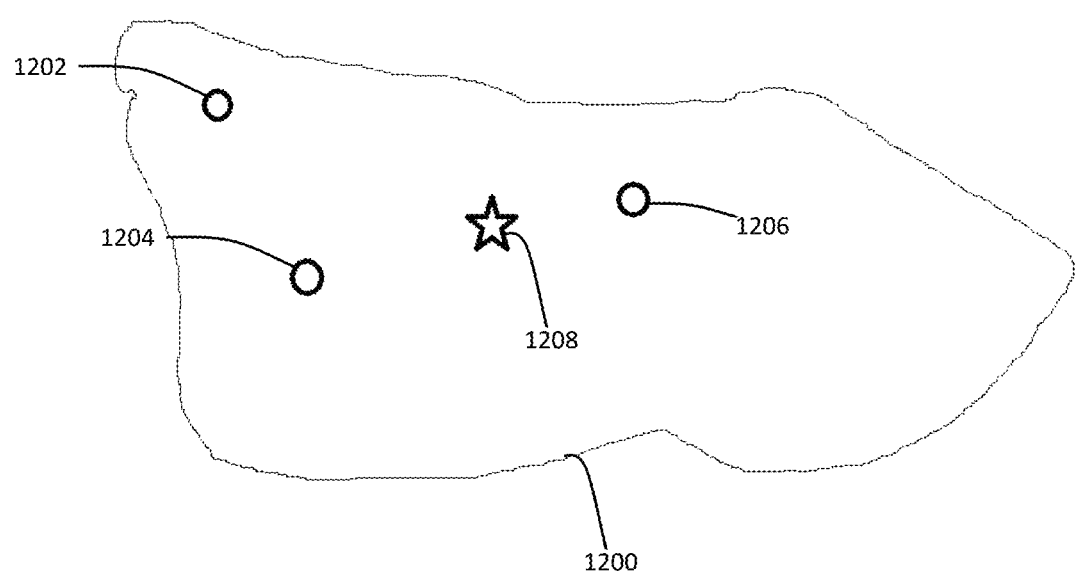
FIG. 12 is a schematic diagram showing a process for the use of several complexing agents as cross-well tracers.

FIG. 12 is a schematic diagram showing an example of a process for the use of several complexing agents as cross-well tracers as discussed previously in connection with FIG. 11. In FIG. 12, a first complexing agent is introduced into a reservoir 1200 at a location 1202, a second complexing agent is introduced into the reservoir at location 1204, and a third complexing agent is introduced into the reservoir at location 1206. Reservoir fluid is extracted at location 1208, the fluid generally including concentrations of the first, second, and third complexing agents, which have propagated from their respective injection locations through the reservoir to location 1208. The extracted reservoir fluid is then analyzed as discussed previously.

Figure 5:
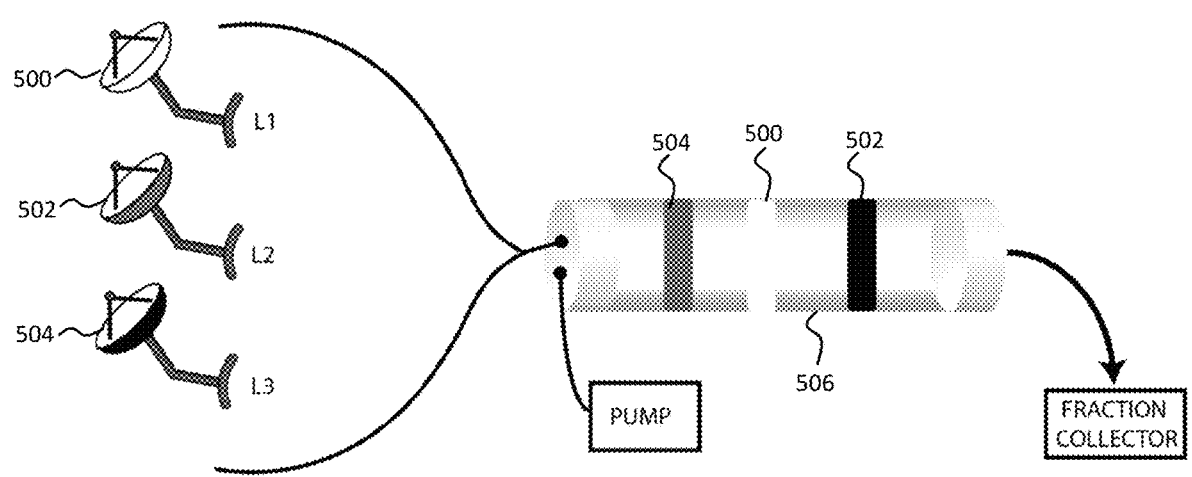
FIG. 5 is a schematic diagram showing a process for recovery, purification, and analysis of three different complexing agents.

To purify the extracted reservoir fluid from location 1208, the example process shown in FIG. 5 can be used, as the process is generally applicable to the purification and analysis of any number of complexing agents. When the extracted fluid includes concentrations of the first complexing agent 500, the second complexing agent 502, and the third complexing agent 504, the process of FIG. 5 is used to isolate quantities of each of the complexing agents. Various separation procedures can be used to isolate the complexing agents. For example, in some embodiments, liquid chromatographic methods (such as ultra-high performance liquid chromatography, high-performance liquid chromatography) can be performed using one or more chromatography columns 506 to separate the complexing agents. In certain embodiments, other methods can be used in addition to, or as an alternative to, chromatographic separations. Examples of such methods include solid phase extraction, liquid-liquid extraction and fractionation.

Each complexing agent, now substantially isolated from the other complexing agents, is then combined with a composition that includes lanthanide ions to form complexes, and fluorescence/luminescence spectroscopy methods are used to detect and, in some embodiments, determine quantitative information about the complexes.

Complexing Agents

A variety of different complexing agents can be used as molecular tracers to determine information associated with petroleum reservoirs according to the methods that have been discussed. In this section of the disclosure, various example complexing agents are described. It should be understood that any of the complexing agents discussed in this section can be used alone or in combination with any of the methods discussed in the previous sections of this disclosure to determine information about subsurface reservoirs and fluid flow through the reservoirs. In particular, any of the first, second, and third complexing agents referenced previously can be selected from among the various compounds corresponding to Formula (I), Formula (II), Formula (III), or any combination of these, as will be explained in detail.

Figure 3:
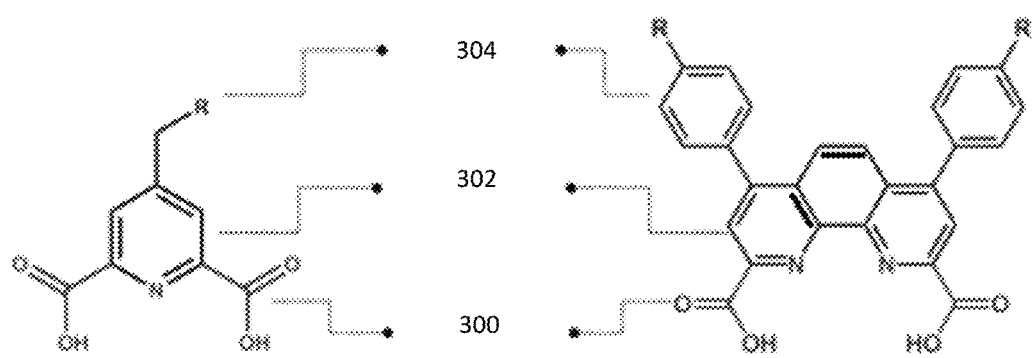
FIG. 3 is a schematic diagram showing examples of two complexing agent structures.

FIG. 3 is a schematic diagram showing examples of two complexing agent structures. The structures of the complexing agents are designed to have three features, shown for two different structures: (1) lanthanide binding group(s) 300 that are capable of chelating lanthanide ions with large equilibrium constants, (2) a light-absorbing region 302 with large extinction coefficient capable of absorbing excitation light efficiently, and (3) derivatizable molecular "handles" 304 that allow for installation of different moieties to generate analogs that can each be deployed at a unique location in a reservoir. The complexing agents are monodentate, bidentate, tridentate, or tetradentate ligands that bind to lanthanides through, for example, basic ring member nitrogens, carboxylate groups, or both.

In some embodiments, the complexing agent is a compound of Formula (I), or an anion or salt thereof:

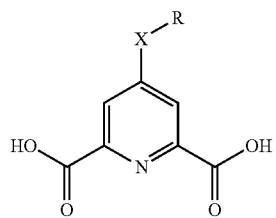

Formula (I)

where:
X is present or absent, and when present, is selected from the group consisting of: $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH;

R is selected from the group consisting of:
(i) hydrogen;
(ii) —$OR^a$;
(iii) $C_{1-4}$ alkoxy optionally substituted with from 1-3$R^b$;
(iv) $C_{1-4}$ haloalkoxy;
(v) —COH;
(vi) —$CO_2R^a$;
(vii) —$CONR^aR^a$;
(viii) cyano;
(ix) —$NR^aR^a$;
(x) —$NR^aC(O)NR^aR^a$;
(xi) —$NR^aC(O)OR^a$;
(xii) —$NR^aC(O)R^a$;
(xiii) -aryl that is optionally substituted with from 1-3$R^b$;
(xiv) -heteroaryl including from 5-10 ring atoms, where from 1-4 ring atoms are each independently selected from the group consisting of N, NH, O, and S, where the heteroaryl is optionally substituted with from 1-3$R^b$;
(xv) —$C_{3-10}$ cycloalkyl that is optionally substituted with from 1-4$R^b$,
(xvi) -heterocyclyl including from 3-10 ring atoms, where from 1-3 ring atoms are each independently selected from the group consisting of N, NH and O, where the heterocyclyl is optionally substituted with from 1-4$R^b$,
(xvii) $C_{1-4}$ thioalkoxy;
(xviii) —$N_3$;
(xix) —$CO_2H$;
(xx) —$C(O)R^a$;
(xxi) —$SO_{1-2}(R^a)$; and
(xxii) —$O_nP(O)_nY_2$, where n is independently 0 or 1, and where Y is independently selected from —$OR^a$, $NR^aR^a$, and $C_{1-6}$ alkyl;

each occurrence of $R^a$ is independently selected from the group consisting of:
(i) H;
(ii) $C_{1-8}$ alkyl optionally substituted with from 1-3 independently selected $R^b$;
(iii) —($C_{0-6}$ alkylene)-$C_{3-10}$ cycloalkyl, where the cycloalkyl is optionally substituted with from 1-4 independently selected $R^b$;
(iv) —($C_{0-6}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $R^b$;
(v) —($C_{0-6}$ alkylene)-($C_{6-10}$ aryl), where the aryl is optionally substituted with from 1-5 independently selected $R^b$; or
(vi) —($C_{0-6}$ alkylene)-heteroaryl including from 5-10 ring atoms, where from 1-4 ring atoms are each independently selected from the group consisting of N, NH, O, and S, where the heteroaryl is optionally substituted with from 1-3 independently selected $R^b$;

each occurrence of $R^b$ is independently selected from the group consisting of:
(i) halo;
(ii) cyano;
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $C_{1-4}$ alkyl;
(xi) —($C_{0-3}$ alkylene)-phenyl;
(xii) —($C_{0-3}$ alkylene)-heteroaryl including from 5-10 ring atoms, where from 1-4 ring atoms are each independently selected from the group consisting of N, NH, O, and S;
(xiii) —$S(O)_{1-2}(C_{1-4}$ alkyl); and
(xiv) —NR'R";
(xv) —OH;
(xvi) —$S(O)_{1-2}$(NR'R");
(xvii) $C_{1-4}$ thioalkoxy;
(xviii) —$NO_2$;
(xix) —N(R')(C(=O)$C_{1-3}$ alkyl);
(xx) —C(=O)($C_{1-4}$ alkyl);
(xxi) —C(=O)O($C_{1-4}$ alkyl);
(xxii) —C(=O)OH, and
(xxiii) —C(=O)N(R')(R");

each occurrence of R' and R" is independently selected from the group consisting of: H and $C_{1-4}$ alkyl; or, if R' and R" are bonded to the same atom, R' and R" together with the atom to which each is attached forms a ring including from 3-8 ring atoms, where the ring includes: (a) from 1-7 ring carbon atoms; and (b) from 0-3 ring heteroatoms (in addition to the atom attached to R' and R"), which are each independently selected from the group consisting of N, NH, O, and S.

In some embodiments,
X is $C_{1-10}$ alkylene;
R is selected from the group consisting of:
(ii) —$OR^a$; where the $R^a$ of —$OR^a$ is not (i) H or (ii) $C_{1-8}$ alkyl substituted with —($C_{0-3}$ alkylene)-$C_{3-6}$ cycloalkyl;

(vi) —CO₂Rᵃ, where the Rᵃ of —CO₂Rᵃ is not H;
(viii) cyano;
(ix) —NRᵃRᵃ;
(x) —NRᵃC(O)NRᵃRᵃ;
(xi) —NRᵃC(O)ORᵃ;
(xii) —NRᵃC(O)Rᵃ;
(xiii) -aryl that is optionally substituted with from 1-3R$^b$;
(xiv) -heteroaryl including from 5-10 ring atoms, where from 1-4 ring atoms are each independently selected from the group consisting of N, NH, O, and S, where the heteroaryl is optionally substituted with from 1-3R$^b$;
(xv) —C$_{3-10}$ cycloalkyl that is optionally substituted with from 1-4R$^b$,
(xvi) -heterocyclyl including from 3-10 ring atoms, where from 1-3 ring atoms are each independently selected from the group consisting of N, NH and O, where the heterocyclyl is optionally substituted with from 1-4R$^b$,
(xx) —C(O)Rᵃ; and
(xxi) —SO$_{1-2}$(Rᵃ);
each occurrence of Rᵃ is independently selected from the group consisting of:
(i) H;
(ii) C$_{1-8}$ alkyl optionally substituted with from 1-3 independently selected R$^b$;
(iii) —(C$_{0-6}$ alkylene)-C$_{3-10}$ cycloalkyl, where the cycloalkyl is optionally substituted with from 1-4 independently selected R$^b$;
(iv) —(C$_{0-6}$ alkylene)-heterocyclyl including from 3-10 ring atoms, where from 1-3 ring atoms are each independently selected from the group consisting of NH, O, and S, where the heterocyclyl is optionally substituted with from 1-4 independently selected R$^b$;
(v) —(C$_{0-6}$ alkylene)-(C$_{6-10}$ aryl), where the aryl is optionally substituted with from 1-5 independently selected R$^b$; or
(vi) —(C$_{0-6}$ alkylene)-heteroaryl including from 5-10 ring atoms, where from 1-4 ring atoms are each independently selected from the group consisting of N, NH, O, and S, where the heteroaryl is optionally substituted with from 1-3 independently selected R$^b$;
each occurrence of R$^b$ is independently selected from the group consisting of:
(i) halo;
(ii) cyano;
(iii) C$_{1-6}$ alkyl;
(iv) C$_{2-6}$ alkenyl;
(V) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl including from 3-10 ring atoms, where from 1-3 ring atoms are each independently selected from the group consisting of NH, O, and S, where the heterocyclyl is optionally substituted with from 1-4 independently selected C$_{1-4}$ alkyl;
(xi) —(C$_{0-3}$ alkylene)-phenyl;
(xii) —(C$_{0-3}$ alkylene)-heteroaryl including from 5-10 ring atoms, where from 1-4 ring atoms are each independently selected from the group consisting of N, NH, O, and S;
(xiii) —S(O)$_{1-2}$(C$_{1-4}$ alkyl); and
(xiv) —NR'R";
(xv) —OH;
(xvi) —S(O)$_{1-2}$(NR'R");
(xvii) —C$_{1-4}$ thioalkoxy;
(xviii) —NO$_2$;
(xix) —N(R')(C(=O)C$_{1-3}$ alkyl);
(xx) —C(=O)(C$_{1-4}$ alkyl);
(xxi) —C(=O)O(C$_{1-4}$ alkyl);
(xxii) —C(=O)OH, and
(xxiii) —C(=O)N(R')(R");
each occurrence of R' and R" is independently selected from the group consisting of: H and C$_{1-4}$ alkyl; or, if R' and R" are bonded to the same atom, R' and R" together with the atom to which each is attached forms a ring including from 3-8 ring atoms, where the ring includes: (a) from 1-7 ring carbon atoms; and (b) from 0-3 ring heteroatoms (in addition to the atom attached to R' and R"), which are each independently selected from the group consisting of N, NH, O, and S.

In some embodiments, X is —CH$_2$—. In some embodiments, X$^1$ and X$^2$ are both absent.

In some embodiments, R is (ii) —ORᵃ, and where the Rᵃ of —ORᵃ is not (i) H or (ii) C$_{1-8}$ alkyl substituted with —(C$_{0-3}$ alkylene)-C$_{3-6}$ cycloalkyl.

In some embodiments, R is selected from the group consisting of:
(ix) —NRᵃRᵃ, where 1 Rᵃ is H;
(x) —NRᵃC(O)NRᵃRᵃ, where at least 1 Rᵃ is H;
(xi) —NRᵃC(O)ORᵃ, where the Rᵃ bonded to N is H; and
(xii) —NRᵃC(O)Rᵃ.

In some embodiments, R is selected from the group consisting of:
(vi) —CO$_2$Rᵃ, where the Rᵃ of —CO$_2$Rᵃ is not H; and
(xx) —C(O)Rᵃ.

In any of the previous embodiments, each occurrence of Rᵃ is independently selected from the group consisting of:
(i) H;
(ii) C$_{1-8}$ alkyl optionally substituted with from 1-3 independently selected R$^b$.

In any of the previous embodiments, each occurrence of R$^b$ is independently selected from the group consisting of:
(i) halo;
(ii) cyano;
(iii) C$_{1-6}$ alkyl;
(vi) C$_{1-4}$ haloalkyl;
(vii) C$_{1-4}$ alkoxy;
(xi) —(C$_{0-3}$ alkylene)-phenyl;
(xii) —(C$_{0-3}$ alkylene)-heteroaryl including from 5-10 ring atoms, where from 1-4 ring atoms are each independently selected from the group consisting of N, NH, O, and S;
(xiv) —NR'R";
(xv) —OH.

In any of the previous embodiments, each occurrence of R$^b$ is independently selected from the group consisting of:
(iii) C$_{1-6}$ alkyl;
(vii) C$_{1-4}$ alkoxy;
(xi) —(C$_{0-3}$ alkylene)-phenyl;
(xii) —(C$_{0-3}$ alkylene)-heteroaryl including from 5-10 ring atoms, where from 1-4 ring atoms are each independently selected from the group consisting of N, NH, O, and S;
(xv) —OH.

In any of the previous embodiments, each occurrence of R' and R" is independently selected from the group consisting of: H and C$_{1-4}$ alkyl.

In some embodiments, the complexing agent is a compound of Formula (II), or an anion or salt thereof:

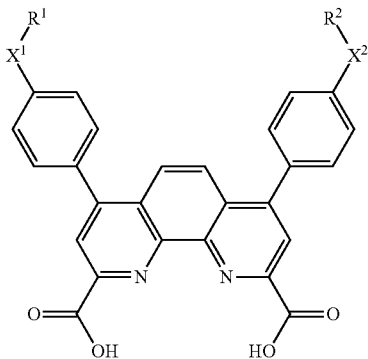

Formula (II)

where:
each of $X^1$ and $X^2$ is independently present or absent, and when one or both are present, each is independently selected from the group consisting of: $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH;
each of $R^1$ and $R^2$ is independently selected from the group consisting of:
(i) hydrogen;
(ii) —$OR^a$;
(iii) $C_{1-4}$ alkoxy optionally substituted with from 1-3$R^b$;
(iv) $C_{1-4}$ haloalkoxy;
(v) —COH;
(vi) —$CO_2R^a$;
(vii) —$CONR^aR^a$;
(viii) cyano;
(ix) —$NR^aR^a$;
(x) —$NR^aC(O)NR^aR^a$;
(xi) —$NR^aC(O)OR^a$;
(xii) —$NR^aC(O)R^a$;
(xiii) -aryl that is optionally substituted with from 1-3$R^b$;
(xiv) -heteroaryl including from 5-10 ring atoms, where from 1-4 ring atoms are each independently selected from the group consisting of N, NH, O, and S, where the heteroaryl is optionally substituted with from 1-3$R^b$;
(xv) —$C_{3-10}$ cycloalkyl that is optionally substituted with from 1-4$R^b$,
(xvi) -heterocyclyl including from 3-10 ring atoms, where from 1-3 ring atoms are each independently selected from the group consisting of N, NH and O, where the heterocyclyl is optionally substituted with from 1-4$R^b$;
(xvii) $C_{1-4}$ thioalkoxy;
(xviii) —$N_3$;
(xix) —$CO_2H$;
(xx) —$C(O)R^a$;
(xxi) —$SO_{1-2}(R^a)$; and
(xxii) —$O_nP(O)_nY_2$, where n is independently 0 or 1, and where Y is independently selected from —$OR^a$, $NR^aR^a$, and $C_{1-6}$ alkyl;
each occurrence of $R^a$ is independently selected from the group consisting of:
(i) H;
(ii) $C_{1-8}$ alkyl optionally substituted with from 1-3 independently selected $R^b$;
(iii) —($C_{0-6}$ alkylene)-$C_{3-10}$ cycloalkyl, where the cycloalkyl is optionally substituted with from 1-4 independently selected $R^b$;
(iv) —($C_{0-6}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $R^b$;
(v) —($C_{0-6}$ alkylene)-($C_{6-10}$ aryl), where the aryl is optionally substituted with from 1-5 independently selected $R^b$; or
(vi) —($C_{0-6}$ alkylene)-heteroaryl including from 5-10 ring atoms, where from 1-4 ring atoms are each independently selected from the group consisting of N, NH, O, and S, where the heteroaryl is optionally substituted with from 1-3 independently selected $R^b$;
each occurrence of $R^b$ is independently selected from the group consisting of:
(i) halo;
(ii) cyano;
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $C_{1-4}$ alkyl;
(xi) —($C_{0-3}$ alkylene)-phenyl;
(xii) —($C_{0-3}$ alkylene)-heteroaryl including from 5-10 ring atoms, where from 1-4 ring atoms are each independently selected from the group consisting of N, NH, O, and S;
(xiii) —$S(O)_{1-2}(C_{1-4}$ alkyl); and
(xiv) —NR'R";
(xv) —OH;
(xvi) —$S(O)_{1-2}(NR'R")$;
(xvii) —$C_{1-4}$ thioalkoxy;
(xviii) —$NO_2$;
(xix) —N(R')(C(=O)$C_{1-3}$ alkyl);
(xx) —C(=O)($C_{1-4}$ alkyl);
(xxi) —C(=O)O($C_{1-4}$ alkyl);
(xxii) —C(=O)OH, and
(xxiii) —C(=O)N(R')(R");
each occurrence of R' and R" is independently selected from the group consisting of: H and $C_{1-4}$ alkyl; or, if R' and R" are bonded to the same atom, R' and R" together with the atom to which each is attached forms a ring including from 3-8 ring atoms, where the ring includes: (a) from 1-7 ring carbon atoms; and (b) from 0-3 ring heteroatoms (in addition to the atom attached to R' and R"), which are each independently selected from the group consisting of N, NH, O, and S.

In some embodiments, each of $X^1$ and $X^2$ is independently present or absent, and when one or both are present, each is independently selected from the group consisting of: $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH;

each of $R^1$ and $R^2$ is independently selected from the group consisting of:
(ii) —$OR^a$;
(iii) $C_{1-4}$ alkoxy optionally substituted with from 1-3$R^b$;
(iv) $C_{1-4}$ haloalkoxy;
(vi) —$CO_2R^a$;
(vii) —$CONR^aR^a$;
(viii) cyano;
(ix) —$NR^aR^a$;
(x) —$NR^aC(O)NR^aR^a$;
(xi) —$NR^aC(O)OR^a$;
(xii) —$NR^aC(O)R^a$;
(xiii) -aryl that is optionally substituted with from 1-3$R^b$;
(xiv) -heteroaryl including from 5-10 ring atoms, where from 1-4 ring atoms are each independently selected from the group consisting of N, NH, O, and S, where the heteroaryl is optionally substituted with from 1-3$R^b$;
(xv) —$C_{3-10}$ cycloalkyl that is optionally substituted with from 1-4$R^b$,
(xvi) -heterocyclyl including from 3-10 ring atoms, where from 1-3 ring atoms are each independently selected from the group consisting of N, NH and O, where the heterocyclyl is optionally substituted with from 1-4$R^b$,
(xix) —$CO_2H$;
(xx) —$C(O)R^a$; and
(xxi) —$SO_{1-2}(R^a)$;

each occurrence of $R^a$ is independently selected from the group consisting of:
(i) H;
(ii) $C_{1-8}$ alkyl optionally substituted with from 1-3 independently selected $R^b$;
(iii) —($C_{0-6}$ alkylene)-$C_{3-10}$ cycloalkyl, where the cycloalkyl is optionally substituted with from 1-4 independently selected $R^b$;
(iv) —($C_{0-6}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $R^b$;
(v) —($C_{0-6}$ alkylene)-($C_{6-10}$ aryl), where the aryl is optionally substituted with from 1-5 independently selected $R^b$; or
(vi) —($C_{0-6}$ alkylene)-heteroaryl including from 5-10 ring atoms, where from 1-4 ring atoms are each independently selected from the group consisting of N, NH, O, and S, where the heteroaryl is optionally substituted with from 1-3 independently selected $R^b$;

each occurrence of $R^b$ is independently selected from the group consisting of:
(i) halo;
(ii) cyano;
(iii) $C_{1-6}$ alkyl;
(iv) $C_{2-6}$ alkenyl;
(V) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $C_{1-4}$ alkyl;
(xi) —($C_{0-3}$ alkylene)-phenyl;
(xii) —($C_{0-3}$ alkylene)-heteroaryl including from 5-10 ring atoms, where from 1-4 ring atoms are each independently selected from the group consisting of N, NH, O, and S;
(xiii) —$S(O)_{1-2}(C_{1-4}$ alkyl); and
(xiv) —NR'R";
(xv) —OH;
(xvi) —$S(O)_{1-2}(NR'R")$;
(xvii) —$C_{1-4}$ thioalkoxy;
(xviii) —$NO_2$;
(xix) —N(R')(C(=O)$C_{1-3}$ alkyl);
(xx) —C(=O)($C_{1-4}$ alkyl);
(xxi) —C(=O)O($C_{1-4}$ alkyl);
(xxii) —C(=O)OH, and
(xxiii) —C(=O)N(R')(R");

each occurrence of R' and R" is independently selected from the group consisting of: H and $C_{1-4}$ alkyl; or, if R' and R" are bonded to the same atom, R' and R" together with the atom to which each is attached forms a ring including from 3-8 ring atoms, where the ring includes: (a) from 1-7 ring carbon atoms; and (b) from 0-3 ring heteroatoms (in addition to the atom attached to R' and R"), which are each independently selected from the group consisting of N, NH, O, and S.

In some embodiments, $X^1$ and $X^2$ are both —$CH_2$—. In some embodiments, $X^1$ and $X^2$ are both absent.

In some embodiments, $R^1$ and $R^2$ are independently selected from:
(ix) —$NR^aR^a$;
(x) —$NR^aC(O)NR^aR^a$;
(xi) —$NR^aC(O)OR^a$; and
(xii) —$NR^aC(O)R^a$.

In some embodiments, $R^1$ and $R^2$ are independently selected from:
(ix) —$NHR^a$;
(x) —$NHC(O)NHR^a$;
(xi) —$NHC(O)OR^a$; and
(xii) —$NHC(O)R^a$.

In some embodiments, $R^1$ and $R^2$ are each (ix) —$NHR^a$ (for example, —$NH_2$). In certain of these embodiments, $R^a$ is selected from (ii) $C_{1-8}$ alkyl substituted with from 1-3 independently selected $R^b$, where at least one of the $R^b$ is (xv) —OH.

In some embodiments, $R^1$ and $R^2$ are each (x) —NHC(O)NHR$^a$. In some embodiments, $R^1$ and $R^2$ are each (xi) —NHC(O)OR$^a$. In some embodiments, $R^1$ and $R^2$ are each (xii) —NHC(O)R$^a$.

In some embodiments, each of $R^1$ and $R^2$ is the same. In some embodiments, each of $R^1$ and $R^2$ is different.

In any of the previous embodiments, each occurrence of $R^a$ is independently selected from the group consisting of:
(i) H;
(ii) $C_{1-8}$ alkyl optionally substituted with from 1-3 independently selected $R^b$.

In any of the previous embodiments, each occurrence of $R^b$ is independently selected from the group consisting of:
(i) halo;
(ii) cyano;
(iii) $C_{1-6}$ alkyl;
(vi) $C_{1-4}$ haloalkyl;
(vii) $C_{1-4}$ alkoxy;
(xi) —($C_{0-3}$ alkylene)-phenyl;
(xii) —($C_{0-3}$ alkylene)-heteroaryl including from 5-10 ring atoms, where from 1-4 ring atoms are each independently selected from the group consisting of N, NH, O, and S;
(xiv) —NR'R";
(xv) —OH.

In any of the previous embodiments, each occurrence of $R^b$ is independently selected from the group consisting of:
- (iii) $C_{1-6}$ alkyl;
- (vii) $C_{1-4}$ alkoxy;
- (xi) —($C_{0-3}$ alkylene)-phenyl;
- (xii) —($C_{0-3}$ alkylene)-heteroaryl including from 5-10 ring atoms, where from 1-4 ring atoms are each independently selected from the group consisting of N, NH, O, and S;
- (xv) —OH.

In any of the previous embodiments, each occurrence of R' and R" is independently selected from the group consisting of: H and $C_{1-4}$ alkyl.

In some embodiments, the complexing agent is a compound of Formula (III), or an anion or salt thereof:

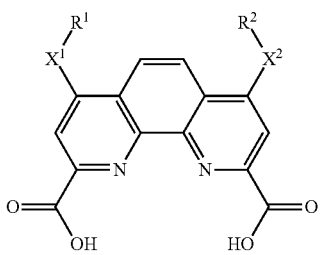

Formula (III)

where:
each of $X^1$ and $X^2$ is independently present or absent, and when one or both are present, each is independently selected from the group consisting of: $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH;

each of $R^1$ and $R^2$ is independently selected from the group consisting of:
- (i) hydrogen;
- (ii) —$OR^a$;
- (iii) $C_{1-4}$ alkoxy optionally substituted with from 1-3$R^b$;
- (iv) $C_{1-4}$ haloalkoxy;
- (v) —COH;
- (vi) —$CO_2R^a$;
- (vii) —$CONR^aR^a$;
- (viii) cyano;
- (ix) —$NR^aR^a$;
- (x) —$NR^aC(O)NR^aR^a$;
- (xi) —$NR^aC(O)OR^a$;
- (xii) —$NR^aC(O)R^a$;
- (xiii) -aryl that is optionally substituted with from 1-3$R^b$;
- (xiv) -heteroaryl including from 5-10 ring atoms, where from 1-4 ring atoms are each independently selected from the group consisting of N, NH, O, and S, where the heteroaryl is optionally substituted with from 1-3$R^b$;
- (xv) —$C_{3-10}$ cycloalkyl that is optionally substituted with from 1-4$R^b$,
- (xvi) -heterocyclyl including from 3-10 ring atoms, where from 1-3 ring atoms are each independently selected from the group consisting of N, NH and O, where the heterocyclyl is optionally substituted with from 1-4$R^b$,
- (xvii) $C_{1-4}$ thioalkoxy;
- (xviii) —$N_3$;
- (xix) —$CO_2H$;
- (xx) —$C(O)R^a$;
- (xxi) —$SO_{1-2}(R^a)$;
- (xxii) —$O_nP(O)_nY_2$, where n is independently 0 or 1, and where Y is independently selected from —$OR^a$, $NR^aR^a$, and $C_{1-6}$ alkyl; and
- (xxiii) halo (e.g., —F, —Cl, —Br, —I);

each occurrence of $R^a$ is independently selected from the group consisting of:
- (i) H;
- (ii) $C_{1-8}$ alkyl optionally substituted with from 1-3 independently selected $R^b$;
- (iii) —($C_{0-6}$ alkylene)-$C_{3-10}$ cycloalkyl, where the cycloalkyl is optionally substituted with from 1-4 independently selected $R^b$;
- (iv) —($C_{0-6}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $R^b$;
- (v) —($C_{0-6}$ alkylene)-($C_{6-10}$ aryl), where the aryl is optionally substituted with from 1-5 independently selected $R^b$; or
- (vi) —($C_{0-6}$ alkylene)-heteroaryl including from 5-10 ring atoms, where from 1-4 ring atoms are each independently selected from the group consisting of N, NH, O, and S, where the heteroaryl is optionally substituted with from 1-3 independently selected $R^b$;

each occurrence of $R^b$ is independently selected from the group consisting of:
- (i) halo;
- (ii) cyano;
- (iii) $C_{1-6}$ alkyl;
- (iv) $C_{2-6}$ alkenyl;
- (v) $C_{2-6}$ alkynyl;
- (vi) $C_{1-4}$ haloalkyl;
- (vii) $C_{1-4}$ alkoxy;
- (viii) $C_{1-4}$ haloalkoxy;
- (ix) —($C_{0-3}$ alkylene)-$C_{3-6}$ cycloalkyl optionally substituted with from 1-4 independently selected $C_{1-4}$ alkyl;
- (x) —($C_{0-3}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $C_{1-4}$ alkyl;
- (xi) —($C_{0-3}$ alkylene)-phenyl;
- (xii) —($C_{0-3}$ alkylene)-heteroaryl including from 5-10 ring atoms, where from 1-4 ring atoms are each independently selected from the group consisting of N, NH, O, and S;
- (xiii) —$S(O)_{1-2}(C_{1-4}$ alkyl); and
- (xiv) —NR'R";
- (xv) —OH;
- (xvi) —$S(O)_{1-2}(NR'R")$;
- (xvii) —$C_{1-4}$ thioalkoxy;
- (xviii) —$NO_2$;
- (xix) —N(R')(C(=O)$C_{1-3}$ alkyl);
- (xx) —C(=O)($C_{1-4}$ alkyl);
- (xxi) —C(=O)O($C_{1-4}$ alkyl);
- (xxii) —C(=O)OH, and
- (xxiii) —C(=O)N(R')(R");

each occurrence of R' and R" is independently selected from the group consisting of: H and $C_{1-4}$ alkyl; or, if R' and R" are bonded to the same atom, R' and R" together with the atom to which each is attached forms a ring including from 3-8 ring atoms, where the ring includes: (a) from 1-7 ring carbon atoms; and (b) from 0-3 ring heteroatoms (in addition to the atom attached to R' and R"), which are each independently selected from the group consisting of N, NH, O, and S.

In some embodiments, each of $X^1$ and $X^2$ is independently present or absent, and when one or both are present, each is independently selected from the group consisting of: $C_{1-10}$ alkylene, $C_{2-10}$ alkenylene, and $C_{2-10}$ alkynylene, where each $C_{1-10}$ alkylene, $C_{2-10}$ alkenylene, and $C_{2-10}$ alkynylene is optionally interrupted by one O, S, or NH;

each of $R^1$ and $R^2$ is independently selected from the group consisting of:
- (ii) —$OR^a$;
- (iii) $C_{1-4}$ alkoxy optionally substituted with from 1-3$R^b$;
- (iv) $C_{1-4}$ haloalkoxy;
- (vi) —$CO_2R^a$;
- (vii) —$CONR^aR^a$;
- (viii) cyano;
- (ix) —$NR^aR^a$;
- (x) —$NR^aC(O)NR^aR^a$;
- (xi) —$NR^aC(O)OR^a$;
- (xii) —$NR^aC(O)R^a$;
- (xiii) -aryl that is optionally substituted with from 1-3$R^b$;
- (xiv) -heteroaryl including from 5-10 ring atoms, where from 1-4 ring atoms are each independently selected from the group consisting of N, NH, O, and S, where the heteroaryl is optionally substituted with from 1-3$R^b$;
- (xv) —$C_{3-10}$ cycloalkyl that is optionally substituted with from 1-4$R^b$,
- (xvi) -heterocyclyl including from 3-10 ring atoms, where from 1-3 ring atoms are each independently selected from the group consisting of N, NH and O, where the heterocyclyl is optionally substituted with from 1-4$R^b$,
- (xix) —$CO_2H$;
- (xx) —$C(O)R^a$;
- (xxi) —$SO_{1-2}(R^a)$; and
- (xxii) halo (e.g., —F, —Cl, —Br, —I);

each occurrence of $R^a$ is independently selected from the group consisting of:
- (i) H;
- (ii) $C_{1-8}$ alkyl optionally substituted with from 1-3 independently selected $R^b$;
- (iii) —$(C_{0-6}$ alkylene)-$C_{3-10}$ cycloalkyl, where the cycloalkyl is optionally substituted with from 1-4 independently selected $R^b$;
- (iv) —$(C_{0-6}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $R^b$;
- (v) —$(C_{0-6}$ alkylene)-$(C_{6-10}$ aryl), where the aryl is optionally substituted with from 1-5 independently selected $R^b$; or
- (vi) —$(C_{0-6}$ alkylene)-heteroaryl including from 5-10 ring atoms, where from 1-4 ring atoms are each independently selected from the group consisting of N, NH, O, and S, where the heteroaryl is optionally substituted with from 1-3 independently selected $R^b$;

each occurrence of $R^b$ is independently selected from the group consisting of:
- (i) halo;
- (ii) cyano;
- (iii) $C_{1-6}$ alkyl;
- (iv) $C_{2-6}$ alkenyl;
- (v) $C_{2-6}$ alkynyl;
- (vi) $C_{1-4}$ haloalkyl;
- (vii) $C_{1-4}$ alkoxy;
- (viii) $C_{1-4}$ haloalkoxy;
- (ix) —$(C_{0-3}$ alkylene)-$C_{3-6}$ cycloalkyl optionally substituted with from 1-4 independently selected $C_{1-4}$ alkyl;
- (x) —$(C_{0-3}$ alkylene)-heterocyclyl including from 3-10 ring atoms, where from 1-3 ring atoms are each independently selected from the group consisting of NH, O, and S, where the heterocyclyl is optionally substituted with from 1-4 independently selected $C_{1-4}$ alkyl;
- (xi) —$(C_{0-3}$ alkylene)-phenyl;
- (xii) —$(C_{0-3}$ alkylene)-heteroaryl including from 5-10 ring atoms, where from 1-4 ring atoms are each independently selected from the group consisting of N, NH, O, and S;
- (xiii) —$S(O)_{1-2}(C_{1-4}$ alkyl); and
- (xiv) —NR'R";
- (xv) —OH;
- (xvi) —$S(O)_{1-2}(NR'R")$;
- (xvii) —$C_{1-4}$ thioalkoxy;
- (xviii) —$NO_2$;
- (xix) —$N(R')(C(=O)C_{1-3}$ alkyl);
- (xx) —$C(=O)(C_{1-4}$ alkyl);
- (xxi) —$C(=O)O(C_{1-4}$ alkyl);
- (xxii) —$C(=O)OH$, and
- (xxiii) —$C(=O)N(R')(R")$;

each occurrence of R' and R" is independently selected from the group consisting of: H and $C_{1-4}$ alkyl; or, if R' and R" are bonded to the same atom, R' and R" together with the atom to which each is attached forms a ring including from 3-8 ring atoms, where the ring includes: (a) from 1-7 ring carbon atoms; and (b) from 0-3 ring heteroatoms (in addition to the atom attached to R' and R"), which are each independently selected from the group consisting of N, NH, O, and S.

In some embodiments, $X^1$ and $X^2$ are both —$CH_2$—. In some embodiments, $X^1$ and $X^2$ are both absent.

In some embodiments, $R^1$ and $R^2$ are independently selected from:
- (ix) —$NR^aR^a$;
- (x) —$NR^aC(O)NR^aR^a$;
- (xi) —$NR^aC(O)OR^a$; and
- (xii) —$NR^aC(O)R^a$.

In some embodiments, $R^1$ and $R^2$ are independently selected from:
- (ix) —$NHR^a$;
- (x) —$NHC(O)NHR^a$;
- (xi) —$NHC(O)OR^a$;
- (xii) —$NHC(O)R^a$; and
- (xiii) halo (—F, —Cl, —Br, —I).

In some embodiments, $R^1$ and $R^2$ are each (ix) —$NHR^a$ (for example, —$NH_2$). In certain of these embodiments, $R^a$ is selected from (ii) $C_{1-8}$ alkyl substituted with from 1-3 independently selected $R^b$, where at least one of the $R^b$ is (xv) —OH.

In some embodiments, $R^1$ and $R^2$ are each (x) —NHC(O)NHR$^a$. In some embodiments, $R^1$ and $R^2$ are each (xi) —NHC(O)OR$^a$. In some embodiments, $R^1$ and $R^2$ are each (xii) —NHC(O)R$^a$. In some embodiments, $R^1$ and $R^2$ are each —Cl.

In some embodiments, each of $R^1$ and $R^2$ is the same. In some embodiments, each of $R^1$ and $R^2$ is different.

In any of the previous embodiments, each occurrence of $R^a$ is independently selected from the group consisting of:
- (i) H;
- (ii) $C_{1-8}$ alkyl optionally substituted with from 1-3 independently selected $R^b$.

In any of the previous embodiments, each occurrence of $R^b$ is independently selected from the group consisting of:
(i) halo;
(ii) cyano;
(iii) $C_{1-6}$ alkyl;
(vi) $C_{1-4}$ haloalkyl;
(vii) $C_{1-4}$ alkoxy;
(xi) —$(C_{0-3}$ alkylene)-phenyl;
(xii) —$(C_{0-3}$ alkylene)-heteroaryl including from 5-10 ring atoms, where from 1-4 ring atoms are each independently selected from the group consisting of N, NH, O, and S;
(xiv) —NR'R";
(xv) —OH.

In any of the previous embodiments, each occurrence of $R^b$ is independently selected from the group consisting of:
(iii) $C_{1-6}$ alkyl;
(vii) $C_{1-4}$ alkoxy;
(xi) —$(C_{0-3}$ alkylene)-phenyl;
(xii) —$(C_{0-3}$ alkylene)-heteroaryl including from 5-10 ring atoms, where from 1-4 ring atoms are each independently selected from the group consisting of N, NH, O, and S;
(xv) —OH.

In any of the previous embodiments, each occurrence of R' and R" is independently selected from the group consisting of: H and $C_{1-4}$ alkyl.

In some embodiments, the complex includes water. In some embodiments, the complex includes two or more different complexing agents. Combinations of different complexing agents can be selected from among any of the agents disclosed previously.

In general, depending upon the one or more complexing agents used to form the complex and the lanthanide ion complexed, the resulting complex can have a variety of different geometries about the lanthanide ion. Examples of such geometries include, but are not limited to: trigonal bipyramidal; square pyramidal; octahedral; trigonal prismatic; pentagonal bipyramidal; face capped octahedral; trigonal prismatic, square face monocapped; cubic; square antiprismatic; dodecahedral; trigonal hexagonal bypyramidal; octahedral, trans-bicapped; trigonal prismatic, triangular face bicapped; trigonal prismatic, square face bicapped; and tricapped trigonal prismatic.

In general, any of the lanthanide elements can be used to form luminescent complexes for tracer detection. In some embodiments, the lanthanide ion in each complex can be selected from the group consisting of lanthanum, cerium, praseodymium, neodymium, promethium, samarium, europium, gadolinium, terbium, dysprosium, holmium, erbium, thulium, ytterbium, and lutetium. For example, the lanthanide ion is selected from the group consisting of samarium, europium, terbium, and dysprosium.

In some embodiments, the complex of Formula (I) includes a 1:1:2 molar ratio of lanthanide ion to complexing agent to water. In some embodiments, the complex of Formula (I) includes a 1:2:0 molar ratio of lanthanide ion to complexing agent to water.

In some embodiments, the complex of Formula (II) includes a 1:1:2 molar ratio of lanthanide ion to complexing agent to water. In some embodiments, the complex of Formula (II) includes a 1:2:1 molar ratio of lanthanide ion to complexing agent to water. In some embodiments, the complex of Formula (II) includes a 1:3:0 molar ratio of lanthanide ion to complexing agent to water.

Analysis and Enhancement of Reservoir Production

The information obtained using the methods described above can be used to analyze and improve reservoir production. Specifically, information obtained from cross-well tracers that incorporate the foregoing complexing agents can be used to adjust a variety of control parameters such as water injection rates and fluid extraction rates, to manage reservoir production. The use of tracer information can increase constraints on history matching processes that are used for reservoir analysis, and can provide a more cost-effective and non-instrusive method for monitoring and managing reservoirs than conventional methods such as pressure interference studies, loggings, additional well drillings, and tomography.

For example, inter-well tracer information can be integrated into algorithms such as an ensemble smoother with multiple data assimilation (ES-MDA-Tracer), which can improve history matching using integrated production and tracer information, thereby generating accurate reservoir geological models with improved prediction accuracy. Such models can then be used to improve or optimize reservoir production.

Examples of methods of using tracer-derived information for analysis and improvement of reservoir production are described, for example, in U.S. patent application Ser. No. 15/786,372 entitled "Enhancing Reservoir Production Optimization Through Integrating Inter-Well Tracers", filed on Oct. 17, 2017, the entire contents of which are incorporated herein by reference.

EXAMPLES

This section provides a number of specific examples to further illustrate the previous disclosure. These examples are not intended to limit the scope of the disclosure in any manner.

Example 1—Synthesis of Complexing Agents

Compounds of Formula (I)

A variety of complexing agents of Formula (I), each having distinguishing moieties, were prepared through the derivatization of dimethyl 4-(hydroxymethyl)pyridine-2,6-dicarboxylate and dimethyl 4-chloropyridine-2,6-dicarboxylate as depicted in forthcoming Scheme 2. First, a versatile hydroxymethylated scaffold was prepared through hydroxymethylation of dimethyl pyridine-2,6-dicarboxylate (part "a"). Next, various transformations (for example, tosylation, iodination, part "b") were carried out to generate a variety of complexing agents. Part "c" depicts the functionalization of a separate DPA derivative, dimethyl 4-chloropyridine-2,6-dicarboxylate, with imidazole-based moieties. Part "d" illustrates the functionalization of dimethyl 4-carboxypyridine-2,6-dicarboxylate, a synthetic precursor achieved from the oxidation of dimethyl 4-(hydroxymethyl)pyridine-2,6-dicarboxylate (shown in part "b"). Zwitterionic derivatives of DPA may also be synthesized from its imidazole-conjugated variants, as shown in part "e".

Scheme 1.
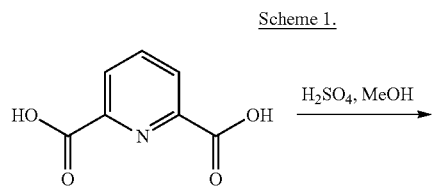 → 5 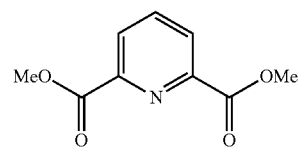
Scheme 2.
a.
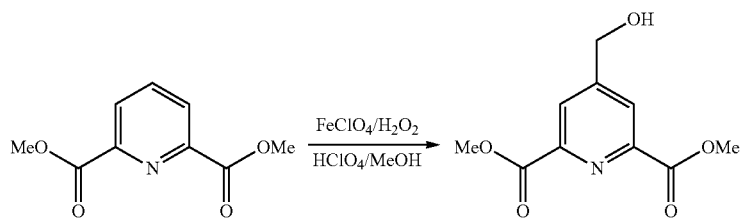
b.
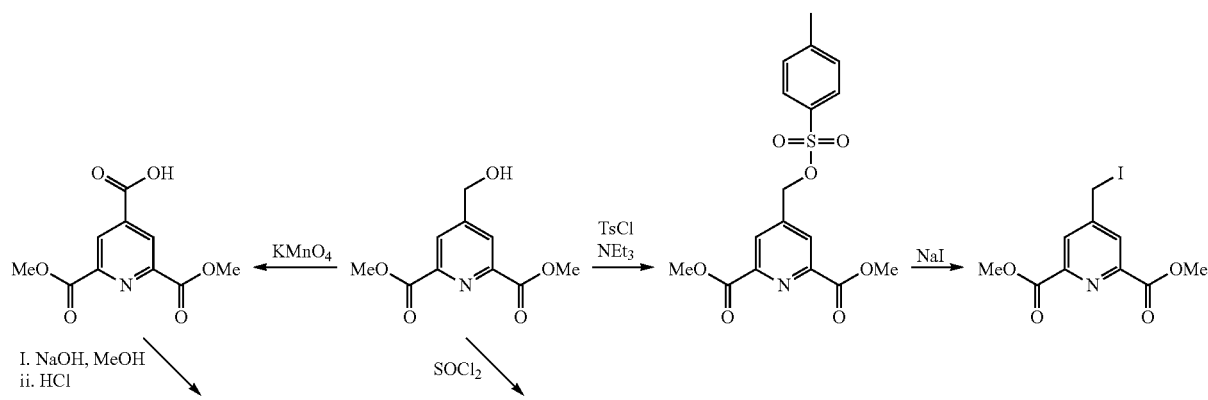
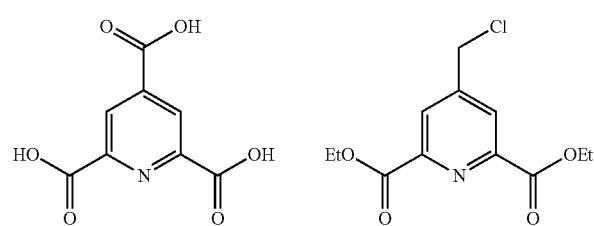

c.
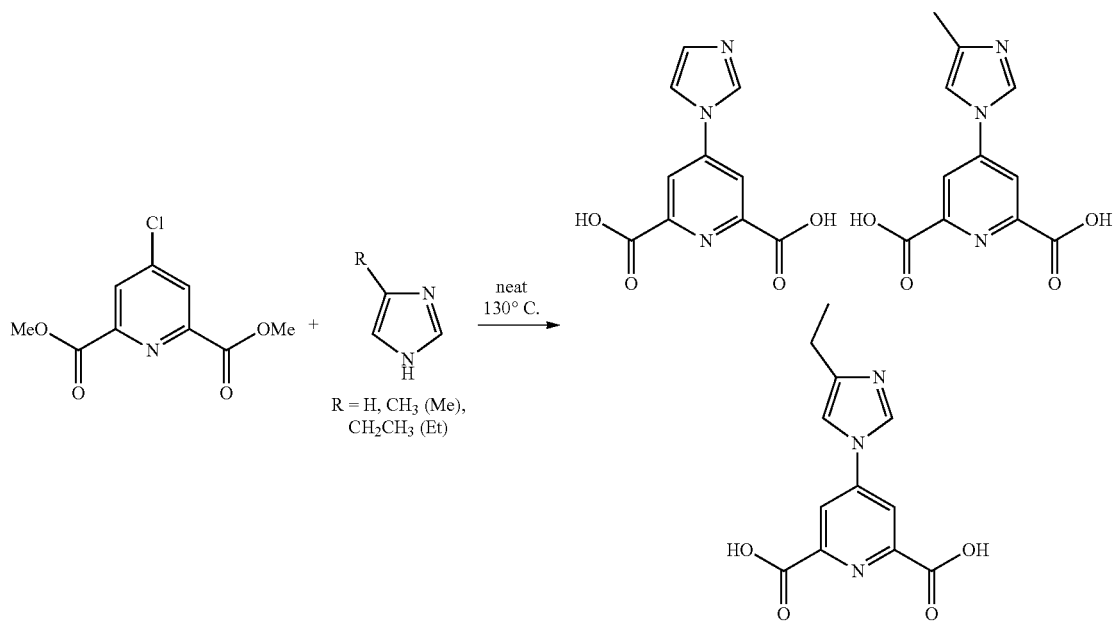
d.
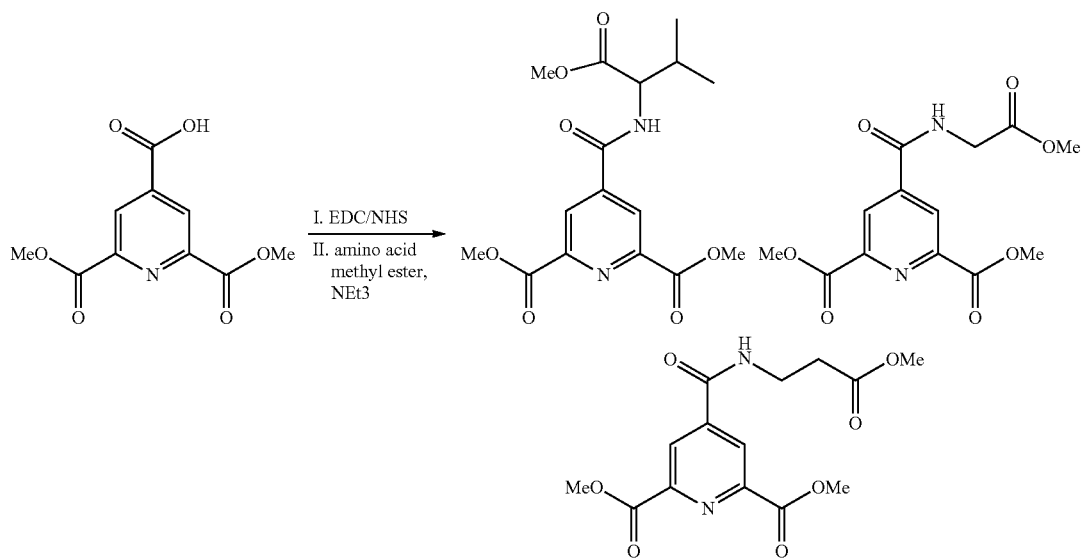

e.

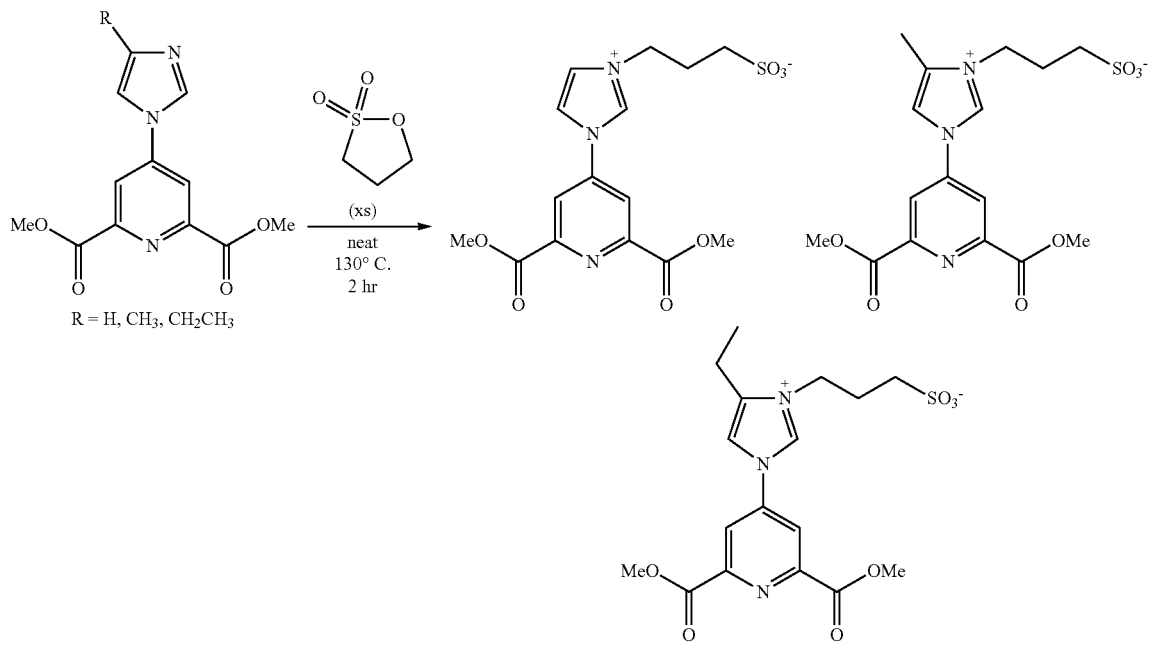

R = H, CH₃, CH₂CH₃

Synthesis of Dimethyl 2,6-pyridine dicarboxylate (DMDPA)

A solution of dipicolinic acid (4.00 grams (g), 24 millimoles (mmol)) in methanol (50 milliliters (ml)) and concentrated sulfuric acid (10 ml) was heated for 18 hours (h). Water (30 ml) was added and the aqueous solution was neutralized with sodium carbonate. The solution was acidified with concentrated HCl and extracted with chloroform (4×25 ml). The combined extracts were dried, filtered and concentrated to leave a white solid. Crystallization from chloroform gave dimethyl dipicolinate as a white powder (2.87 g, 96%). Proton nuclear magnetic resonance spectral peaks ($^1$H NMR) (500 Megahertz (MHz), CDCl₃) δ=8.33 (doublet (d), 2H), 8.03 (triplet (t), 1H), 4.03 (singlet (s), 6H).

Synthesis of Dimethyl 4-hydroxymethylpyridine-2,6-dicarboxylate

Solutions of Fe(ClO4)2.6H2O (4.64 g, 12.8 mmol) in H2O (4.7 mL) and H2O2 (30% weight/weight (w/w) aqueous solution, 8 mL, 77.6 mmol) were added dropwise at 0° C. over 30 minutes (min) to a mixture of DPA dimethyl ester (2.5 g, 12.8 mmol) 7, MeOH (7.5 mL) and HClO4 (70% w/w aqueous solution, 5.6 mL, 9.32 g, 64.9 mmol). The reaction mixture was allowed to warm up slowly to room temperature and it was stirred at this temperature for 3 h. The volatile components were evaporated under reduced pressure, and the pH of the residue was adjusted to 9 with saturated Na2CO3 solution. The aqueous solution was extracted with EtOAc (3×30 mL) and the combined organic phase was dried over MgSO4, filtered and the solvent was removed. The residue was recrystallized from toluene to give the titled compound (1.87 g, 65%) as white crystals. Melting point (mp): 158-159° C. (toluene) (literature mp (lit. mp): 154-158° C.), Rf=0.11 (SiO2 thin-layer chromatography (TLC); EtOAc-toluene 1:1). $^1$H NMR (500 MHz, CDCl₃) δ=8.32 (s, 2H), 4.91 (d, 2H), 4.03 (s, 6H), 2.06 (t, 1H).

Synthesis of Dimethyl 4-carboxypyridine-2,6-dicarboxylate

To a solution of dimethyl 4-(hydroxymethyl)pyridine-2,6-dicarboxylate (2 g, 8.8 mmol) in 50 ml acetone was added solid KMnO4 (4.21 g, 26.6 mmol), with stirring. The reaction mixture was allowed to stir for 3 hours at room temperature, then quenched with aqueous NaHSO3 within an ice bath. The resulting solution was then filtered over celite and the collected precipitate was washed with water. Concentration of the collected filtrate (to remove acetone) was followed by acidification of the remaining aqueous phase to pH 2 using 1 molar (M) HCl, which was then subjected to extraction with ethyl acetate. The combined organic phase was dried with MgSO4, filtered, and concentrated to afford the product as a white powder (50%). $^1$H NMR (500 MHz, DMSO-d₆) δ=14.29 (broad (br), 1H), 8.55 (s, 2H), 3.95 (s, 6H).

Synthesis of Dimethyl 4-tosyloxymethylpyridine-2,6-dicarboxylate

To a cooled solution of dimethyl 4-hydroxymethylpyridine-2,6-dicarboxylate (2.15 g, 9.56 mmol) in dichloromethane (20 ml) was added dropwise a solution of tosyl chloride (2.37 g, 12.4 mmol), after which the resulting solution was stirred for 20 min at 0° C. Triethylamine (6 ml) was then added dropwise in three portions at 20 min intervals. After the addition was complete, the solution was allowed to stir at 0° C. for an additional 15 min, followed by 15 min at room temperature. The resulting solution was diluted with EtOAc (40 ml), washed with water (2×20 ml) and 3M HCl (2×20 ml). The organic phase was then dried over MgSO4, filtered, and the solvent removed in vacuo to yield a brown powder, which was washed with diethyl ether (3×10 ml) to give the product as a tan powder (2.52 g, 70%). $^1$H NMR (500 MHz, CDCl₃) δ=8.17 (s, 2H), 7.82 (d, 2H), 7.35 (d, 2H), 5.18 (s, 2H), 4.02 (s, 6H), 2.45 (s, 3H).

Synthesis of Diethyl 4-chloromethylpyridine-2,6-dicarboxylate

To a solution of dimethyl 4-hydroxymethylpyridine-2,6-dicarboxylate (3.0 g, 13.3 mmol) in anhydrous CHCl3 was added SOCl2 (2.4 g, 20 mmol) dropwise under argon atmosphere at −5° C. with continuous stirring for 40 min. Excess solvent was removed in vacuo and the crude product was recrystallized from EtOH (50 ml) to give the product as a yellow solid after drying in vacuum (2.8 g, 86%). $^1$H NMR (500 MHz, CDCl$_3$) δ=8.30 (s, 2H), 4.67 (s, 2H), 4.50 (q, 4H), 1.47 (t, 6H).

Synthesis of Dimethyl 4-iodomethylpyridine-2,6-dicarboxylate

To a solution of NaI (4.50 g, 30 mmol) in acetone (250 ml) was added dimethyl 4-tosyloxylmethylpyridine-2-6-dicarboxylate (7.58 g, 20 mmol). The reaction mixture was then heated at reflux for 2.5 h, after which the cooled solution was diluted with EtOAc (550 ml), and the organic phase was washed with water (3×150 ml), 3% HCl (3×120 ml), and 5% w/w Na2SO3 (2×50 ml). The organic phase was dried over Na2SO4 in darkness and concentrated in vacuo to give the product (5.23 g, 78%). $^1$H NMR (500 MHz, CDCl$_3$) δ=8.27 (s, 2H), 4.44 (s, 2H), 4.03 (s, 6H).

Synthesis of 4-(1H-imidazol-1-yl)pyridine-2,6-dicarboxylic acids

Mixtures of dimethyl 4-chloropyridine-2,6-dicarboxylate (1 equivalent (eq.)) and imidazole/4-methylimidazole/4-ethylimidazole (5 (eq.)) were heated to 130° C. for 3.5 h in the absence of solvent. Upon cooling the dark reaction mixture was diluted with water and acidified to pH 3-4 using 1M HCl, precipitating the product as a brown powder (70-80%).

4-(1H-imidazol-1-yl)pyridine-2, 6-dicarboxylic acid $^1$H NMR (500 MHz, DMSO-d$_6$) δ=13.63 (br, 2H), 8.76 (s, 1H), 8.5 (s, 2H), 8.19 (s, 1H), 7.19 (s, 1H).

4-(4-methyl-1H-imidazol-1-yl)pyridine-2, 6-dicarboxylic acid $^1$H NMR (500 MHz, DMSO-d$_6$) δ=13.56 (br, 2H), 8.63 (s, 1H), 8.41 (s, 2H), 7.86 (s, 1H), 2.17 (s, 3H).

4-(4-ethyl-1H-imidazol-1-yl)pyridine-2, 6-dicarboxylic acid $^1$H NMR (500 MHz, DMSO-d$_6$) δ=13.59 (br, 2H), 8.65 (s, 1H), 8.44 (s, 2H), 7.89 (s, 1H), 2.53 (quadruplet (q), 2H), 1.21 (t, 3H).

Sulfonation of 4-(1H-imidazol-1-yl)pyridine-2,6-dicarboxylic acids

The pyridine dicarboxylic acids were first esterified to their methyl esters according to the procedure outlined below. A mixture of the resultant product (1 eq.) and 1,3-propanesultone (3 eq.) was then heated at 130° C. for 2 h. Upon cooling, the crude reaction was washed with MeOH and the resulting precipitate was filtered to give the desired product as a brown powder. Subsequent acid catalyzed hydrolysis was carried out as follows: compounds (dimethyl ester form) were suspended in 2 M HCl and heated at 80° C. for 2.5 h. Upon cooling, the desired product formed as a precipitate. The mixture was then filtered and washed with acetone to afford the product as a tan to brown powder.

1-[2,6-bis(methoxycarbonyl)-4-pyridyl]-3-(3-sulfopropyl)-4-methyl-1H-imidazolium $^1$H NMR (500 MHz, D$_2$O) δ=9.59 (s, 1H), 8.57 (s, 2H), 7.89 (s, 1H), 4.38 (t, 2H), 3.98 (s, 6H), 2.96 (t, 2H), 2.39 (s, 3H), 2.31 (sext, 2H).

1-[2, 6-bis(methoxycarbonyl)-4-pyridyl]-3-(3-sulfopropyl)-1H-imidazolium $^1$H NMR (500 MHz, D$_2$O) δ=9.69 (s, 1H), 8.62 (s, 2H), 8.13 (s, 1H), 7.81 (s, 1H), 4.48 (t, 2H), 3.99 (s, 6H), 2.93 (t, 2H), 2.36 (sext, 2H).

Esterification of 4-(1H-imidazol-1-yl)pyridine-2,6-dicarboxylic acids

The dicarboxylic acid (1 eq.) was charged with methanol (50 ml) and concentrated sulfuric acid (3 eq.) and subsequently refluxed for 16 h. The methanol was then concentrated in vacuo and the residue was triturated with saturated NaHCO$_3$, then water. The combined organic layers were dried over Na$_2$SO$_4$ and then the solvent was removed under reduced pressure to afford the desired ester as a tan solid.

General Procedure for the Hydrolysis of Dipicolinic Acids:

The following procedure was used to hydrolyze most 4-substituted dimethyl 2,6-pyridine dicarboxylate derivatives in addition to dimethyl 4-carboxypyridine-2,6-dicarboxylate. To a stirred solution of dimethyl ester in MeOH (10 ml) was added an equal volume of NaOH (20% weight/volume (w/v)). The reaction mixture was stirred overnight at room temperature and concentrated in vacuo. The residue was dissolved in the minimum required amount of water and acidified with conc. HCl. If a precipitate was obtained at this stage, the solution was cooled on ice and the precipitate was isolated by filtration and dried in vacuo to afford the desired carboxylic acid. If no precipitation occurred at this stage, the aqueous phases were repeatedly extracted with EtOAc, the organic layers were combined, dried (Na2SO4) and concentrated in vacuo to afford the desired carboxylic acid.

Compounds of Formula (II)

A variety of complexing agents of Formula (II), each having a unique distinguishing moiety, were prepared through the derivatization of bathocuproine (2,9-dimethyl-4,7-diphenyl-1,10-phenanthroline) as shown in Scheme 3a. Chlorination of bathocuproine followed by subsequent oxidation yields 4,7-diphenyl-1,10-phenanthroline-2,9-dicarboxylic acid (DPPDA), an intermediate product which undergoes treatment with HClSO$_3$ to ultimately give 4,7-diphenyl-1,10-phenanthroline-2,9-dicarboxylic acid disulfonate (BCPDCA). As shown in Scheme 3b, DPPDA may also undergo nitration to afford 4,7-bis(nitrophenyl)-1,10-phenanthroline-2,9-dicarboxylic acid, which may undergo further reduction to yield 4,7-bis(aminophenyl)-1,10-phenanthroline-2,9-dicarboxylic acid.

Scheme 3.
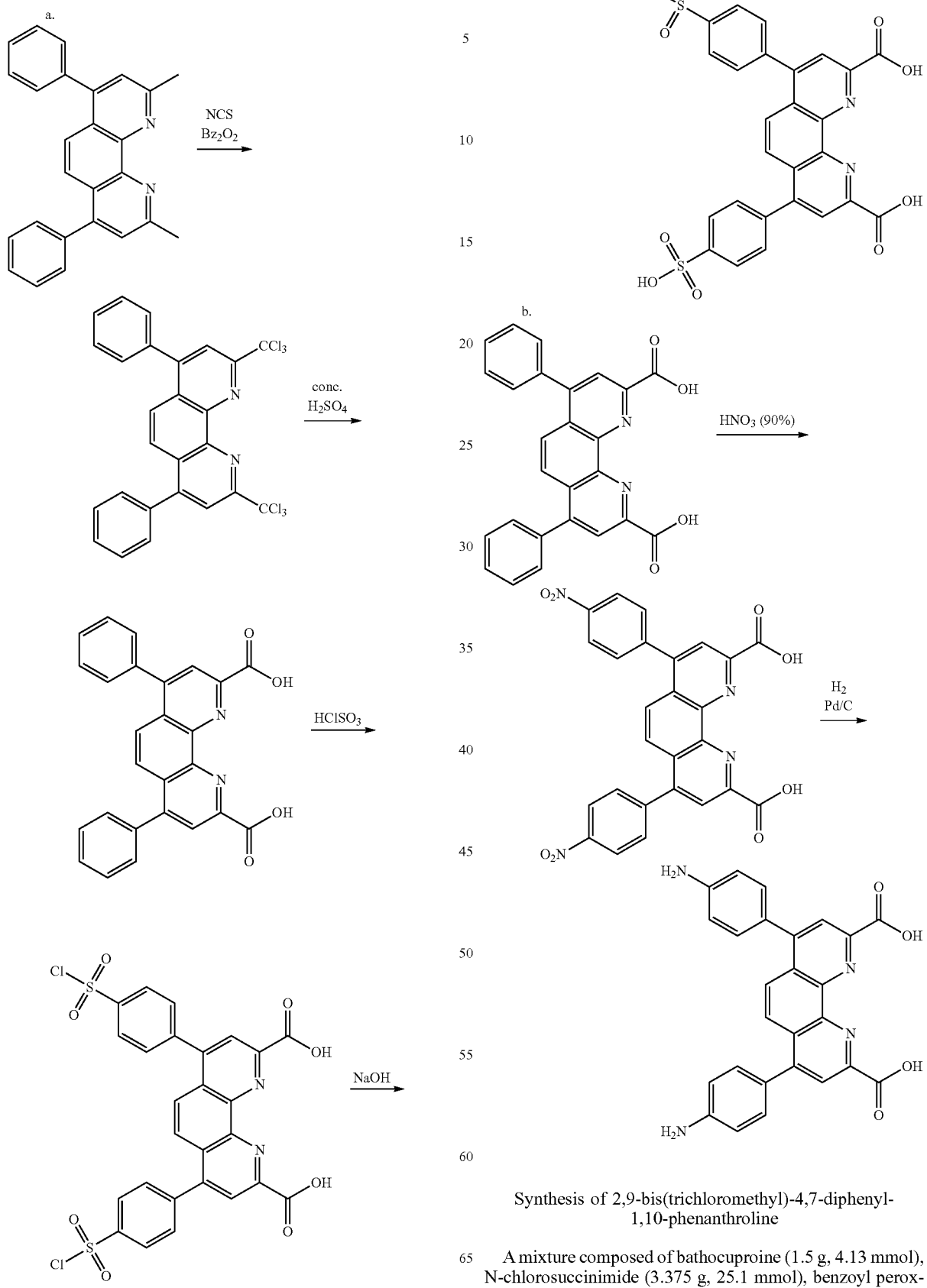
Synthesis of 2,9-bis(trichloromethyl)-4,7-diphenyl-1,10-phenanthroline
A mixture composed of bathocuproine (1.5 g, 4.13 mmol), N-chlorosuccinimide (3.375 g, 25.1 mmol), benzoyl peroxide (4.1 mg) and 36 ml chloroform was stirred and refluxed for 6 hrs in an oil bath at 90° C. The mixture was refrigerated overnight to allow precipitation of succinimide crystals, which were removed by vacuum filtration. The filtrate was then washed/extracted with 100 ml (2×50 ml) of saturated potassium carbonate solution (112 g/100 ml) and the organic layer was then dried over anhydrous MgSO4. Removal of solvent yielded the pale yellow solid product. Yield=81-93%. $^1$H NMR (500 MHz, CDCl$_3$) δ=8.27 (s, 2H), 8.0 (s, 2H), 7.57 (m, 10H).

Synthesis of 4,7-diphenyl-1,10-phenanthroline-2,9-dicarboxylic acid (DPPDA)

A 25 mL microwave vial was charged with 2,9-bis(trichloromethyl)-4,7-diphenyl-1,10-phenanthroline (1.612 g, 2.848 mmol) and 4 mL of concentrated H2SO4. The solution was stirred in a 90° C. oil bath for 2 h. After cooling to room temperature, 11 ml of deionized (DI) water was added dropwise to the continuously stirred reaction mixture. The resulting suspension was heated for an additional hour at 90° C. Upon cooling to room temperature, the solution was quenched into a 40 mL mixture of crushed ice and water. The resulting precipitate was collected via vacuum filtration. Yield=95% (hydrated). H NMR (500 MHz, DMSO-d$_6$) δ=13.7 (br, 2H), 8.29 (s, 2H), 8.04 (s, 2H), 7.65 (m, 10H).

Synthesis of 4,7-bis(chlorosulfonylphenyl)-1,10-phenanthroline-2,9-dicarboxylic acid To a 25 mL microwave vial was added 5 mL of 97% ClSO3H. The solution was cooled by placing in an ice bath. Cautiously, small aliquots of 4,7-diphenyl-1,10-phenanthroline-2,9-dicarboxylic acid was added to the stirred mixture until a total of 1 g was added. The mixture was then heated to 80° C. for 4 h. Upon cooling to room temperature, the solution was quenched into 100 mL of ice water in a drop wise fashion (Caution—this process is extremely exothermic). The resulting light yellow/beige powder was collected via vacuum filtration and lyophilized. Yield=79%. $^1$H NMR (500 MHz, DMSO-d$_6$) δ=8.29 (s, 2H), 8.05 (s, 2H), 7.58-7.9 (multiplet (m), 8H), 5.7 (br, 2H).

Synthesis of 4,7-diphenyl-1,10-phenanthroline-2,9-dicarboxylic acid disulfonate (BCPDCA)

Hydrolysis of 4,7-bis(chlorosulfonylphenyl)-1,10-phenanthroline-2,9-dicarboxylic acid was carried out using dilute NaOH (aqueous (aq)) pH 10 solutions. The chlorosulfonyl compound was suspended in pH 10 solution and mechanically stirred at room temperature until fully dissolved. The pH of the resulting solution was adjusted using dilute HCl solution until a final value of pH 6 was obtained.

Synthesis of 4,7-bis(nitrophenyl)-1,10-phenanthroline-2,9-dicarboxylic acid

To 3 ml of cold 90% HNO3 was added DPPDA (0.42 g, 1 mmol) in small portions, after which the mixture was stirred for 4.5 h in an ice bath. The reaction mixture was then poured over 100 ml crushed ice, yielding a yellow solid, and subsequently filtered and lyophilized to give the final product (96%). $^1$H NMR (500 MHz, DMSO-d$_6$) δ=13.8 (br, 2H), 8.54-7.56 (m, 12H).

Compounds of Formula (III)

A variant of complexing agents of Formula (III), each having distinguishing moieties, was prepared through the derivatization of 1,10-phenanthroline-2,9-dicarboxylic acid as depicted in forthcoming Scheme 4. First, precursor a was synthesized; subsequent reactions using a as a precursor yielded compound b, identified as 4,7-dichloro-2,9-dimethyl-1,10-phenanthroline. Compound b then underwent further transformations to yield 4,7-dichloro-1,10-phenanthroline-2,9-dicarboxylic acid.

Synthesis of 5,5'-((1,2-phenylenebis(azanediyl))bis(ethan-1-yl-1-ylidene))bis(2,2-dimethyl-1,3-dioxane-4,6-dione) (a)

Trimethyl orthoformate (500 mL, 3.83 mol) and Meldrum's acid (20.0 g, 139 mmol) was brought to a gentle reflux for 15 min. The resulting yellow solution was cooled (80° C.) and o-phenylenediamine (6.90 g, 63.1 mmol) was added portionwise (exothermic reaction). The resulting mixture was refluxed for 2 h, and left under stirring at rt for 16 h, where a white precipitate formed. The precipitate was filtered off, washed with diethyl ether (4×100 mL) and dried to afford the product as a flaky white solid.

Synthesis of 2,9-dimethyl-1,10-phenanthroline-4,7(1H,10H)-dione

To diphenyl ether (500 mL) at 240° C. was added a (17.5 g, 38.7 mmol) in small portions, resulting in vigorous gas evolution. The resulting orange solution was brought to reflux for 30 min, and was then allowed to cool to 70° C., where a dark-brown solid precipitated. The formed precipitate was washed with acetone (2×90 mL), hexane (2×90 mL) and Et2O (2×90 mL) and dried to afford a fine dark-brown powder.

Synthesis of 4,7-dichloro-2,9-dimethyl-1,10-phenanthroline (b)

To phosphoryl chloride (220 mL) under nitrogen was added 2,9-dimethyl-1,10-phenanthroline-4,7(1H, 10H)-dione (8.50 g, 35.4 mmol) and the resulting solution was stirred at 90° C. for 3.5 h. The hot solution was slowly added to a well-stirred mixture of ice (700 g) in water (300 mL). After stirring for 15 min, chloroform (200 mL) was added and the resulting two-layer system was carefully brought to pH 13-14 by adding NaOH solution (42.5%, ca. 450 mL). The organic layer was separated and the aqueous layer was extracted four times with 200 mL of chloroform. The combined organic layers were washed with NaOH solution (42.5%, 200 mL) and dried over MgSO$_4$. Evaporation of the brown colored solvent afforded b as light tan crystals.

Synthesis of 4,7-dichloro-2,9-bis(trichloromethyl)-1,10-phenanthroline

A stirred solution of b (9.00 g, 32.5 mmol), N-chlorosuccinimide (31.2 g, 234 mmol) and a catalytic amount of benzoyl peroxide (20 mg) in chloroform (700 mL) was refluxed overnight. The reaction mixture was washed with saturated aqueous K$_2$CO$_3$ (2×200 mL), dried over MgSO$_4$ and concentrated to afford a solid, which was purified by flash-chromatography (2% EtOAc in petroleum ether) to give the product as white crystals.

Synthesis of 4,7-dichloro-1,10-phenanthroline-2,9-dicarboxylic acid

A stirred mixture of 4,7-dichloro-2,9-bis(trichloromethyl)-1,10-phenanthroline (13.00 g, 26.9 mmol) in concentrated $H_2SO_4$ (16 mL) was heated to 95° C. for 2 h. After cooling, $H_2O$ (50 mL) was slowly added with rapid stirring. The resulting mixture was heated to reflux for 1 h. The mixture was cooled and the formed precipitate was washed with $H_2O$ (5×40 mL) and $Et_2O$ (2×30 mL) and dried to afford the product as a light tan solid.

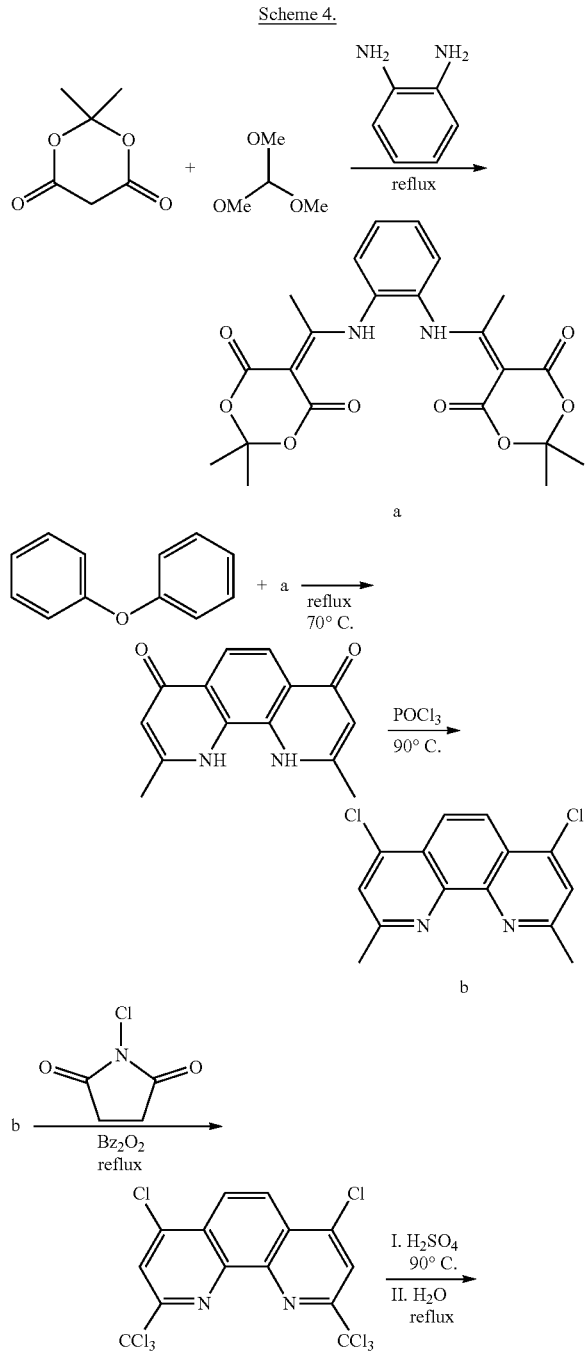

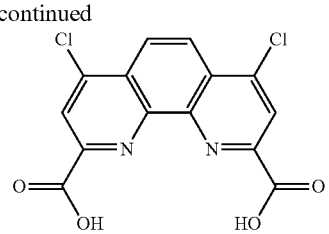

Example 2—Thermal Stability Test

One advantageous feature of molecular tracers for reservoir characterization is relatively uniform physical and chemical properties across a broad range of (1) salinity (for example, from about 60,000 ppm to about 250,000 ppm total dissolved salts) and (2) temperature (for example, from about 60° C. to about 105° C.), over relatively long periods of time, for example, while the tracer traverses a path from the injection well to the producing well. To evaluate properties of the disclosed tracers, the BCPDCA ligand was subjected to thermal stability tests in synthetic seawater at reservoir-like temperature. The composition of the synthetic seawater used is shown in Table 1.

Figure 6:
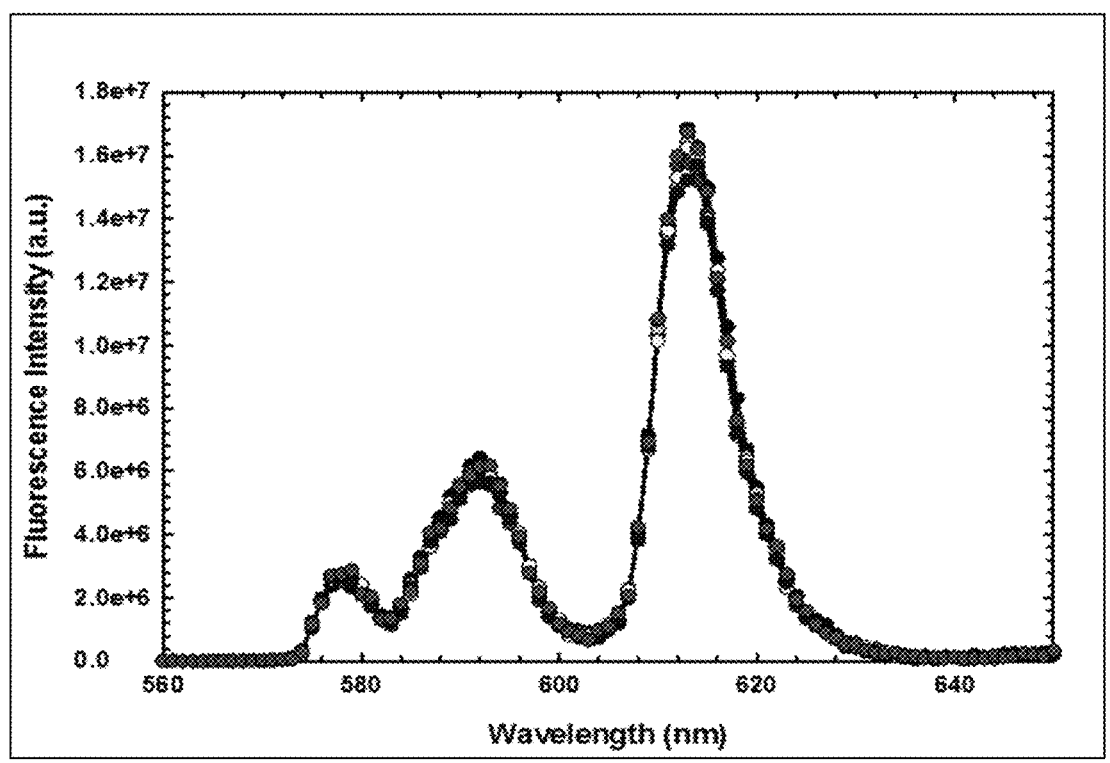
FIG. 6 is a plot showing luminescence emission as a function of wavelength for a complexing agent heated for different times.

200 ppb of BCPDCA, complexed with europium (III) using a $10^{-5}M$ solution of europium ions, was maintained at 103° C. in synthetic seawater over 11 days to determine whether its fluorescence intensity had changed. FIG. 6 is a plot showing fluorescence emission as a function of wavelength for BCPDCA heated for different times. Data shown in the six plots in FIG. 6 were measured on six different days over a 12-day interval. The near superposition of the plots indicated that the complex was thermally stable.

TABLE 1

| Composition of Synthetic Seawater | |
| --- | --- |
| Salt | Weight Percentage in Synthetic Seawater |
| NaCl | 3.949 |
| $CaCl_2 \cdot 2H_2O$ | 0.2297 |
| $MgCl_2 \cdot 6H_2O$ | 1.6998 |
| $BaCl_2$ | 0.00 |
| $Na_2SO_4$ | 0.611 |
| $NaHCO_3$ | 0.0159 |
| $Na_2CO_3$ | 0.00 |

Example 3—Photophysical Characterization of BCPDCA

Figure 7A:
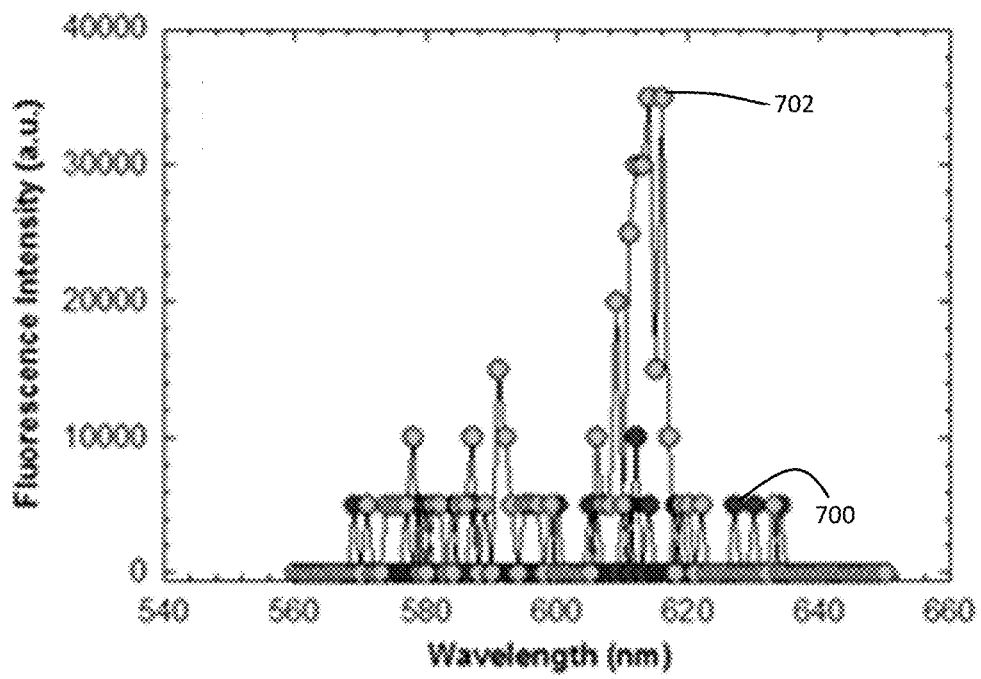
FIG. 7A is a plot showing luminescence emission as a function of wavelength for complexed and un-complexed europium.

Photophysical characterizations of the complexes including lanthanide ions and complexing agents were performed under experimental conditions that favored the formation of a 1:1 complex between a ligand and a lanthanide ion by including an excess of the lanthanides in solution. FIG. 7A is a plot showing luminescence emission as a function of wavelength for complexed and un-complexed europium ions. In deionized water, the limits of detection were determined to be in the 100's of parts-per-quadrillion (ppq) for complexes that formed between BCPDCA and europium (III) ions in solution, shown by plot 702. For reference, the un-complexed europium background plot 700 is also shown.

Figure 7B:
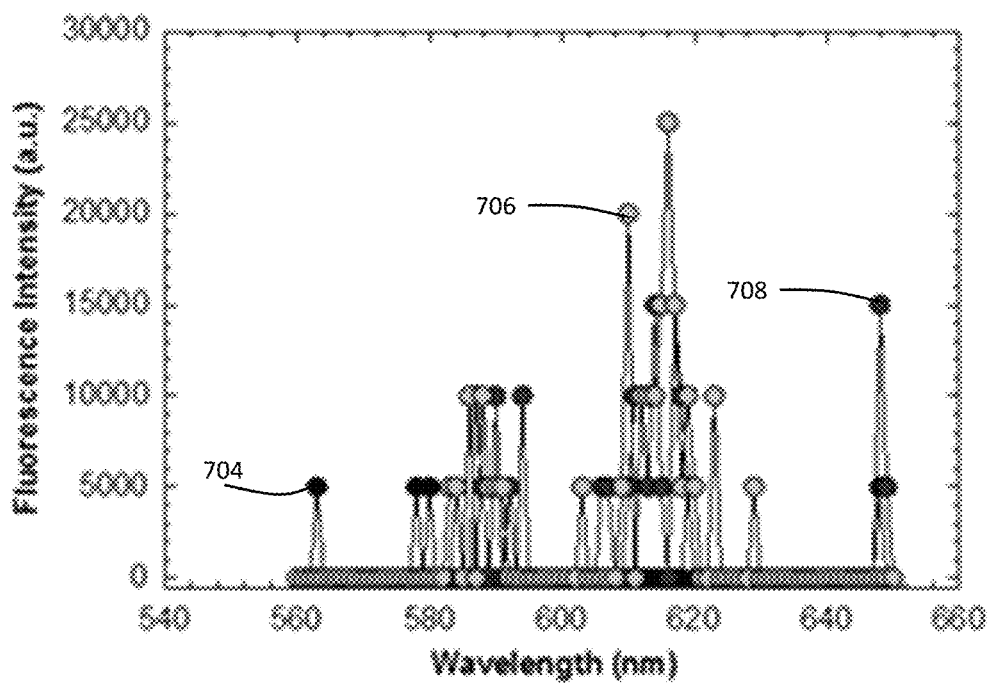
FIG. 7B is a plot showing luminescence emission as a function of wavelength for complexed europium, water extracted from a reservoir, and un-complexed europium.

Next, formation of the complex in produced water (which is oil contaminant-containing water) from a hydrocarbon reservoir, in which there existed excess calcium ions in solution, was performed. FIG. 7B is a plot showing luminescence emission as a function of wavelength for complexed europium, water extracted from a reservoir, and un-complexed europium. It was observed that the PAH's in produced water sensitized the lanthanide ions measurably, as shown by plot 704. In spite of this, it was possible to detect the presence of the complex to 10's of parts-per-trillion as shown by plot 706, without any chromatographic separation, pre-concentration, or purification. For reference, the un-complexed europium background is plot 708. Based on these results, it is expected that purification of the produced water by, for example, ultra-high performance liquid chromatography, would enable a detection limit close to that observed in the deionized water experiment.

Figure 14A:
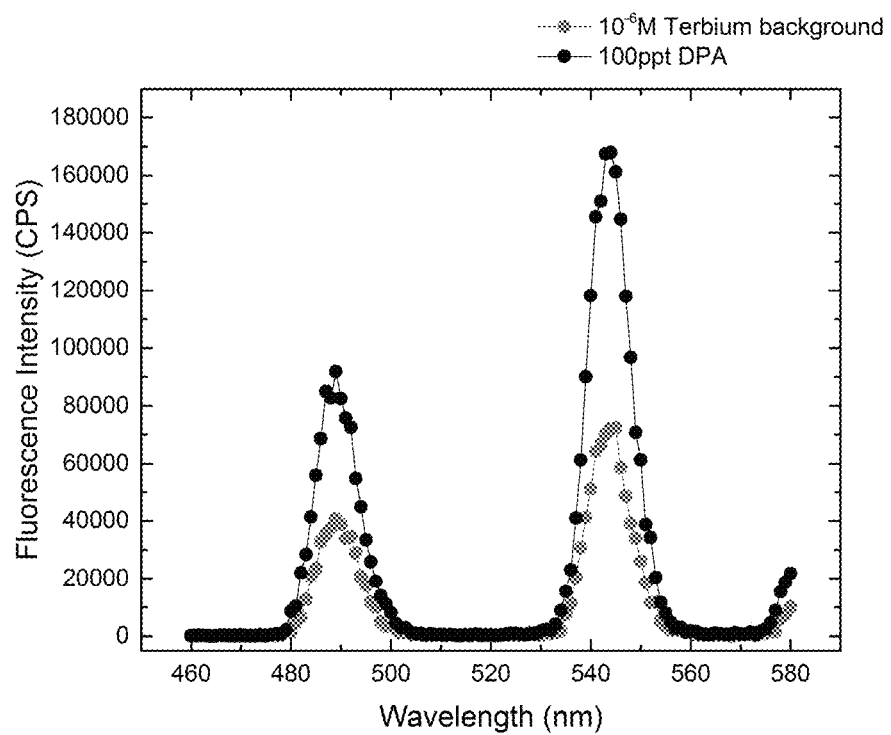
FIG. 14A is a plot of fluorescence intensity against wavelength for a DPA analog complexed with terbium ions in an acetate buffer.
Figure 14B:
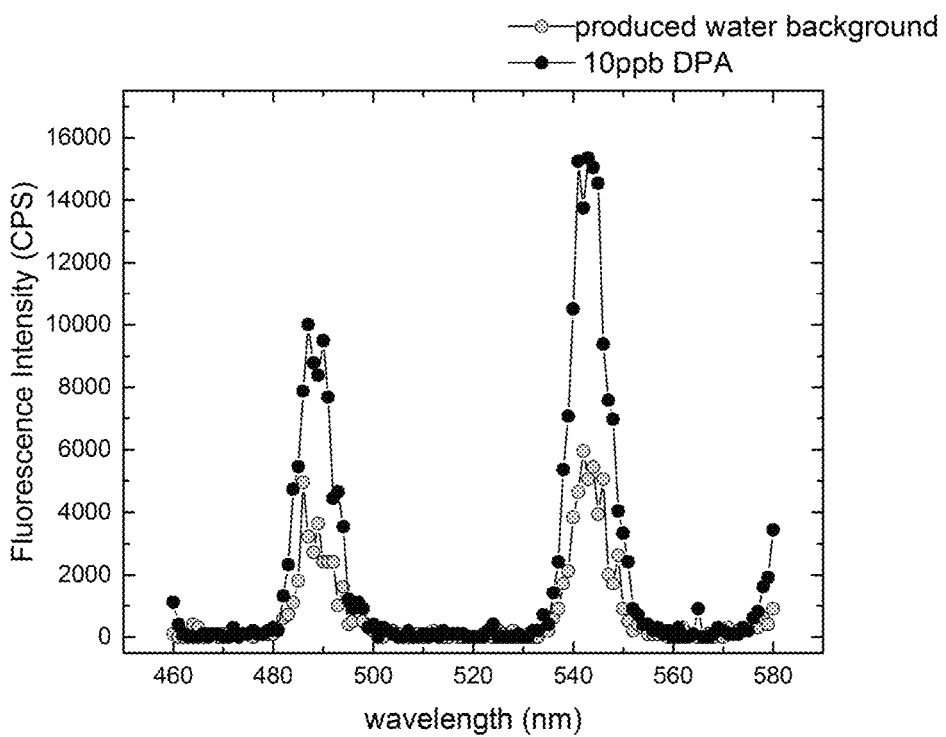
FIG. 14B is a plot of fluorescence intensity against wavelength for a DPA analog complexed with terbium ions in produced water from an extraction site.

As shown in FIGS. 14A and 14B, similar results were obtained in analogous experiments for complexing agents of Formula (I) when complexed with excess terbium ions at $10^{-6}$ M concentration to form primarily complexes having a 1:1 ratio of complexing agent to lanthanide ion. It was possible to detect concentrations of hundreds of parts-per-trillion (weight/weight) in acetate buffer, and concentrations smaller than 20 parts-per-billion (weight/weight) in produced water.

Example 4—Photophysical Characterization of BCPDCA

To determine the retention of BCPDCA materials in reservoir rocks under simulated reservoir conditions, mobility experiments were performed with parameters and results tabulated in Table 2, and described in forthcoming detail.

TABLE 2

Summary of Conditions for Mobility Experiments

| | |
|---|---|
| Core Identification: | Indiana Limestone, 70 milliDarcy (mD) as marked from Kocurek Industries |
| Core Permeability (brine): | 312 mD |
| Core Pore Volume: | 9.06 mL |
| Core Diameter: | 1.49 inches |
| Core Length: | 2.00 inches |
| Confinement Pressure ($P_{conf}$): | 4,400 pounds per square inch (psi) |
| Pore Pressure ($P_{pore}$): | 3,200 psi |
| Saturation Fluid: | degassed filtered (0.45 μm) synthetic seawater (57,670 milligrams per liter (mg/L) total dissolved solids (TDS)) |
| Permeability Test Fluid: | degassed filtered (0.45 μm) synthetic seawater (57,670 mg/L TDS) |
| Temperature (T): | 90° C. |
| Injection Rate (Q): | 0.5 mL/min |
| Concentration of Solution ($C_{solution}$): | 200 ppm BCPDCA tracer in synthetic seawater |
| Solution Preparation: | no pre-filtration, no pre-heating |
| Injection Pore Volume ($PV_{inject}$): | 3.48 |
| Flushing Solution: | degassed filtered (0.45 μm) synthetic seawater (57,670 mg/L TDS) |
| Flush Pore Volume ($PV_{flush}$): | 5 |
| Sampling Frequency: | 5+ vials per pore volume (PV) injected |
| Effluent Analysis: | Ultraviolet-visible absorbance (UV-VIS) at 290 nanometers (nm) |
| Irreversible Tracer Retention: | 6 μg/g ± 10% |

Coreflood Device and Conditions

A CoreTest Systems Inc. BPS-805Z Permeability System was used as a coreflood device. For the carbonates studied, values of confinement pressure $P_{conf}$=4,400 psi, pore pressure $P_{pore}$=3,200 psi, and temperature T=90° C. were used to replicate conditions in parts of the Ghawar reservoir in Saudi Arabia.

Saturation and Injection Brines

To reduce variables from transient salinity, the salinity of both the saturation fluid and injection fluid were matched for each respective experiment (for synthetic seawater, the core was saturated and flooded in seawater and the subsequent tracer ligand injection and flushes were all performed with seawater). The seawater used was intended to mimic the ionic composition of the injected fluid used throughout Saudi Arabia during water-flooding operations.

Tracer Injection and Analysis

The experiments were conducted at displacement velocities of 0.5 mL/min in Indiana Limestone. The brine flushing phase was conducted at the same displacement velocities as the tracer injections to avoid mobilization resulting from advection gradients. A tandem injection scheme was used. For the DPA and FBA comparison experiment, first FBA (~3 PV) was injected, followed by a flush of 5 pore volume of seawater before the DPA tracers are injected as a slug (~3 PV). A similar injection scheme was adopted for the BCPDCA & NaBr coreflood experiment.

For determining the tracer concentration, an Agilent spectrophotometer was used to measure the UV-VIS absorbance at a wavelength of 270 nm for DPA, and 290 nm for BCPDCA. For the ideal non-reactive ionic tracer NaBr, a bromine ion selective electrode was used to measure the eluents. A new 5-point calibration curve was made for each experiment measured. By comparing the effluent sample absorbance to the known values of the standards, a normalized concentration was derived for each fraction collected, annotated as $C/C_0$ (fraction of effluent sample concentration divided by input concentration; a value of 1.0 indicates the effluent solution is equal to the injected concentration). The fraction collector vials were weighed before and after sample collection to determine a collected mass from each vial. The known mass along with the known densities of the injection fluids allowed for volume calculations and validation of the injection rates.

Coreflood Tests Using BCPDCA

Figure 8:
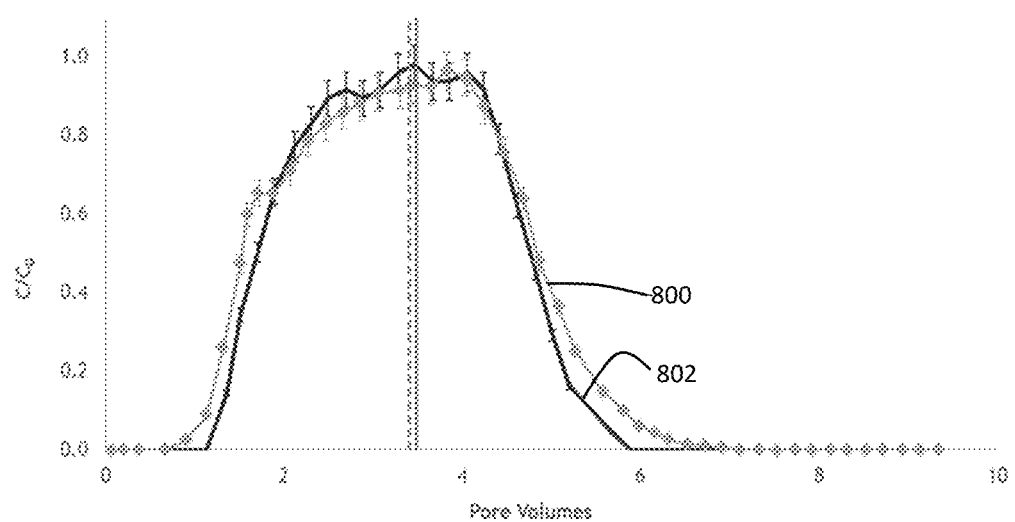
FIG. 8 is a plot of normalized concentration of a complexing agent against pore volumes for a complexing agent and a sodium bromide (NaBr) tracer.

BCPDCA in synthetic seawater was injected into a core at 200 mg/L at 90° C. Another test using an ionic tracer known to not attach to the rock matrix (0.1M NaBr in this case) in the same core was performed as well. FIG. 8 is a plot of normalized concentration of BCPDCA vs. pore volumes for a complexing agent and an NaBr tracer. The effluent curve 800 of the BCPDCA tracer was very similar to that of the 0.1M NaBr non-reactive ionic tracer curve plot 802, indicating that the core allowed passage of the complexing agent. The vertical solid and dotted lines indicate when a flush was initiated in the BCPDCA and NaBr experiments, respectively. The relatively steep slope of the plots as they approach $C/C^0=1.0$ indicates there is very little retention, thus showing that BCPDCA performed suitably as an inter-well tracer.

Figure 9:
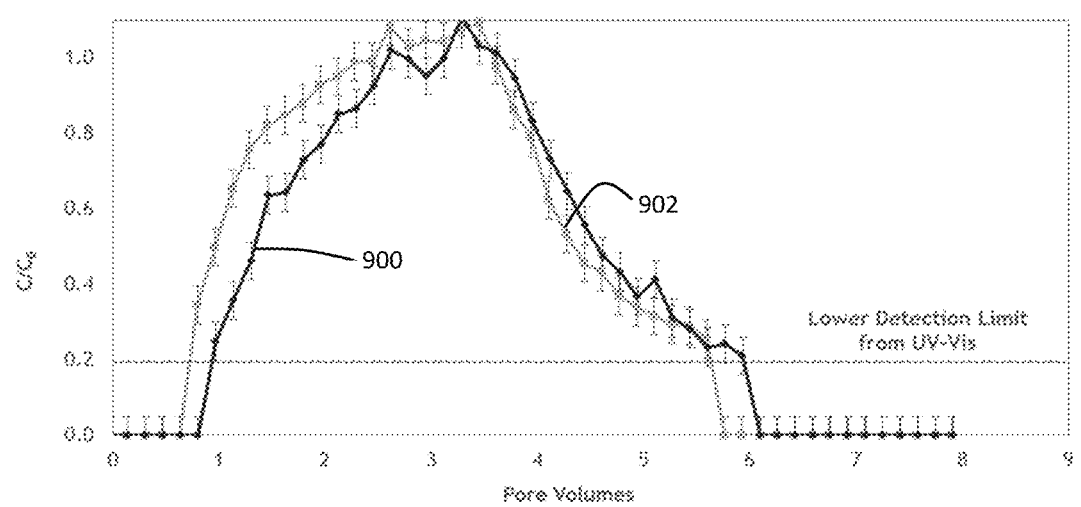
FIG. 9 is a plot of normalized concentration of a complexing agent vs. pore volumes for a complexing agent and a fluorinated benzoic acid (FBA) tracer.

A similar test was conducted using DPA, and a fluorinated benzoic acid (FBA) as the inert reference. FIG. 9 is a plot of normalized concentration of DPA vs. pore volumes for DPA and a fluorinated benzoic acid (FBA) tracer. Overall, the effluent curve 900 of the DPA tracer tracked very closely with that of the FBA curve 902. The steep increase before 1 pore volume indicated little to no retention of the tracers. These results suggest that DPA, too, exhibits suitable characteristics as an inter-well tracer for a carbonate reservoir.

Example 5—DPA Barcodes Separation by HPLC and Photophysical Comparison

Figure 13A:
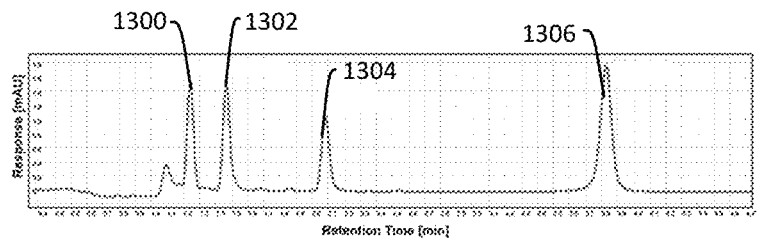
FIG. 13A is a high-pressure liquid chromatography (HPLC) trace of response factor against retention time for four dipicolinic acid (DPA) analogs.
Figure 13B:
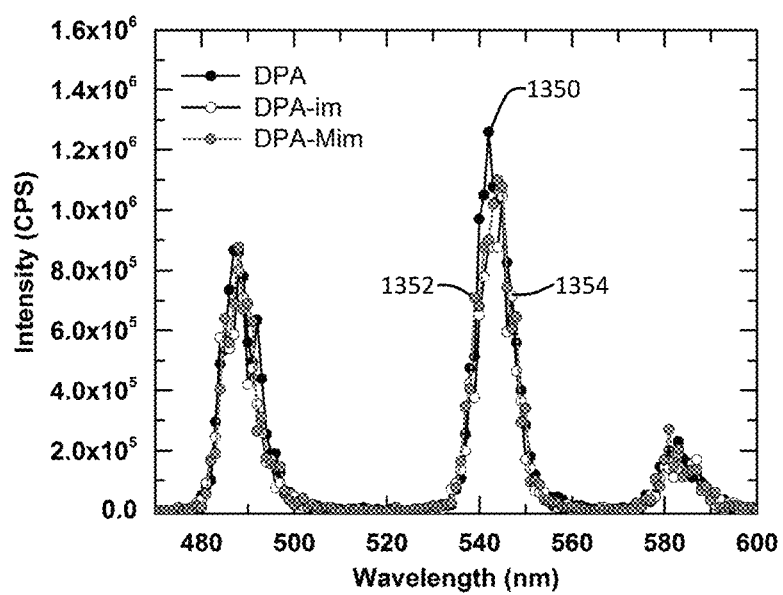
FIG. 13B is a plot of fluorescence intensity against wavelength for three DPA analogs.

Derivatives substituted with imidazolyl, 4-methylimidazolyl, and 4-ethylimidazolyl substituents at the 4-position of DPA were synthesized as shown in Scheme 2c. A mixture of DPA and three DPA derivatives substituted with imidazol-1-yl (DPA-im), 4-methylimidazol-1-yl (DPA-Mim) and 4-ethylimidazol-1-yl (DPA-Eim) groups at concentrations of 10 ppm each in water was chromatographically separated by UHPLC. FIG. 13A is an HPLC trace of response factor vs. retention time for DPA and each of the three DPA derivatives. The order of elution was (1) DPA, represented by peak 1306, (2) 4-ethylimidazol-1-yl DPA, represented by peak 1304, (3) 4-methylimidazol-1-yl DPA, represented by peak 1302, and (4) imidazol-1-yl DPA, represented by peak 1300, Fluorescence intensities of DPA, imidazol-1-yl DPA, and 4-methylimidazol-1-yl DPA at the same molar concentrations were measured after complexation with terbium ions. FIG. 13B is a plot of fluorescence intensity vs. wavelength for the 3 analogs. Plot 1350 shows the curve for DPA, plot 1352 shows the curve for 4-methylimidazol-1-yl DPA, and plot 1354 shows the curve for imidazol-1-yl DPA. These results indicated that the light harvesting capability of the derivatives remained unchanged after the chemical modification, as evidenced by the similar fluorescence intensities.

Example 6—Tracer Mobility Characterization

To assess the mobility of the molecular tracers through carbonate rocks under simulated reservoir conditions, coreflood experiments were performed. A one-foot long limestone core (permeability ~200 mDarcy, other properties shown in Table 3) was flooded with synthetic seawater, then flooded with Arabic medium crude (API ~30°) and aged for three weeks at 100° C. At the end of aging, the core was oil flooded again and initial oil saturation, $S_{oi}$, was calculated by mass balance. Then, the core was waterflooded with seawater to obtain residual oil saturation, $S_{orw}$, by mass balance. For the tracer flood, both the ideal ionic tracer, potassium chloride (KCl), and one of the molecular tracers described above were injected at the same pulse width of 0.5 pore volume (PV). The concentration of KCl was 1000 ppm in seawater, whereas the molecular tracer concentration was 100 ppm. Injection was followed by several PV chase of synthetic seawater. The concentration of potassium ions in the effluent was determined using ion chromatography while the concentration of the molecular tracer was measured by UV-Vis spectrophotometry.

TABLE 3

Limestone Core Properties for Coreflood Measurements

| Rock Type | Indiana limestone |
|---|---|
| Diameter | 3.81 cm |
| Length | 30.96 cm |
| Mass | 776.3 g |
| Bulk Volume | 352.97 cm$^3$ |
| Porosity | 0.179% |
| Area | 11.40 cm$^2$ |
| Pore Volume | 63.1 cm$^3$ |

Coreflood experimental conditions are summarized in Table 4.

TABLE 4

Coreflood Experimental Conditions

| Flood | Brine | Oil | Brine | Tracer |
|---|---|---|---|---|
| Fluid | Synthetic seawater | Arab medium crude | Synthetic seawater | 1000 ppm KCl, 100 ppm molecular tracer in seawater |
| Flow Rate (mL/min) | 5 | 5 | 1 | 0.09 |
| Frontal Velocity (ft/day) | 116 | 116 | 23 | 2 |

FIG. 15A is a plot showing normalized recovered concentrations (breakthrough curves) of the KCl and molecular tracers as a function of eluted pore volumes. Since the experiment was performed with both tracers injected in the same pulse width, many potential sources of experimental error were eliminated. The slight tailing associated with the distal portion of the curve for the molecular tracer was attributed to diffusion or retention. Since the small ions of the KCl tracer should be at least as diffusive as the larger tracer molecules, it is likely that greater reversible retention of the tracer (small molecules) compared to the K+ ions occurred, similar to what has been observed in other studies.

FIG. 15B shows mass recovery plots for both tracers. The plots suggest that there was negligible irreversible retention of the molecular tracer, indicating good transport through the rock matrices at simulated reservoir temperature and pressure.

Example 7—Detectability Characterization

To assess the detectability of the molecular tracers in the field, a study was performed using a specific well pair. FIG. 16 is a schematic diagram showing well sites in a specific field. For this study, well pair I3-P3 was chosen (a separation of 475 m). For this well pair, connectivity has been thoroughly characterized in previous water tracer studies and nanoagent tracer field tests.

A total of 5 kg of the first molecular tracer was first dissolved in approximately 200 L of deionized water. At the well site, a pre-flush of 4 barrels of treated seawater was administered at a rate of 0.35 bbl/min. Then, the molecular tracer was injected at I3 at a rate of 0.40 bbl/min. After the injection, a post flush with 10 barrels of treated seawater was injected at 0.5 bbl/min. Seawater injection at 3000 psi at a rate of approximately 8000 bbl/day resumed immediately post flush.

Produced water samples from producer well P3 were collected twice weekly. A cursory clean-up procedure involving solid phase extraction and fraction collection on a high performance liquid chromatograph was performed before the addition of lanthanide ions for the fluorescence measurements. With these additional steps, the cycle time for sample work up was still comparatively shorter than tracer detection methodologies for FBAs using quadrupole GC/MS.

Figure 17:
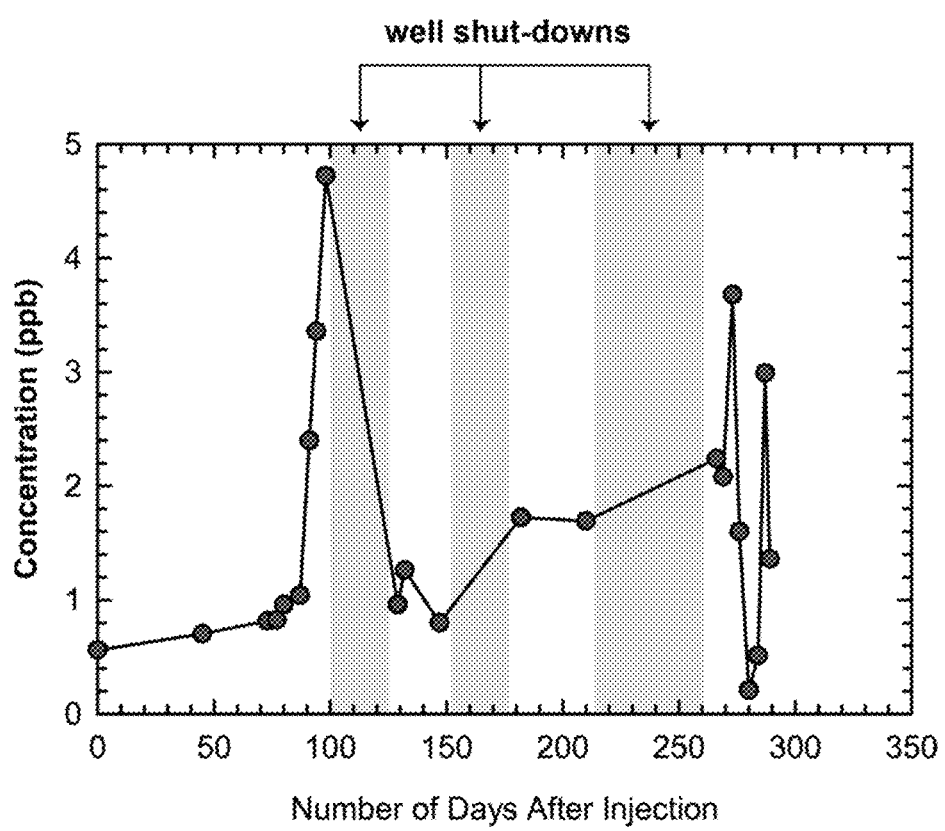
FIG. 17 is a recovery curve for a molecular tracer in produced water.

The recovery curve of the first molecular tracer is shown in FIG. 17. The data point on Day 0 refers to the background noise floor level to be expected for the analysis method for this particular tracer. Consistent above-background signal from the tracer could be detected after Day 50 and the signal trended upward unambiguously. However, due to long periods of well shut down for planned maintenance, no samples were collected between 100 days and 130 days after injection, as indicated on the plot. Other significant well shut down periods are also indicated. When the sample collection resumed, the upward trend of detectable tracer concentration continued, signifying breakthrough of the first molecular tracer.

Example 8—Tracer Information for Reservoir Management

Reservoir modeling methodologies have shown that active rate management is an effective way to augment productivity, particularly in mature fields. Although the value of tracer data in elucidating reservoir heterogeneity and reducing uncertainties is undeniable, its utility in fortifying the fidelity of reservoir history matching and enhancing production optimization algorithms does not appear to have been studied systematically.

Using reservoir history matching and production optimization algorithms, it was recently demonstrated that tracer data can improve field production net present values (NPVs) by +0.3% to +9.4% for non-homogeneously flooded reservoirs. The present example shows results of further feasibility studies for scaled-up reservoir models.

Figure 18A:
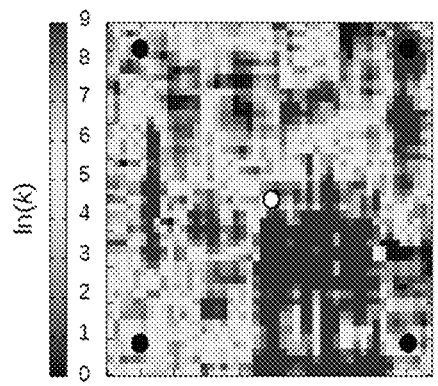
FIGS. 18A-18C are plots showing reference reservoir models.
Figure 18B:
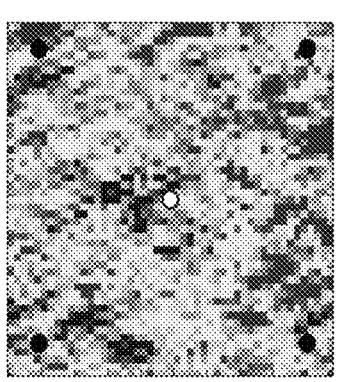
Figure 18C:
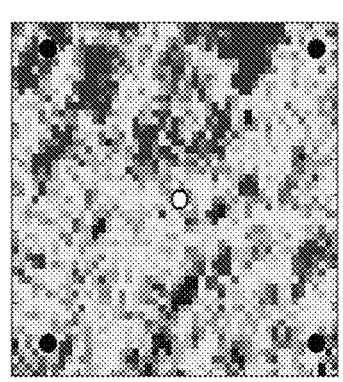

Permeability fields of the scaled-up reference reservoir models with five-spot waterflood patterns are shown in FIGS. 18A-18C. Each of the models was constructed on a 50×50×1 grid block system with block sizes of $\Delta x=\Delta y=250$ ft and $\Delta z=80$ ft. Values of constant porosity $\varphi=0.2$ and initial water saturation $S_w=0.1$ were used. Initial water injection rates were $q_0=20,000$ ft$^3$/day on the 4 injectors for the interval from 0 to 5,000 days. In addition, 4 unique molecular tracers were also injected in each injector and collected from the producer well for history matching.

Figure 18D:
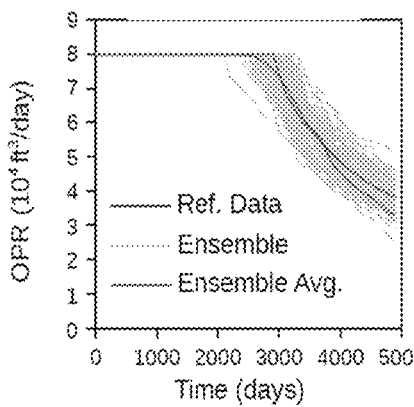
FIGS. 18D-18F are plots showing history-matched oilfield production rates for the reservoir models of FIGS. 18A-18C.
Figure 18E:
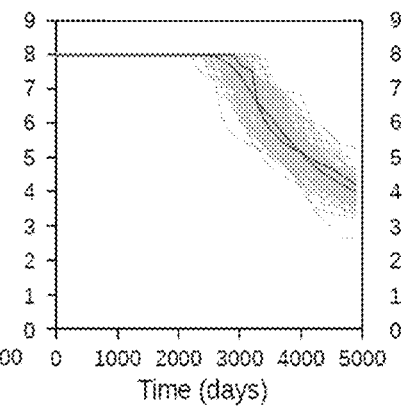
Figure 18F:
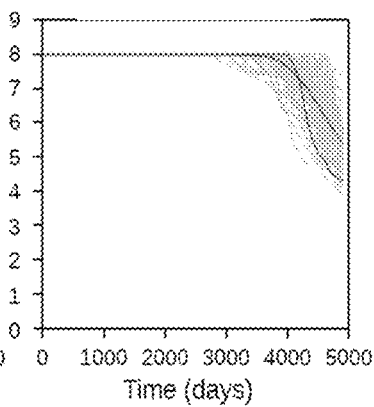

FIGS. 18D-18F are plots showing history matching results from the ensemble smoother with multiple data assimilation with molecular tracer data (ES-MDA-Tracer) algorithm. As shown in the figures, very good history matching was achieved for the first two models (FIGS. 18D and 18E) with early water and tracer breakthroughs. In contrast, for the third model (FIG. 18F), late water breakthrough resulted in less optimal history matching.

Figure 18G:
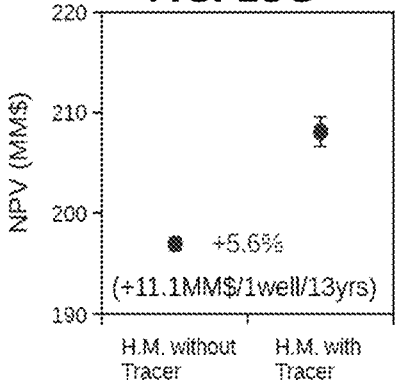
FIGS. 18G-18I are plots showing net present value for reservoirs managed with and without molecular tracer information for the reservoir models of FIGS. 18A-18C.
Figure 18H:
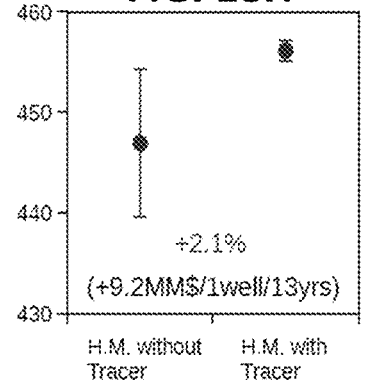
Figure 18I:
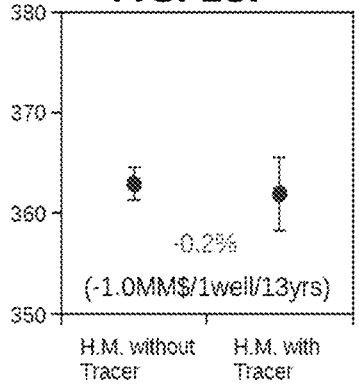

FIGS. 18G-18I are plots showing field production net present value (NPV) for the period from 5,000 to 10,000 days with waterflood optimization using reservoir models history matched with and without molecular tracer data. For models exhibiting good history matching (FIGS. 18D and 18E), increases of +5.6% and +2.1% NPV were observed with molecular tracer data (+$11.1 M and +$9.2 M/1 well/13 yrs), as shown in FIGS. 18G and 18H. For the less optimal model (FIG. 18F), a minor −0.2% NPV loss was observed with tracer data (−$1.0 M/1 well/13 yrs), as shown in FIG. 18I. Based on this data, the financial incentives are high if data from the molecular tracers are used to guide management of the reservoir models.

OTHER EMBODIMENTS

A number of embodiments have been described. Nevertheless, it will be understood that various modifications may be made without departing from the scope of the disclosure. Accordingly, other embodiments are within the scope of the following claims.

What is claimed is:

1. A complexing agent of Formula (II), or an anion or salt thereof:

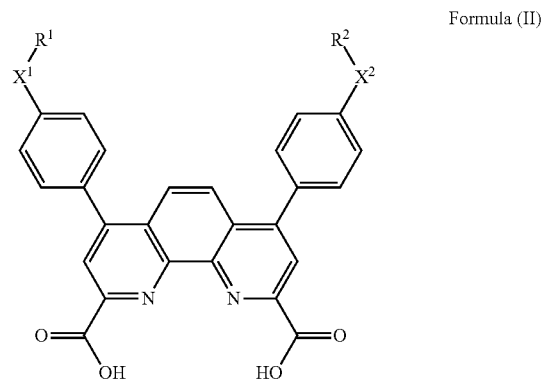

Formula (II)

wherein:
each of $X^1$ and $X^2$ is absent;
each of $R^1$ and $R^2$ is $-NR^aR^a$;
each occurrence of $R^a$ is $C_{1-8}$ alkyl optionally substituted with from 1-3 independently selected $R^b$; and
each occurrence of $R^b$ is $C_{1-4}$ alkoxy.

2. The complexing agent of claim 1, wherein: at least one $R^a$ is different from another $R^a$.

3. The complexing agent of claim 1, wherein each $R^a$ is the same.

4. The complexing agent of claim 1, wherein at least one $R^b$ is different from another $R^b$.

5. The complexing agent of claim 1, wherein each $R^b$ is the same.

* * * * *